United States Patent
Kuntz et al.

(10) Patent No.: US 10,245,269 B2
(45) Date of Patent: *Apr. 2, 2019

(54) SALT FORM OF A HUMAN HISTONE METHYLTRANSFERASE EZH2 INHIBITOR

(71) Applicants: Epizyme, Inc., Cambridge, MA (US); Eisai R&D Management Co., Ltd., Tokyo (JP)

(72) Inventors: Kevin Wayne Kuntz, Woburn, MA (US); Kuan-Chun Huang, Andover, MA (US); Hyeong Wook Choi, Andover, MA (US); Kristen Sanders, Gilmanton, NH (US); Steven Mathieu, Andover, MA (US); Arani Chanda, Malden, MA (US); Francis Fang, Andover, MA (US)

(73) Assignees: Epizyme, Inc., Cambridge, MA (US); Eisai R&D Management Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/837,390

(22) Filed: Dec. 11, 2017

(65) Prior Publication Data

US 2018/0243316 A1 Aug. 30, 2018

Related U.S. Application Data

(63) Continuation of application No. 15/199,522, filed on Jun. 30, 2016, now Pat. No. 9,872,862, which is a continuation of application No. 14/394,431, filed as application No. PCT/US2013/036193 on Apr. 11, 2013, now Pat. No. 9,394,283.

(60) Provisional application No. 61/624,215, filed on Apr. 13, 2012.

(51) Int. Cl.
*A61K 31/5377* (2006.01)
*C07D 405/12* (2006.01)

(52) U.S. Cl.
CPC ........ *A61K 31/5377* (2013.01); *C07D 405/12* (2013.01)

(58) Field of Classification Search
CPC .................................................. A61K 31/5377
See application file for complete search history.

(56) References Cited

U.S. PATENT DOCUMENTS

| | | |
|---|---|---|
| 5,716,993 A | 2/1998 | Ozaki et al. |
| 5,948,803 A | 9/1999 | Maeda et al. |
| 7,122,547 B1 | 10/2006 | Huth et al. |
| 7,252,968 B2 | 8/2007 | Jenuwein et al. |
| 7,442,685 B2 | 10/2008 | Zhang et al. |
| 7,563,589 B2 | 7/2009 | Zhang et al. |
| 7,923,219 B2 | 4/2011 | Wang et al. |
| 8,410,088 B2 | 4/2013 | Kuntz et al. |
| 8,765,732 B2 | 7/2014 | Kuntz et al. |
| 9,090,562 B2 | 7/2015 | Kuntz et al. |
| 9,175,331 B2 | 11/2015 | Kuntz et al. |
| 9,334,527 B2 | 5/2016 | Kuntz et al. |
| 9,394,283 B2 | 7/2016 | Kuntz et al. |
| 9,522,152 B2 | 12/2016 | Kuntz et al. |
| 9,549,931 B2 | 1/2017 | Kuntz et al. |
| 9,872,862 B2 | 1/2018 | Kuntz et al. |
| 2002/0183324 A1 | 12/2002 | Jacobson et al. |
| 2004/0082619 A1 | 4/2004 | Tada et al. |
| 2005/0266473 A1 | 12/2005 | Zhang et al. |
| 2008/0182844 A1 | 7/2008 | Bjergarde et al. |
| 2008/0222741 A1 | 9/2008 | Chinnaiyan |
| 2008/0269289 A1 | 10/2008 | Frank et al. |
| 2008/0312292 A1 | 12/2008 | Yasui et al. |
| 2009/0012031 A1 | 1/2009 | Chinnaiyan et al. |
| 2009/0061443 A1 | 3/2009 | Zhang et al. |
| 2009/0203057 A1 | 8/2009 | Zhang et al. |
| 2010/0035912 A1 | 2/2010 | Debnath et al. |
| 2010/0113415 A1 | 5/2010 | Rajapakse et al. |
| 2011/0021362 A1 | 1/2011 | Trojer et al. |
| 2012/0264734 A1 | 10/2012 | Kuntz et al. |
| 2013/0040906 A1 | 2/2013 | Kuntz et al. |
| 2013/0123234 A1 | 5/2013 | Kuntz et al. |
| 2014/0288041 A1 | 9/2014 | Kuntz et al. |
| 2015/0065503 A1 | 3/2015 | Kuntz et al. |
| 2015/0353494 A1 | 12/2015 | Kuntz et al. |
| 2016/0022693 A1 | 1/2016 | Kuntz et al. |

FOREIGN PATENT DOCUMENTS

| | | |
|---|---|---|
| EP | 1357111 | 10/2003 |
| JP | 7033729 | 2/1995 |
| WO | WO 1996/040100 | 12/1996 |
| WO | WO 2000/018725 | 4/2000 |
| WO | WO 2003/079788 | 10/2003 |
| WO | WO 2006/116713 | 11/2006 |

(Continued)

OTHER PUBLICATIONS

Braña et al. "Reaction of N-(2-Pyridylmethyl)-3,5-dimethylbenzamide and N-(3-Pyridylmethyl)-3,5-dimethylbenzamide N-Oxides With Acetic Anhydride." Journal of Heterocyclic Chemistry, 19:6(1982), 1297-1300.

(Continued)

*Primary Examiner* — Rebecca L Anderson
*Assistant Examiner* — Karen Cheng
(74) *Attorney, Agent, or Firm* — Cooley LLP; Heidi A. Erlacher; Christine C. Pemberton

(57) ABSTRACT

Provided herein is N-((4,6-dimethyl-2-oxo-1,2-dihydropyridin-3-yl)methyl)-5-(ethyl (tetrahydro-2H-pyran-4-yl) amino)-4-methyl-4'-(morpholinomethyl)-[1,1'-biphenyl]-3-carboxamide hydrobromide. Also provided herein is a particular polymorph form of this compound.

18 Claims, 19 Drawing Sheets

Specification includes a Sequence Listing.

(56) References Cited

FOREIGN PATENT DOCUMENTS

| | | |
|---|---|---|
| WO | WO 2007/045462 | 4/2007 |
| WO | WO 2007/050347 | 5/2007 |
| WO | WO 2007/070818 | 6/2007 |
| WO | WO 2007/136592 | 11/2007 |
| WO | WO 2008/073138 | 6/2008 |
| WO | WO 2008/103277 | 8/2008 |
| WO | WO 2008/104077 | 9/2008 |
| WO | WO 2008/108825 | 9/2008 |
| WO | WO 2008/113006 | 9/2008 |
| WO | WO 2009/058298 | 5/2009 |
| WO | WO 2009/077766 | 6/2009 |
| WO | WO 2009/124137 | 10/2009 |
| WO | WO 2010/018328 | 2/2010 |
| WO | WO 2010/111653 | 9/2010 |
| WO | WO 2011/082044 | 7/2011 |
| WO | WO 2011/140324 | 11/2011 |
| WO | WO 2011/140325 | 11/2011 |
| WO | WO 2012/005805 | 1/2012 |
| WO | WO 2012/034132 | 3/2012 |
| WO | WO 2012/068589 | 5/2012 |
| WO | WO 2012/075080 | 6/2012 |
| WO | WO 2012/075500 | 6/2012 |
| WO | WO 2012/118812 | 9/2012 |
| WO | WO 2012/142504 | 10/2012 |
| WO | WO 2012/142513 | 10/2012 |
| WO | WO 2013/138361 A1 | 9/2013 |
| WO | WO 2013/155317 | 10/2013 |
| WO | WO 2013/173441 | 11/2013 |

OTHER PUBLICATIONS

Chemical Abstracts Service Registry Nos. 1111568-29-6, 1111508-57-6, and 1111473-93-8 entered Feb. 25, 2009, 2 pages.
Chemical Abstracts Service Registry Nos. 1118856-92-0, 1118847-80-5, 1118847-59-8, 1118826-65-5, 1118826-02-0, 1118825-96-9, 1118825-75-4, 1118825-72-1, and 1118825-69-6 entered Mar. 11, 2009, 4 pages.
Chemical Abstracts Service Registry Nos. 1278089-60-3, 1277914-52-9, and 1277529-83-5, entered Apr. 10, 2011, 2 pages.
Chemical Abstracts Service Registry Nos. 1278854-92-4 and 127885491-3, entered Apr. 12, 2011, 1 page.
Chemical Abstracts Service Registry Nos. 919939-47-2 and 919873-05-5 entered Feb. 8, 2007, 1 page.
Chemical Abstracts Service Registry Nos. 923162-97-4, 923152-74-3, and 923111-85-7 entered Feb. 26, 2007, 2 pages.
Chemical Abstracts Service Registry Nos. 923774-47-4, 923730-10-3, and 923690-12-4 entered Feb. 28, 2007, 2 pages.
Chemical Abstracts Service Registry Nos. 941139-86-2 and 941091-93-6 entered Jul. 4, 2007, 1 page.
Gura et al. "Systems for Identifying New Drugs are Often Faulty." Science, 278:5340(1997), 1041-1042.
Johnson et al. "Relationships Between Drug Activity in NCI Preclinical in vitro and in vivo Models and Early Clinical Trials." Brit. J. Cancer. 84:10(2001),1424-1431.

Knutson et al. "A Selective Inhibitor of EZH2 Blocks H3K27 Methylation and Kills Mutant Lymphoma Cells." Nat. Chem. Biol. (2012):1-7. Epub: Sep. 30, 2012.
Lohr et al. "Discovery and Prioritization of Somatic Mutations in Diffuse Large B-Cell Lymphoma (DLBCL) by Whole-Exome Sequencing." PNAS. 109.10(2012):3879-3884. Epub Feb. 17, 2012.
Martinez-Garcia et al. "The MMSET Histone Methyl Transferase Switches Global Histone Methylation and Alters Gene Expression in t(4;14) Multiple Myeloma Cells." Blood. 117:1 (2011), 211-220.
McCabe et al. "EZH2 Inhibition as a Therapeutic Strategy for Lymphoma With EZH2-Activating Mutations." Nature. Epub: Oct. 10, 2012.
McCabe et al. "Mutation of A677 in Histone Methyltransferase EZH2 in Human B-Cell Lymphoma Promotes Hypertrimethylation of Histone H3 on Lysine 27 (H3K27)." PNAS.109:8(2012), 2989-2994.
Miranda et al. "DZNep is a Global Histone Methylation Inhibitor That Reactivates Developmental Genes not Silenced by DNA Methylation." Mol. Cancer Ther. 8:6(2009), 1579-1588.
Morin et al. "Somatic Mutations Altering EZH2 (Tyr641) in Follicular and Diffuse Large B-Cell Lymphomas of Germinal-Center Origin." Nat. Genet. 42:2(2010), 181-185.
Pearce et al. "Failure Modes in Anticancer Drug Discovery and Development." Cancer Drug Design and Discovery. Neidle, ed. Boston: Elsevier. (2008),424-435.
Sculley et al. "Some Amide Derivatives of Certain Aminomethylpyridines." J. Am. Chem. Soc. 75:14(1953), 3400-3403.
Simone. "Oncology: Introduction." Cecil Textbook of Medicine. Bennett et al., eds. Philadelphia: W. B. Saunders Co. 20th ed. 1, (1996), 1004-1008.
Sneeringer et al. "Coordinated Activities of Wild-Type Plus Mutant EZH2 Drive Tumor-Associated Hypertrimethylation of Lysine 27 on Histone H3 (H3K27) in Human B-Cell Lymphomas." PNAS. 107:49(2010), 20980-20985.
Wigle et al. "The Y641 C Mutation of EZH2 Alters Substrate Specificity for Histone H3 Lysine 27 Methylation States." FEBS Lett. 585:19(2011), 3011-3014.
Wilson et al. "Epigenetic Antagonism Between Polycomb and SWI/SNF Complexes During Oncogenic Transformation." Cancer Cell. 18(2010):316-328.
Yap et al. "Somatic Mutations at EZH2 Y641 Act Dominantly Through a Mechanism of Selectively Altered PRC2 Catalytic Activity, to Increase H3K27 Trimethylation." Blood. 117:.8(2010), 2451-2459.
The Japanese Pharmacopoeia, Sixteenth Edition, 2011, pp. 64-68 2.58 X-ray powder diffraction method, p. 2070.
Caira, M.R. (1998) "Crystalline Polymorphism of Organic Compounds" Topics in Current Chemistry, 198:163-208.
Garapaty-Rao, S. et al. (Nov. 2013) "Identification of EZH2 and EZH1 Small Molecule Inhibitors with Selective Impact on Diffuse Large B Cell Lymphoma Cell Growth" Chem Biol, 20:1329-1339.
Qi, W. et al. (2012) "Selective inhibition of Ezh2 by a small molecule inhibitor blocks tumor cells proliferation" Proc Natl Acad Sci USA, vol. 109, No. 52, p. 21360-21365.
Varambally, S. et al. (2002) "The Polycomb Group Protein EZH2 Is Involved in Progression of Prostate Cancer" Nature, 419:624-629.

SALT FORM OF A HUMAN HISTONE METHYLTRANSFERASE EZH2 INHIBITOR

RELATED APPLICATIONS

This application is a continuation application of U.S. Ser. No. 15/199,522, filed Jun. 30, 2016 (now allowed), which is a continuation application of U.S. patent application Ser. No. 14/394,431, filed Oct. 14, 2014, now U.S. Pat. No. 9,394,283, which is a U.S. National Phase Application of International Application No. PCT/US2013/036193, filed Apr. 11, 2013, which claims priority to, and the benefit of, U.S. Provisional Application No. 61/624,215, filed Apr. 13, 2012, the entire contents of each of which are incorporated herein by reference in their entireties.

INCORPORATION BY REFERENCE OF SEQUENCE LISTING

The contents of the text file named "EPIZ-010N01US SeqenceListing.txt", which was created on May 3, 2016 and is 1 KB in size, are hereby incorporated by reference in their entireties.

BACKGROUND OF THE INVENTION

More than 1.6 million people are estimated to be diagnosed with cancer in 2012. For example, the most common type of cancer in women is breast cancer, and this disease is responsible for one of the highest fatality rates of all cancers affecting females. The current treatment of breast cancer is limited to total, or partial, mastectomy, radiation therapy, or chemotherapy. Almost 230,000 of cancer cases in 2012 will be breast cancer, which will result in an estimated 40,000 deaths. See, Siegel et al., Ca Cancer J Clin 2012; 62:10-29.

A number of cancer deaths are caused by blood cancers including leukaemias, myelomas, and lymphomas. In 2012, almost 80,000 of cancer cases will be lymphomas, which will result in an estimated 20,000 deaths.

Radiation therapy, chemotherapy, and surgery are the primary methods of cancer treatment. However, these therapies are most successful only when the cancer is detected at an early stage. Once cancer reaches invasive/metastatic stages, lines of invading cells or metastasizing cells can escape detection, thus resulting in relapses, which requires the use of therapy that is highly toxic. At this point, both the cancer cells and the patient's unaffected cells are exposed to the toxic therapy, resulting, among other complications, a weakening of the immune system.

As such, there remains a need in the art for new methods for treating cancer, such as breast cancer or lymphomas, in a patient.

SUMMARY OF THE INVENTION

Accordingly, provided herein is N-((4,6-dimethyl-2-oxo-1,2-dihydropyridin-3-yl) methyl)-5-(ethyl (tetrahydro-2H-pyran-4-yl)amino)-4-methyl-4'-(morpholinomethyl)-[1,1'-biphenyl]-3-carboxamide hydrobromide:

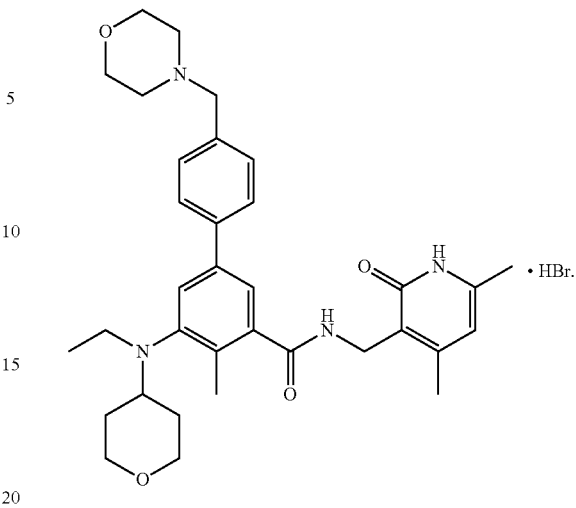

Also provided herein is a particular polymorph form of N-((4,6-dimethyl-2-oxo-1,2-dihydropyridin-3-yl)methyl)-5-(ethyl (tetrahydro-2H-pyran-4-yl)amino)-4-methyl-4'-(morpholinomethyl)-[1,1'-biphenyl]-3-carboxamide hydrobromide ("Polymorph A," or "Polymorph A of N-((4,6-dimethyl-2-oxo-1,2-dihydropyridin-3-yl)methyl)-5-(ethyl (tetrahydro-2H-pyran-4-yl)amino)-4-methyl-4'-(morpholinomethyl)-[1,1'-biphenyl]-3-carboxamide hydrobromide"). As described herein, the hydrobromide salt provided herein, as well as Polymorph A, exhibit physical properties that can be exploited in order to obtain new pharmacological properties, and that may be utilized in drug substance and drug product development.

In one embodiment, the hydrobromide is crystalline. In another embodiment, the hydrobromide is substantially free of impurities. In another embodiment, the hydrobromide is a crystalline solid substantially free of amorphous N-((4,6-dimethyl-2-oxo-1,2-dihydropyridin-3-yl) methyl)-5-(ethyl (tetrahydro-2H-pyran-4-yl)amino)-4-methyl-4'-(morpholinomethyl)-[1,1'-biphenyl]-3-carboxamide hydrobromide.

In another aspect, provided herein is a pharmaceutical composition comprising the hydrobromide described above, and a pharmaceutically acceptable carrier or diluent.

In one aspect, the hydrobromide described above is prepared using a method comprising combining N-((4,6-dimethyl-2-oxo-1,2-dihydropyridin-3-yl)methyl)-5-(ethyl (tetrahydro-2H-pyran-4-yl)amino)-4-methyl-4'-(morpholinomethyl)-[1,1'-biphenyl]-3-carboxamide with hydrobromic acid.

Polymorph A of N-((4,6-dimethyl-2-oxo-1,2-dihydropyridin-3-yl)methyl)-5-(ethyl (tetrahydro-2H-pyran-4-yl) amino)-4-methyl-4'-(morpholinomethyl)-[1,1'-biphenyl]-3-carboxamide can be defined according to its X-ray powder diffraction pattern. Accordingly, in one embodiment, the polymorph exhibits an X-ray powder diffraction pattern having one or more characteristic peaks expressed in degrees 2-theta at about 3.9+/−0.3 degrees, about 17.5+/−0.3 degrees, and about 22.0+/−0.3 degrees 2-theta. In another embodiment, the polymorph exhibits an X-ray powder diffraction pattern having characteristic peaks expressed in degrees 2-theta at about 3.9+/−0.3 degrees, about 17.5+/−0.3 degrees, and about 22.0+/−0.3 degrees 2-theta. In still another embodiment, the polymorph exhibits an X-ray powder diffraction pattern having characteristic peaks expressed in degrees 2-theta at about 3.9+/−0.3 degrees, 10.1+/−0.3 degrees, 14.3+/−0.3 degrees, 17.5+/−0.3 degrees, 18.7+/−

0.3 degrees, 20.6+/−0.3 degrees, 20.9+/−0.3 degrees, 21.8+/−0.3 degrees, 22.0+/−0.3 degrees, 23.3+/−0.3 degrees and 23.6+/−0.3 degrees 2-theta. In still another embodiment, the polymorph exhibits an X-ray powder diffraction pattern substantially in accordance with FIG. 1. In another embodiment, the polymorph exhibits an X-ray powder diffraction pattern substantially in accordance with Table 1.

Polymorph A can also be defined according to its differential scanning calorimetry thermogram. In one embodiment, the polymorph exhibits a differential scanning calorimetry thermogram having a characteristic peak expressed in units of ° C. at a temperature of 255+/−5° C. In an embodiment, the polymorph exhibits a differential scanning calorimetry thermogram substantially in accordance with FIG. 3.

In one aspect, Polymorph A is prepared using a method comprising combining N-((4,6-dimethyl-2-oxo-1,2-dihydropyridin-3-yl)methyl)-5-(ethyl (tetrahydro-2H-pyran-4-yl)amino)-4-methyl-4'-(morpholinomethyl)-[1,1'-biphenyl]-3-carboxamide with hydrobromic acid.

In another aspect, provided herein is a method of recrystallizing Polymorph A, which comprises the following steps: (a) dissolving Polymorph A in a first solvent, and (b) adding a second solvent, such that said polymorph is recrystallized. In one embodiment, the first solvent is ethanol, and the second solvent is MTBE. In another embodiment, the method comprises (a) dissolving Polymorph A in ethanol, (b) heating the mixture, (c) adding MTBE to the mixture, forming a precipitate comprising said polymorph, and filtering the precipitate such that said polymorph is recrystallized.

In still another aspect, provided herein is a pharmaceutical composition comprising Polymorph A, and a pharmaceutically acceptable carrier or diluent.

Also provided herein is a method of treating cancer comprising administering to a subject in need thereof a therapeutically effective amount of the hydrobromide compound described above, Polymorph A, or a pharmaceutical composition comprising either of these compounds. A variety of cancers can be treated, including non-Hodgkin's lymphoma or breast cancer.

In another aspect, provided herein is a method of inhibiting the histone methyltransferase activity of EZH2 in a subject in need thereof comprising administering to the subject an effective amount of the hydrobromide compound described above, Polymorph A, or a pharmaceutical composition comprising either of these compounds.

In still another aspect, provided herein is a method of inhibiting the histone methyltransferase activity of EZH2 in vitro comprising administering the hydrobromide compound described above, or Polymorph A.

Also provided herein is the use of the hydrobromide compound described above, Polymorph A, or a pharmaceutical composition comprising either of these compounds, for the preparation of a medicament for the treatment of cancer in a subject in need thereof.

DETAILED DESCRIPTION OF THE INVENTION

HBr Salt Form and Polymorph Form A

Provided herein is N-((4,6-dimethyl-2-oxo-1,2-dihydropyridin-3-yl)methyl)-5-(ethyl (tetrahydro-2H-pyran-4-yl)amino)-4-methyl-4'-(morpholinomethyl)-[1,1'-biphenyl]-3-carboxamide hydrobromide:

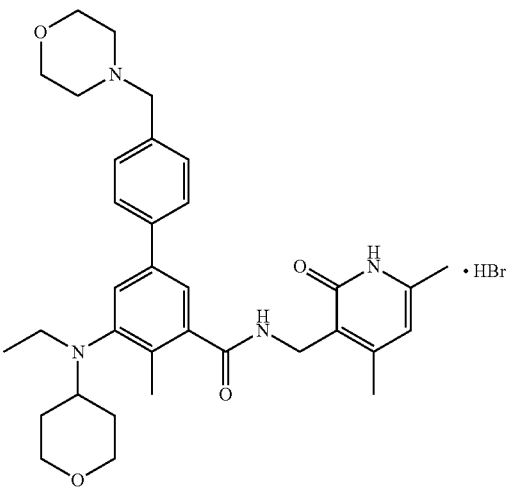 [SMILES: CCN(c1cc(-c2ccc(CN3CCOCC3)cc2)cc(C(=O)NCc2c(C)cc(C)[nH]c2=O)c1C)C1CCOCC1 ; "· HBr"]

As used herein, "Compound I" refers to N-((4,6-dimethyl-2-oxo-1,2-dihydropyridin-3-yl) methyl)-5-(ethyl (tetrahydro-2H-pyran-4-yl)amino)-4-methyl-4'-(morpholinomethyl)-[1,1'-biphenyl]-3-carboxamide. The hydrobromide of Compound I can be used to inhibit the histone methyltransferase activity of EZH2, either in a subject or in vitro. The hydrobromide of Compound I can also be used to treat cancer in a subject in need thereof.

Compound I can be protonated at one or more of its basic sites, such as the morpholine, disubstituted aniline, and/or pyridone moieties. Accordingly, in certain embodiments, provided herein is the monohydrobromide, dihydrobromide, or trihydrobromide of Compound I. In one embodiment, provided herein is the monohydrobromide of Compound I. When the compound is the monohydrobromide, the compound may be protonated at any basic site. In a non-limiting embodiment, Compound I is protonated at the nitrogen of the morpholino substituent, providing a monohydrobromide of Compound I having the following structure:

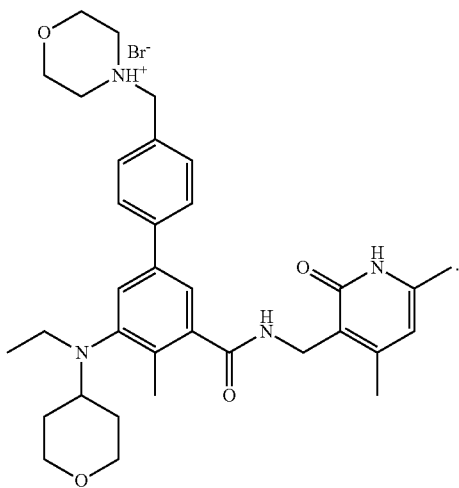 [SMILES: CCN(c1cc(-c2ccc(C[NH+]3CCOCC3)cc2)cc(C(=O)NCc2c(C)cc(C)[nH]c2=O)c1C)C1CCOCC1 ; [Br-]]

Figure 11:
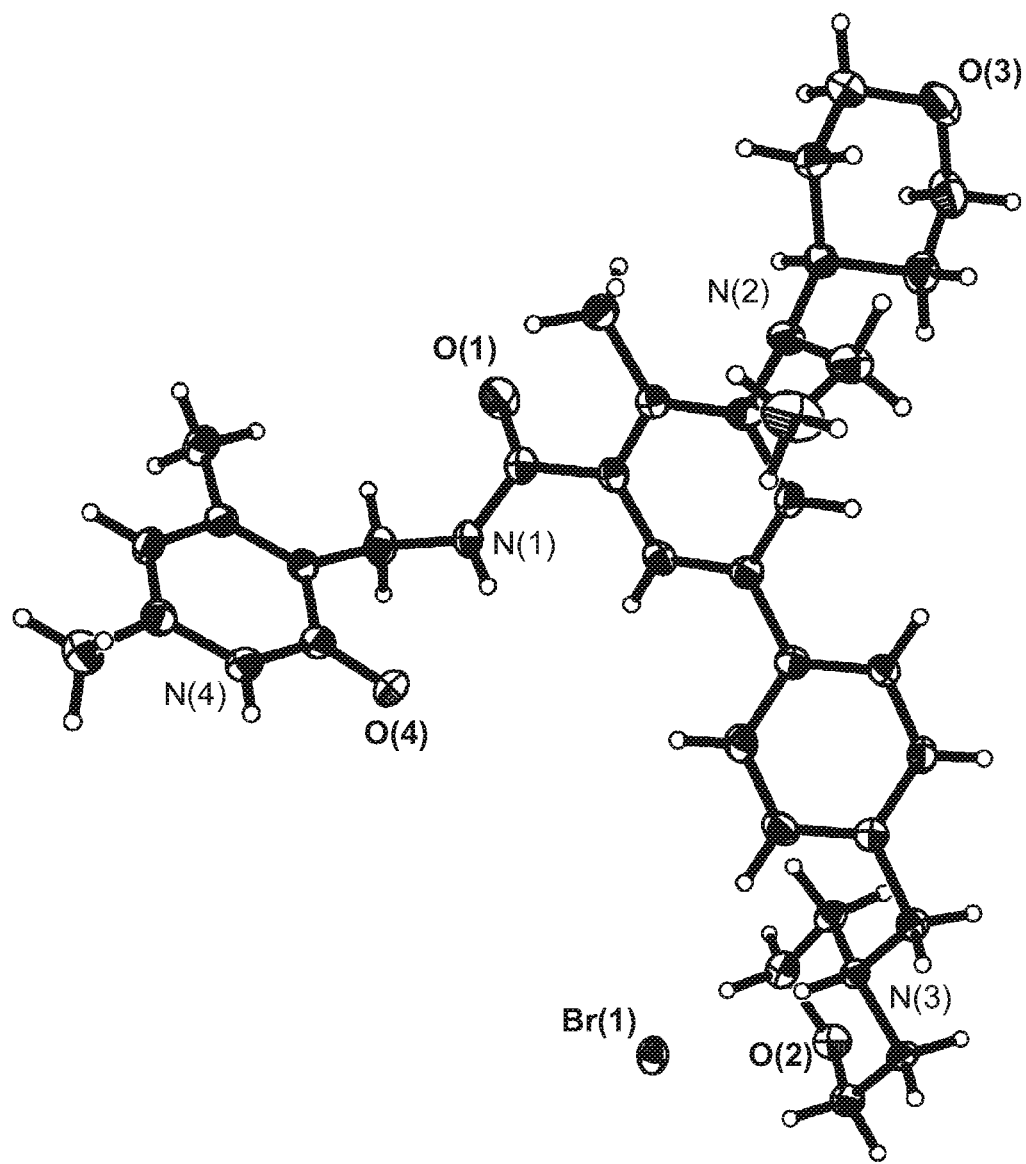
FIG. 11 depicts the X-ray crystal structure of the monohydrobromide of Compound I.

This particular monohydrobromide can be referred to as "4-((3'-(((4,6-dimethyl-2-oxo-1,2-dihydropyridin-3-yl) methyl)carbamoyl)-5'-(ethyl(tetrahydro-2H-pyran-4-yl) amino)-4'-methyl-[1,1'-biphenyl]-4-yl)methyl)morpholin-4-ium bromide." FIG. 11 depicts the X-ray crystal structure of this particular salt form.

The hydrobromide of Compound I has a number of advantageous physical properties over its free base form, as well as other salts of the free base. In particular, the hydrobromide of Compound I has low hygroscopicity compared to other salt forms of Compound I. For a compound to be effective in therapy, it is generally required that the compound be minimally hygroscopic. Drug forms that are highly hygroscopic may be unstable, as the drug form's dissolution rate may change as it is stored in settings with varying humidity. Also, hygroscopicity can impact large-scale handling and manufacturing of a compound, as it can be difficult to determine the true weight of a hygroscopic active agent when preparing a pharmaceutical composition comprising that agent. The hydrobromide of Compound I has a low hygroscopicity compared to other salt forms of Compound I. As such, it can be stored over appreciable periods, and not suffer from detrimental changes in, for example, solubility, density, or even chemical composition.

In addition to the above advantages, the hydrobromide of Compound I can be produced in a highly crystalline form, which is useful in the preparation of pharmaceutical formulations, and will improve general handling, manipulation, and storage of the drug compound. In a preferred embodiment, the crystalline form of the hydrobromide of Compound I is in a form referred to as "Polymorph A."

The ability of a substance to exist in more than one crystal form is defined as polymorphism; the different crystal forms of a particular substance are referred to as "polymorphs." In general, polymorphism is affected by the ability of a molecule of a substance to change its conformation or to form different intermolecular or intra-molecular interactions, particularly hydrogen bonds, which is reflected in different atom arrangements in the crystal lattices of different polymorphs. In contrast, the overall external form of a substance is known as "morphology," which refers to the external shape of the crystal and the planes present, without reference to the internal structure. Crystals can display different morphology based on different conditions, such as, for example, growth rate, stirring, and the presence of impurities.

The different polymorphs of a substance may possess different energies of the crystal lattice and, thus, in solid state they can show different physical properties such as form, density, melting point, color, stability, solubility, dissolution rate, etc., which can, in turn, affect the stability, dissolution rate and/or bioavailability of a given polymorph and its suitability for use as a pharmaceutical and in pharmaceutical compositions.

Polymorph A is highly crystalline, and displays low hygroscopicity. Also, this polymorph can be obtained reproducibly, and slight changes in crystallization conditions do not result in different crystal forms.

Access to different polymorphs of the hydrobromide of Compound I is desirable for a number of reasons. One such reason is that individual polymorphs can incorporate different impurities, or chemical residues, upon crystallization. For example, impurities can be removed during the process of converting Compound I into Polymorph A.

Without wishing to be bound by theory, polymorph forms exhibiting compact crystal shapes possess advantages in terms of ease of filtration and ease of flow. Polymorph A exhibits a compact crystal shape that therefore possesses these advantages.

In certain embodiments, Polymorph A is identifiable on the basis of characteristic peaks in an X-ray powder diffraction analysis. X-ray powder diffraction, also referred to as XRPD, is a scientific technique using X-ray, neutron, or electron diffraction on powder, microcrystalline, or other solid materials for structural characterization of the materials. In one embodiment, Polymorph A exhibits an X-ray powder diffraction pattern having one or more characteristic peaks expressed in degrees 2-theta at about 3.9+/−0.3 degrees, about 17.5+/−0.3 degrees, and about 22.0+/−0.3 degrees 2-theta. In another embodiment, the polymorph exhibits an X-ray powder diffraction pattern having characteristic peaks expressed in degrees 2-theta at about 3.9+/−0.3 degrees, about 17.5+/−0.3 degrees, and about 22.0+/−0.3 degrees 2-theta.

In one embodiment, Polymorph A exhibits an X-ray powder diffraction pattern having at least 5 characteristic peaks expressed in degrees 2-theta at about 3.9+/−0.3 degrees, 10.1+/−0.3 degrees, 14.3+/−0.3 degrees, 17.5+/−0.3 degrees, 18.7+/−0.3 degrees, 20.6+/−0.3 degrees, 20.9+/−0.3 degrees, 21.8+/−0.3 degrees, 22.0+/−0.3 degrees, 23.3+/−0.3 degrees and 23.6+/−0.3 degrees 2-theta. In another embodiment, Polymorph A exhibits an X-ray powder diffraction pattern having at least 6 characteristic peaks expressed in degrees 2-theta at about 3.9+/−0.3 degrees, 10.1+/−0.3 degrees, 14.3+/−0.3 degrees, 17.5+/−0.3 degrees, 18.7+/−0.3 degrees, 20.6+/−0.3 degrees, 20.9+/−0.3 degrees, 21.8+/−0.3 degrees, 22.0+/−0.3 degrees, 23.3+/−0.3 degrees and 23.6+/−0.3 degrees 2-theta. In yet another embodiment, Polymorph A exhibits an X-ray powder diffraction pattern having at least 7 characteristic peaks expressed in degrees 2-theta at about 3.9+/−0.3 degrees, 10.1+/−0.3 degrees, 14.3+/−0.3 degrees, 17.5+/−0.3 degrees, 18.7+/−0.3 degrees, 20.6+/−0.3 degrees, 20.9+/−0.3 degrees, 21.8+/−0.3 degrees, 22.0+/−0.3 degrees, 23.3+/−0.3 degrees and 23.6+/−0.3 degrees 2-theta. In another embodiment, Polymorph A exhibits an X-ray powder diffraction pattern having at least 8 characteristic peaks expressed in degrees 2-theta at about 3.9+/−0.3 degrees, 10.1+/−0.3 degrees, 14.3+/−0.3 degrees, 17.5+/−0.3 degrees, 18.7+/−0.3 degrees, 20.6+/−0.3 degrees, 20.9+/−0.3 degrees, 21.8+/−0.3 degrees, 22.0+/−0.3 degrees, 23.3+/−0.3 degrees and 23.6+/−0.3 degrees 2-theta. In still another embodiment, Polymorph A exhibits an X-ray powder diffraction pattern having at least 9 characteristic peaks expressed in degrees 2-theta at about 3.9+/−0.3 degrees, 10.1+/−0.3 degrees, 14.3+/−0.3 degrees, 17.5+/−0.3 degrees, 18.7+/−0.3 degrees, 20.6+/−0.3 degrees, 20.9+/−0.3 degrees, 21.8+/−0.3 degrees, 22.0+/−0.3 degrees, 23.3+/−0.3 degrees and 23.6+/−0.3 degrees 2-theta. In yet another embodiment, the polymorph exhibits an X-ray powder diffraction pattern having at least 10 characteristic peaks expressed in degrees 2-theta at about 3.9+/−0.3 degrees, 10.1+/−0.3 degrees, 14.3+/−0.3 degrees, 17.5+/−0.3 degrees, 18.7+/−0.3 degrees, 20.6+/−0.3 degrees, 20.9+/−0.3 degrees, 21.8+/−0.3 degrees, 22.0+/−0.3 degrees, 23.3+/−0.3 degrees and 23.6+/−0.3 degrees 2-theta.

In still another embodiment, the polymorph exhibits an X-ray powder diffraction pattern having characteristic peaks expressed in degrees 2-theta at about 3.9+/−0.3 degrees, about 14.3+/−0.3 degrees, about 18.7+/−0.3 degrees, about 23.3+/−0.3 degrees, and about 23.6+/−0.3 degrees 2-theta.

In still another embodiment, the polymorph exhibits an X-ray powder diffraction pattern having characteristic peaks expressed in degrees 2-theta at about 3.9+/−0.3 degrees, about 10.1+/−0.3 degrees, about 14.3+/−0.3 degrees, about 17.5+/−0.3 degrees, about 18.7+/−0.3 degrees, about 20.6+/−0.3 degrees, about 20.9+/−0.3 degrees, about 21.8+/−0.3 degrees, about 22.0+/−0.3 degrees, about 23.3+/−0.3 degrees and about 23.6+/−0.3 degrees 2-theta. In yet another embodiment, the polymorph exhibits an X-ray powder diffraction pattern substantially in accordance with FIG. 1. In another embodiment, the polymorph exhibits an X-ray powder diffraction pattern substantially in accordance with the 2-theta values listed in Table 1.

As used herein, the term "about", when used in reference to a degree 2-theta value refers to the stated value +/−0.3 degrees 2-theta.

Pharmaceutical compositions comprising Polymorph A can be identified by comparison of the compositions' X-ray powder diffraction patterns to an X-ray powder diffraction pattern of Polymorph A. It will be appreciated that pharmaceutical compositions comprising Polymorph A may exhibit non-identical X-ray powder diffraction patterns as compared to an X-ray powder diffraction pattern of pure Polymorph A.

In certain embodiments, Polymorph A is identifiable on the basis of a characteristic peak observed in a differential scanning calorimetry thermogram. Differential scanning calorimetry, or DSC, is a thermoanalytical technique in which the difference in the amount of heat required to increase the temperature of a sample and reference is measured as a function of temperature. In one embodiment, Polymorph A exhibits a differential scanning calorimetry thermogram having a characteristic peak expressed in units of ° C. at a temperature of about 255+/−5° C. In another embodiment, Polymorph A exhibits a differential scanning calorimetry thermogram having a single endothermic peak observed at the temperature range of 250-255° C. In another embodiment, Polymorph A exhibits a differential scanning calorimetry thermogram substantially in accordance with FIG. 3.

In certain embodiments, Polymorph A may contain impurities. Non-limiting examples of impurities include undesired polymorph forms, or residual organic and inorganic molecules such as solvents, water or salts. In one embodiment, Polymorph A is substantially free from impurities. In another embodiment, Polymorph A contains less than 10% by weight total impurities. In another embodiment, Polymorph A contains less than 5% by weight total impurities. In another embodiment, Polymorph A contains less than 1% by weight total impurities. In yet another embodiment, Polymorph A contains less than 0.1% by weight total impurities.

In certain embodiments, Polymorph A is a crystalline solid substantially free of amorphous Compound I hydrobromide. As used herein, the term "substantially free of amorphous Compound I hydrobromide" means that the compound contains no significant amount of amorphous Compound I hydrobromide. In certain embodiments, at least about 95% by weight of crystalline Polymorph A is present. In still other embodiments of the invention, at least about 99% by weight of crystalline Polymorph A is present.

In another embodiment, Polymorph A is substantially free from Polymorph B.

The salt of the invention, and its crystal form Polymorph A, can be found together with other substances or can be isolated. In some embodiments, the salt of the invention, or its crystal form, is substantially isolated. By "substantially isolated" is meant that the salt or its crystal form is at least partially or substantially separated from the environment in which it was formed or detected. Partial separation can include, for example, a composition enriched in the salt of the invention. Substantial separation can include compositions containing at least about 50%, at least about 60%, at least about 70%, at least about 80%, at least about 90%, at least about 95%, at least about 97%, or at least about 99% by weight of the hydrobromide of Compound I and Polymorph A. Methods for isolating compounds and their salts are routine in the art.

Both the hydrobromide of Compound I and Polymorph A can occur as any reasonable tautomer, or a mixture of reasonable tautomers. As used herein, "tautomer" refers to one of two or more structural isomers that exist in equilibrium and are readily converted from one isomeric form to another. Examples include keto-enol tautomers, such as acetone/propen-2-ol, and the like. The hydrobromide of Compound I and Polymorph A can have one or more tautomers and therefore include various isomers, i.e., pyridin-2(1H)-one and the corresponding pyridin-2-ol. All such isomeric forms of these compounds are expressly included in the present invention.

Preparation of HBr Salt Form and Polymorph A

The hydrobromide of Compound I, as well as Polymorph A, can be prepared using known techniques. Conventionally, a salt form is prepared by combining in solution the free base compound and an acid containing the anion of the salt form desired, and then isolating the solid salt product from the reaction solution (e.g., by crystallization, precipitation, evaporation, etc.). Other salt-forming techniques can be employed.

Scheme 1 below outlines a particular embodiment for the production of the free base of Compound I, as well as the hydrobromide of Compound I. Briefly, methyl 3-amino-5-bromo-2-methylbenzoate (1) is reacted with dihydro-2H-pyran-4(3H)-one under reductive amination conditions to form methyl 5-bromo-2-methyl-3-((tetrahydro-2H-pyran-4-yl)amino)benzoate (2) in step 1. In step 2, reductive amination is again used to form 5-bromo-3-(ethyl(tetrahydro-2H-pyran-4-yl)amino)-2-methylbenzoate (3). This compound is then reacted under Suzuki coupling conditions in step 3 to form methyl 5-(ethyl(tetrahydro-2H-pyran-4-yl)amino)-4-methyl-4'-(morpholinomethyl)-[1,1'-biphenyl]-3-carboxylate (4), which is hydrolyzed to the corresponding acid (5) in step 4. In step 5, acid (5) is reacted under amide coupling reaction conditions with 3-(aminomethyl)-4,6-dimethyl-dihydro-pyridin-2(1H)-one hydrochloride to form Compound I.

As shown, Compound I can then be reacted with aqueous HBr to form the hydrobromide of Compound I.

Figure 9:
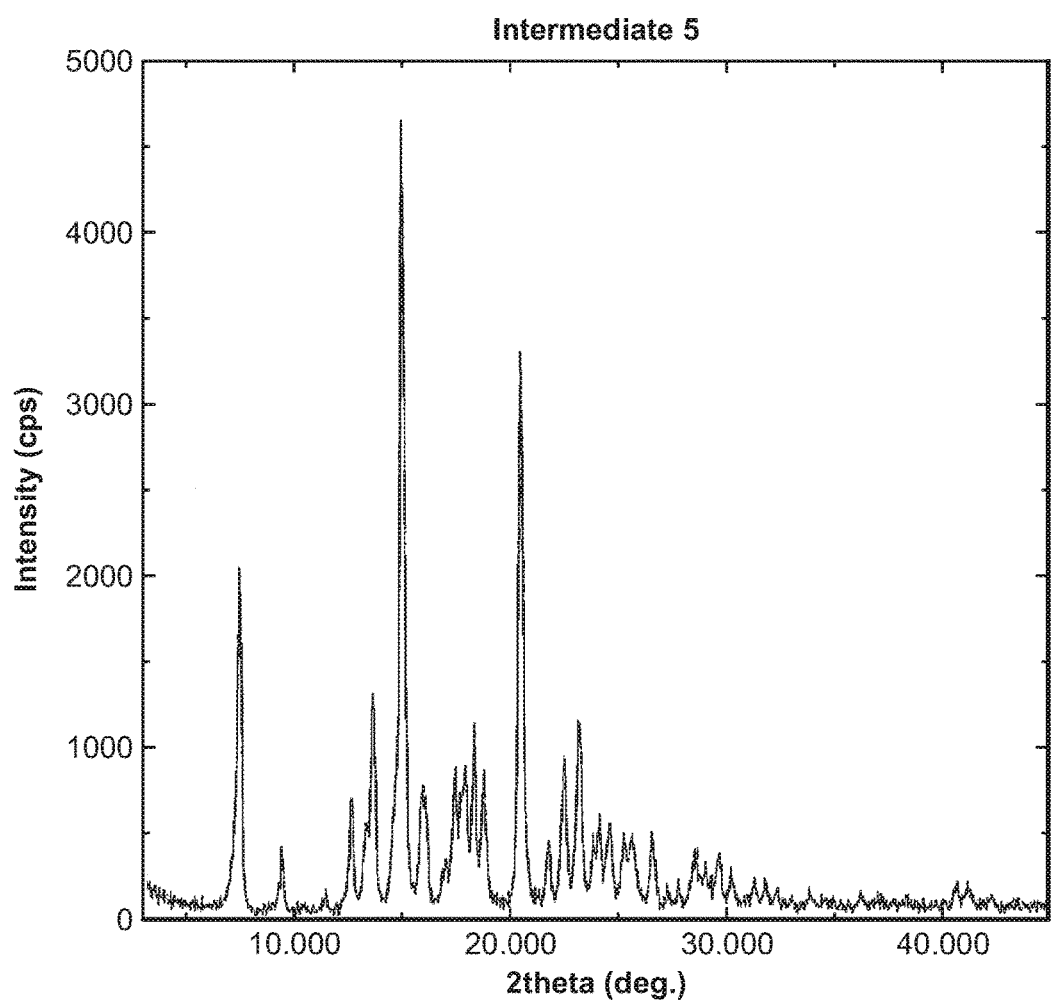
FIG. 9 depicts the X-ray powder diffraction pattern of synthetic intermediate 5.
Figure 17:
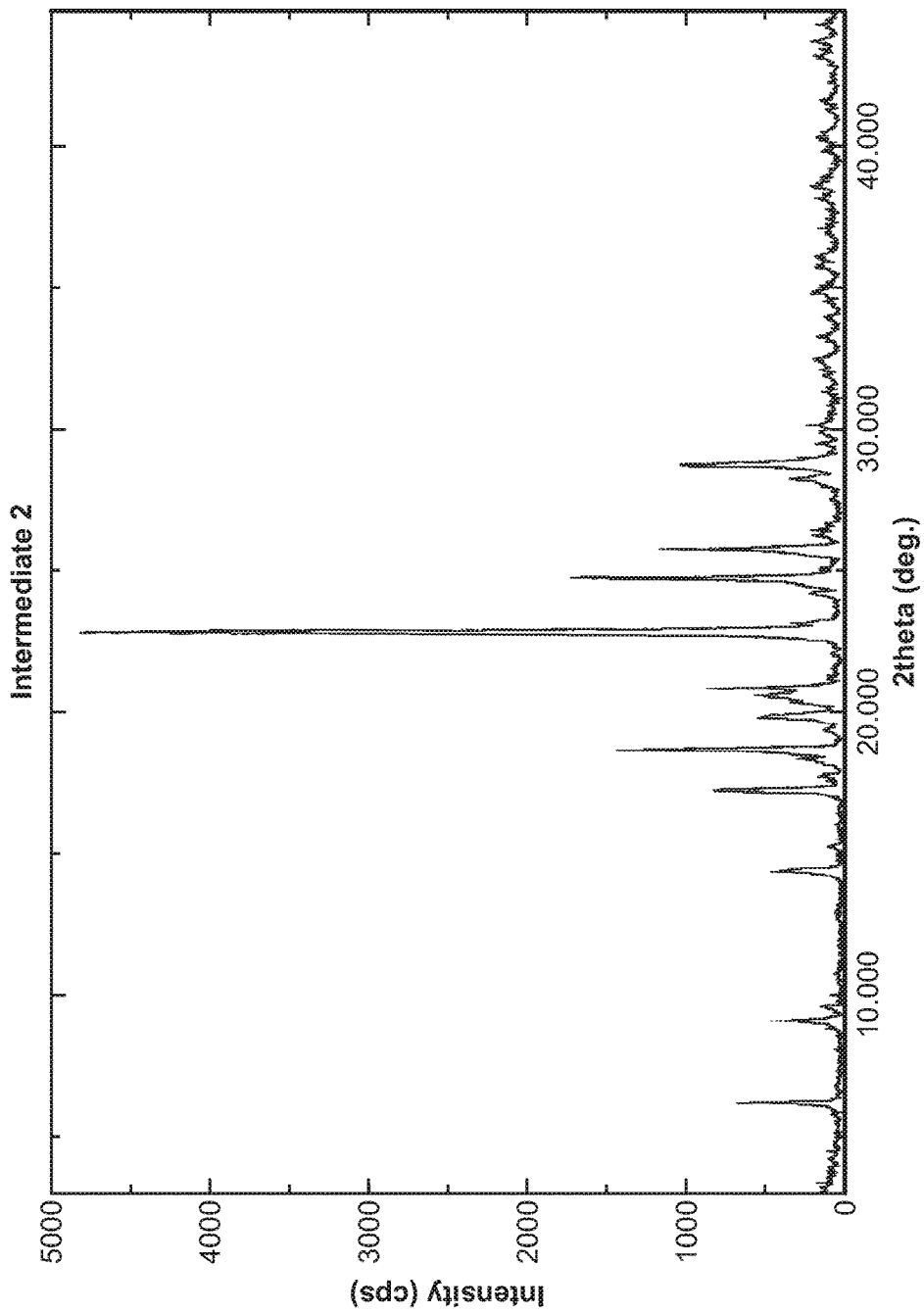
FIG. 17 depicts the X-ray powder diffraction pattern of synthetic intermediate 2.

Accordingly, provided herein is intermediate compound 1 in crystalline form. In another embodiment, provided herein is intermediate compound 2 in crystalline form. FIG. 17 shows an X-ray powder diffraction pattern of crystalline compound 2. In still another embodiment, the intermediate compound 5 is crystalline. FIG. 9 shows an X-ray powder diffraction pattern of crystalline compound 5. In other embodiments, compounds 2 and/or 5 are produced in substantially pure form without the use of chromatography. It will be appreciated by the skilled artisan that the crystallization of intermediates does not necessarily proceed effortlessly or efficiently.

Also provided herein is a method of preparing N-((4,6-dimethyl-2-oxo-1,2-dihydropyridin-3-yl)methyl)-5-(ethyl (tetrahydro-2H-pyran-4-yl)amino)-4-methyl-4'-(morpholinomethyl)-[1,1'-biphenyl]-3-carboxamide comprising reacting 5-(Ethyl(tetrahydro-2H-pyran-4-yl)amino)-4-methyl-4'-(morpholinomethyl)-[1,1'-biphenyl]-3-carboxylic acid (5) with a salt of 3-(aminomethyl)-4,6-dimethyl-dihydro-pyridin-2(1H)-one. In one embodiment of this method, (5) is in crystalline form.

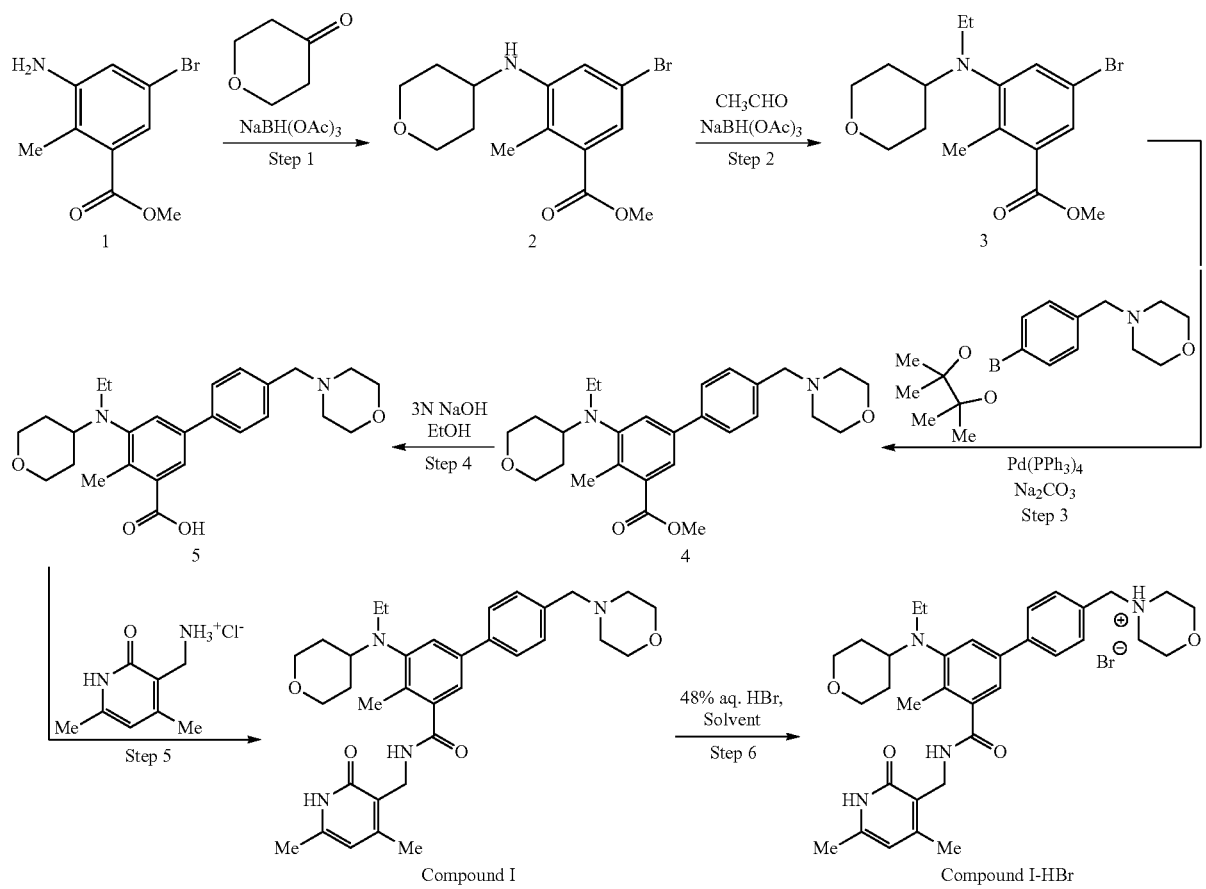

Scheme 1

The synthesis described above has a number of advantages. For example, it utilizes a number of intermediates that can be prepared in crystalline forms that can be isolated. By using crystalline intermediates, minimal purification techniques (e.g., chromatography) are necessary, leading to an overall improved yield of final Compound I.

Compound I can be reacted with aqueous HBr in the presence of an appropriate solvent to form Polymorph A, a particular crystal form of the hydrobromide. In an embodiment, Compound I is reacted with aqueous HBr in the presence of ethanol and ethyl acetate to form Polymorph A.

Once the polymorph is prepared, it can be recrystallized, using the same solvent (or solvents) that were used to prepare the polymorph, or a different solvent (or solvents), to produce a composition that has increased crystallinity. In general, Polymorph A can be recrystallized by dissolving the polymorph in one or more solvents, optionally heating, followed by an optional cooling step, and then isolating the crystal structure, through, e.g., a filtering step. After the polymorph is initially dissolved in the first solvent (or combination of solvents), an additional, different solvent can be added at any point in the process (before or after heating, before or after cooling, etc.) to produce the desired crystal structure. For example, a first solvent can be used to dissolve the polymorph compound, and then a second solvent (e.g., an anti-solvent) can be added to cause the polymorph to precipitate from solution. In an embodiment, water is added to the first solvent to aid in dissolving the polymorph.

Non-limiting examples of solvents that can be used for the recrystallization of Polymorph A are as follows: methanol, ethanol, ethyl acetate, methyl tert-butyl ether, water, isopropyl alcohol, tetrahydrofuran, acetone, acetonitrile, and 2-methyltetrahydrofuran, as well as combinations thereof. Non-limiting examples of solvent combinations that are useful for the recrystallization of Polymorph A are (solvent and anti-solvent, wherein water can be added to the first solvent to aid in dissolving the polymorph): methanol/water and ethyl acetate, isopropyl alcohol/water and ethyl acetate, tetrahydrofuran/water and ethyl acetate, acetone and ethyl acetate, acetonitrile/water and ethyl acetate, ethanol/water and methyl tert-butyl ether, isopropyl alcohol/water and methyl tert-butyl ether, ethanol/water and tetrahydrofuran, isopropyl alcohol/water and acetone, and ethanol/water and ethyl acetate. In particular embodiments, the solvent combinations are methanol/water and ethyl acetate, isopropyl alcohol/water and ethyl acetate, ethanol/water and 2-methyltetrahydrofuran, and methanol/2-methyltetrahydrofuran.

In one aspect, Polymorph A is prepared using a method comprising combining N-((4,6-dimethyl-2-oxo-1,2-dihydropyridin-3-yl)methyl)-5-(ethyl (tetrahydro-2H-pyran-4-yl)amino)-4-methyl-4'-(morpholinomethyl)-[1,1'-biphenyl]-3-carboxamide with hydrobromic acid.

In another aspect, provided herein is a method of recrystallizing Polymorph A, which comprises the following steps: (a) dissolving Polymorph A in a first solvent, and (b) adding a second solvent, such that said polymorph is recrystallized. In one embodiment, the first solvent is ethanol, and the second solvent is MTBE. In another embodiment, the method comprises (a) dissolving Polymorph A in ethanol, (b) heating the mixture, (c) adding MTBE to the mixture, forming a precipitate comprising said polymorph, and filtering the precipitate such that said polymorph is recrystallized.

Pharmaceutical Compositions

In another aspect, provided herein is a pharmaceutical composition comprising the hydrobromide of Compound I, and a pharmaceutically acceptable carrier or diluent. Also provided herein is a pharmaceutical composition comprising Polymorph A, and a pharmaceutically acceptable carrier or diluent.

The term "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1% to 99.9% (more preferably, 0.5 to 90%) of active ingredient in combination with a pharmaceutically acceptable carrier.

The compounds described herein (i.e., the hydrobromide of Compound I and Polymorph A) can be combined with a pharmaceutically acceptable carrier according to conventional pharmaceutical compounding techniques. As used herein, "pharmaceutically acceptable carrier" may include any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Furthermore, the carrier may take a wide variety of forms depending on the form of the preparation desired for administration, e.g. oral, nasal, rectal, vaginal, parenteral (including intravenous injections or infusions). In preparing compositions for oral dosage form any of the usual pharmaceutical media may be employed. Usual pharmaceutical media include, for example, water, glycols, oils, alcohols, flavoring agents, preservatives, coloring agents, and the like in the case of oral liquid preparations (such as for example, suspensions, solutions, emulsions and elixirs); aerosols; or carriers such as starches, sugars, microcrystalline cellulose, diluents, granulating agents, lubricants, binders, disintegrating agents and the like, in the case of oral solid preparations (such as for example, powders, capsules, and tablets).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, tocopherols, and the like; and metal chelating agents, such as citric acid, ethylenediamine tetraacetic acid (EDTA), sorbitol, tartaric acid, phosphoric acid, and the like.

Pharmaceutical compositions comprising the compounds may be formulated to have any concentration desired. In some embodiments, the composition is formulated such that it comprises at least a therapeutically effective amount. In some embodiments, the composition is formulated such that it comprises an amount that would not cause one or more unwanted side effects.

Because the crystalline form of the hydrobromide of Compound I is more easily maintained during its preparation, solid dosage forms are a preferred form for the pharmaceutical composition of the invention. Solid dosage forms for oral administration, such as capsules, tablets, pills, powders, and granules, are particularly preferred. If desired, tablets may be coated by techniques known to those in the art.

Pharmaceutical compositions include those suitable for oral, sublingual, nasal rectal, vaginal, topical, buccal and parenteral (including subcutaneous, intramuscular, and intravenous) administration, although the most suitable route will depend on the nature and severity of the condition being treated. The compositions may be conveniently presented in unit dosage form, and prepared by any of the methods well known in the art of pharmacy. In certain embodiments, the pharmaceutical composition is formulated for oral administration in the form of a pill, capsule, lozenge or tablet. In other embodiments, the pharmaceutical composition is in the form of a suspension.

The compounds provided herein are suitable as an active agent in pharmaceutical compositions that are efficacious particularly for treating EZH2-associated disorders, especially cancer. The pharmaceutical composition in various embodiments has a pharmaceutically effective amount of the hydrobromide of Compound I or Polymorph A, along with other pharmaceutically acceptable excipients, carriers, fillers, diluents and the like.

A therapeutically or pharmaceutically "effective amount" is an amount of a compound (the hydrobromide of Compound I or Polymorph A), that when administered to a patient, ameliorates a symptom of a disease or condition, e.g., prevent the various morphological and somatic symptoms of cancer. In an example, an effective amount of the hydrobromide of Compound I or Polymorph A is the amount sufficient to treat cancer in a subject. The amount can vary depending on such factors as the size and weight of the subject, the type of illness, or the particular compound of the invention. The amount of the hydrobromide of Compound I or Polymorph A that constitutes an "effective amount" will vary depending on the compound, the disease state and its severity, the age of the patient to be treated, and the like. The effective amount can be determined routinely by one of ordinary skill in the art having regard to their knowledge and to this disclosure.

The regimen of administration can affect what constitutes a pharmaceutically effective amount. The hydrobromide of Compound I or Polymorph A, and compositions comprising either of these compounds, can be administered to the subject either prior to or after the onset of a disease. Further, several divided dosages, as well as staggered dosages can be administered daily or sequentially, or the dose can be continuously infused, or can be a bolus injection. Further, the dosages can be proportionally increased or decreased as indicated by the exigencies of the therapeutic or prophylactic situation.

Methods of Treatment

Compounds of the present invention (i.e., the hydrobromide of Compound I, as well as Polymorph A) inhibit the histone methyltransferase activity of EZH2 or a mutant thereof and, accordingly, in one aspect of the invention, certain compounds disclosed herein are candidates for treating, or preventing certain conditions and diseases. The present invention provides methods for treating conditions and diseases the course of which can be influenced by modulating the methylation status of histones or other proteins, wherein said methylation status is mediated at least in part by the activity of EZH2. Modulation of the methylation status of histones can in turn influence the level of expression of target genes activated by methylation, and/or target genes suppressed by methylation. The method includes administering to a subject in need of such treatment, a therapeutically effective amount of a compound of the present invention.

The disorder in which EZH2-mediated protein methylation plays a part can be cancer or a precancerous condition. The present invention further provides the use of a compound of the present invention (i.e., the hydrobromide of Compound I, as well as Polymorph A) in the treatment of cancer or precancer the course of which can be influenced by modulating EZH2-mediated protein methylation, or, for the preparation of a medicament useful for the treatment of such cancer or pre-cancer. Exemplary cancers that may be treated include lymphomas, including non-Hodgkin lymphoma, follicular lymphoma (FL) and diffuse large B-cell lymphoma (DLBCL); melanoma; and leukemia, including CML. Exemplary precancerous condition includes myelodysplastic syndrome (MDS; formerly known as preleukemia).

In still another embodiment, provided herein is a method of treating a lymphoma comprising administering to the subject in need thereof an effective amount of the hydrobromide of Compound I.

In yet another embodiment, provided herein is a method of treating a lymphoma comprising administering to a subject in need thereof an effective amount of Polymorph A.

The present invention also provides methods of protecting against a disorder in which EZH2-mediated protein methylation plays a part in a subject in need thereof by administering a therapeutically effective amount of compound of the present invention (i.e., the hydrobromide of Compound I, as well as Polymorph A) to a subject in need of such treatment. The disorder can be cancer, e.g., cancer in which EZH2-mediated protein methylation plays a role. The present invention also provides the use of compound of the present invention (i.e., the hydrobromide of Compound I, as well as Polymorph A) for the preparation of a medicament useful for the prevention of a cell proliferative disorder associated, at least in part, with EZH2-mediated protein methylation.

The compounds of this invention can be used to modulate protein (e.g., histone) methylation, e.g., to modulate histone methyltransferase or histone demethylase enzyme activity. At least some of the compounds of the invention can be used in vivo or in vitro for modulating protein methylation. Histone methylation has been reported to be involved in aberrant expression of certain genes in cancers, and in silencing of neuronal genes in non-neuronal cells. At least some compounds described herein are suitable candidates for treating these diseases, i.e., to decreases methylation or restores methylation to roughly its level in counterpart normal cells.

Compounds that are methylation modulators may be used for modulating cell proliferation. For example, in some cases excessive proliferation may be reduced with agents that decrease methylation, whereas insufficient proliferation may be stimulated with agents that increase methylation.

Accordingly, diseases that may be treated by the compounds of the invention can include hyperproliferative diseases, such as benign cell growth and malignant cell growth.

As used herein, a "subject in need thereof" is a subject having a disorder in which EZH2-mediated protein methylation plays a part, or a subject having an increased risk of developing such disorder relative to the population at large. A subject in need thereof can have a precancerous condition. Preferably, a subject in need thereof has cancer. A "subject" includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human.

As used herein, the term "cell proliferative disorder" refers to conditions in which unregulated or abnormal growth, or both, of cells can lead to the development of an unwanted condition or disease, which may or may not be cancerous. Exemplary cell proliferative disorders that may be treated with the compounds of the invention encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer. In one aspect, the methods provided herein are used to treat or alleviate a symptom of cancer or to identify suitable candidates for such purposes. The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

Exemplary non-cancerous conditions or disorders that may be treated using one or more compounds of the present invention include, but are not limited to, rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus.

Exemplary cancers that can be treated using one or more compounds of the present invention include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

A "cell proliferative disorder of the hematologic system" is a cell proliferative disorder involving cells of the hematologic system. A cell proliferative disorder of the hematologic system can include lymphoma, leukemia, myeloid neoplasms, mast cell neoplasms, myelodysplasia, benign monoclonal gammopathy, lymphomatoid granulomatosis, lymphomatoid papulosis, polycythemia vera, chronic myelocytic leukemia, agnogenic myeloid metaplasia, and essential thrombocythemia. A cell proliferative disorder of the hematologic system can include hyperplasia, dysplasia, and metaplasia of cells of the hematologic system. In one aspect, compositions of the present invention may be used to treat a cancer selected from the group consisting of a hematologic cancer of the present invention or a hematologic cell proliferative disorder of the present invention, or used to identify suitable candidates for such purposes. A hematologic cancer of the present invention can include multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia), myeloid neoplasms and mast cell neoplasms.

A "cell proliferative disorder of the lung" is a cell proliferative disorder involving cells of the lung. Cell proliferative disorders of the lung can include all forms of cell proliferative disorders affecting lung cells. Cell proliferative disorders of the lung can include lung cancer, a precancer or precancerous condition of the lung, benign growths or lesions of the lung, and malignant growths or lesions of the lung, and metastatic lesions in tissue and organs in the body other than the lung. In one aspect, compositions of the present invention may be used to treat lung cancer or cell proliferative disorders of the lung, or used to identify suitable candidates for such purposes. Lung cancer can include all forms of cancer of the lung. Lung cancer can include malignant lung neoplasms, carcinoma in situ, typical carcinoid tumors, and atypical carcinoid tumors. Lung cancer can include small cell lung cancer ("SCLC"), non-small cell lung cancer ("NSCLC"), squamous cell carcinoma, adenocarcinoma, small cell carcinoma, large cell carcinoma, adenosquamous cell carcinoma, and mesothelioma. Lung cancer can include "scar carcinoma," bronchioalveolar carcinoma, giant cell carcinoma, spindle cell carcinoma, and large cell neuroendocrine carcinoma. Lung cancer can include lung neoplasms having histologic and ultrastructual heterogeneity (e.g., mixed cell types).

Cell proliferative disorders of the lung can include all forms of cell proliferative disorders affecting lung cells. Cell proliferative disorders of the lung can include lung cancer, precancerous conditions of the lung. Cell proliferative disorders of the lung can include hyperplasia, metaplasia, and dysplasia of the lung. Cell proliferative disorders of the lung can include asbestos-induced hyperplasia, squamous metaplasia, and benign reactive mesothelial metaplasia. Cell proliferative disorders of the lung can include replacement of columnar epithelium with stratified squamous epithelium, and mucosal dysplasia. Individuals exposed to inhaled injurious environmental agents such as cigarette smoke and asbestos may be at increased risk for developing cell proliferative disorders of the lung. Prior lung diseases that may predispose individuals to development of cell proliferative disorders of the lung can include chronic interstitial lung disease, necrotizing pulmonary disease, scleroderma, rheumatoid disease, sarcoidosis, interstitial pneumonitis, tuberculosis, repeated pneumonias, idiopathic pulmonary fibrosis, granulomata, asbestosis, fibrosing alveolitis, and Hodgkin's disease.

A "cell proliferative disorder of the colon" is a cell proliferative disorder involving cells of the colon. Preferably, the cell proliferative disorder of the colon is colon cancer. In one aspect, compositions of the present invention may be used to treat colon cancer or cell proliferative disorders of the colon, or used to identify suitable candidates for such purposes. Colon cancer can include all forms of cancer of the colon. Colon cancer can include sporadic and hereditary colon cancers. Colon cancer can include malignant colon neoplasms, carcinoma in situ, typical carcinoid tumors, and atypical carcinoid tumors. Colon cancer can include adenocarcinoma, squamous cell carcinoma, and adenosquamous cell carcinoma. Colon cancer can be associated with a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis. Colon cancer can be caused by a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis.

Cell proliferative disorders of the colon can include all forms of cell proliferative disorders affecting colon cells. Cell proliferative disorders of the colon can include colon cancer, precancerous conditions of the colon, adenomatous polyps of the colon and metachronous lesions of the colon. A cell proliferative disorder of the colon can include adenoma. Cell proliferative disorders of the colon can be characterized by hyperplasia, metaplasia, and dysplasia of the colon. Prior colon diseases that may predispose individuals to development of cell proliferative disorders of the colon can include prior colon cancer. Current disease that may predispose individuals to development of cell proliferative disorders of the colon can include Crohn's disease and ulcerative colitis. A cell proliferative disorder of the colon can be associated with a mutation in a gene selected from the group consisting of p53, ras, FAP and DCC. An individual can have an elevated risk of developing a cell proliferative disorder of the colon due to the presence of a mutation in a gene selected from the group consisting of p53, ras, FAP and DCC.

A "cell proliferative disorder of the pancreas" is a cell proliferative disorder involving cells of the pancreas. Cell proliferative disorders of the pancreas can include all forms of cell proliferative disorders affecting pancreatic cells. Cell proliferative disorders of the pancreas can include pancreas cancer, a precancer or precancerous condition of the pancreas, hyperplasia of the pancreas, and dysaplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas. Pancreatic cancer can include ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma. Pancreatic cancer can also include pancreatic neoplasms having histologic and ultrastructual heterogeneity (e.g., mixed cell types).

A "cell proliferative disorder of the prostate" is a cell proliferative disorder involving cells of the prostate. Cell proliferative disorders of the prostate can include all forms of cell proliferative disorders affecting prostate cells. Cell proliferative disorders of the prostate can include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate can include hyperplasia, metaplasia, and dysplasia of the prostate.

A "cell proliferative disorder of the skin" is a cell proliferative disorder involving cells of the skin. Cell proliferative disorders of the skin can include all forms of cell proliferative disorders affecting skin cells. Cell proliferative disorders of the skin can include a precancer or precancerous condition of the skin, benign growths or lesions of the skin, melanoma, malignant melanoma and other malignant growths or lesions of the skin, and metastatic lesions in tissue and organs in the body other than the skin. Cell proliferative disorders of the skin can include hyperplasia, metaplasia, and dysplasia of the skin.

A "cell proliferative disorder of the ovary" is a cell proliferative disorder involving cells of the ovary. Cell proliferative disorders of the ovary can include all forms of cell proliferative disorders affecting cells of the ovary. Cell proliferative disorders of the ovary can include a precancer or precancerous condition of the ovary, benign growths or lesions of the ovary, ovarian cancer, malignant growths or lesions of the ovary, and metastatic lesions in tissue and organs in the body other than the ovary. Cell proliferative disorders of the skin can include hyperplasia, metaplasia, and dysplasia of cells of the ovary.

A "cell proliferative disorder of the breast" is a cell proliferative disorder involving cells of the breast. Cell proliferative disorders of the breast can include all forms of cell proliferative disorders affecting breast cells. Cell proliferative disorders of the breast can include breast cancer, a precancer or precancerous condition of the breast, benign growths or lesions of the breast, and malignant growths or lesions of the breast, and metastatic lesions in tissue and organs in the body other than the breast. Cell proliferative disorders of the breast can include hyperplasia, metaplasia, and dysplasia of the breast.

A cell proliferative disorder of the breast can be a precancerous condition of the breast. Compositions of the present invention may be used to treat a precancerous condition of the breast. A precancerous condition of the breast can include atypical hyperplasia of the breast, ductal carcinoma in situ (DCIS), intraductal carcinoma, lobular carcinoma in situ (LCIS), lobular neoplasia, and stage 0 or grade 0 growth or lesion of the breast (e.g., stage 0 or grade 0 breast cancer, or carcinoma in situ). A precancerous condition of the breast can be staged according to the TNM classification scheme as accepted by the American Joint Committee on Cancer (AJCC), where the primary tumor (T) has been assigned a stage of T0 or Tis; and where the regional lymph nodes (N) have been assigned a stage of N0; and where distant metastasis (M) has been assigned a stage of M0.

The cell proliferative disorder of the breast can be breast cancer. In one aspect, compositions of the present invention may be used to treat breast cancer, or used to identify suitable candidates for such purposes. Breast cancer may include all forms of cancer of the breast. Breast cancer can include primary epithelial breast cancers. Breast cancer can include cancers in which the breast is involved by other tumors such as lymphoma, sarcoma or melanoma. Breast cancer can include carcinoma of the breast, ductal carcinoma of the breast, lobular carcinoma of the breast, undifferentiated carcinoma of the breast, cystosarcoma phyllodes of the breast, angiosarcoma of the breast, and primary lymphoma of the breast. Breast cancer can include Stage I, II, IIIA, IIIB, IIIC and IV breast cancer. Ductal carcinoma of the breast can include invasive carcinoma, invasive carcinoma in situ with predominant intraductal component, inflammatory breast cancer, and a ductal carcinoma of the breast with a histologic type selected from the group consisting of comedo, mucinous (colloid), medullary, medullary with lymphcytic infiltrate, papillary, scirrhous, and tubular. Lobular carcinoma of the breast can include invasive lobular carcinoma with predominant in situ component, invasive lobular carcinoma, and infiltrating lobular carcinoma. Breast cancer can include Paget's disease, Paget's disease with intraductal carcinoma, and Paget's disease with invasive ductal carcinoma. Breast cancer can include breast neoplasms having histologic and ultrastructual heterogeneity (e.g., mixed cell types).

Compounds of the present invention can be used to treat breast cancer, or used to identify suitable candidates for such purposes. A breast cancer that is to be treated can include familial breast cancer. A breast cancer that is to be treated can include sporadic breast cancer. A breast cancer that is to be treated can arise in a male subject. A breast cancer that is to be treated can arise in a female subject. A breast cancer that is to be treated can arise in a premenopausal female subject or a postmenopausal female subject. A breast cancer that is to be treated can arise in a subject equal to or older than 30 years old, or a subject younger than 30 years old. A breast cancer that is to be treated has arisen in a subject equal to or older than 50 years old, or a subject younger than 50 years old. A breast cancer that is to be treated can arise in a subject equal to or older than 70 years old, or a subject younger than 70 years old.

A breast cancer that is to be treated can be typed to identify a familial or spontaneous mutation in BRCA1, BRCA2, or p53. A breast cancer that is to be treated can be typed as having a HER2/neu gene amplification, as overexpressing HER2/neu, or as having a low, intermediate or high level of HER2/neu expression. A breast cancer that is to be treated can be typed for a marker selected from the group consisting of estrogen receptor (ER), progesterone receptor (PR), human epidermal growth factor receptor-2, Ki-67, CA15-3, CA 27-29, and c-Met. A breast cancer that is to be treated can be typed as ER-unknown, ER-rich or ER-poor. A breast cancer that is to be treated can be typed as ER-negative or ER-positive. ER-typing of a breast cancer may be performed by any reproducible means. ER-typing of a breast cancer may be performed as set forth in Onkologie 27: 175-179 (2004). A breast cancer that is to be treated can be typed as PR-unknown, PR-rich, or PR-poor. A breast cancer that is to be treated can be typed as PR-negative or PR-positive. A breast cancer that is to be treated can be typed as receptor positive or receptor negative. A breast cancer that is to be treated can be typed as being associated with elevated blood levels of CA 15-3, or CA 27-29, or both.

A breast cancer that is to be treated can include a localized tumor of the breast. A breast cancer that is to be treated can include a tumor of the breast that is associated with a negative sentinel lymph node (SLN) biopsy. A breast cancer that is to be treated can include a tumor of the breast that is associated with a positive sentinel lymph node (SLN) biopsy. A breast cancer that is to be treated can include a tumor of the breast that is associated with one or more positive axillary lymph nodes, where the axillary lymph nodes have been staged by any applicable method. A breast cancer that is to be treated can include a tumor of the breast that has been typed as having nodal negative status (e.g., node-negative) or nodal positive status (e.g., node-positive). A breast cancer that is to be treated can include a tumor of the breast that has metastasized to other locations in the body. A breast cancer that is to be treated can be classified as having metastasized to a location selected from the group consisting of bone, lung, liver, or brain. A breast cancer that is to be treated can be classified according to a characteristic selected from the group consisting of metastatic, localized, regional, local-regional, locally advanced, distant, multicentric, bilateral, ipsilateral, contralateral, newly diagnosed, recurrent, and inoperable.

A compound of the present invention may be used to treat or prevent a cell proliferative disorder of the breast, or to treat or prevent breast cancer, in a subject having an increased risk of developing breast cancer relative to the population at large, or used to identify suitable candidates for such purposes. A subject with an increased risk of developing breast cancer relative to the population at large is a female subject with a family history or personal history of breast cancer. A subject with an increased risk of developing breast cancer relative to the population at large is a female subject having a germ-line or spontaneous mutation in BRCA1 or BRCA2, or both. A subject with an increased risk of developing breast cancer relative to the population at large is a female subject with a family history of breast cancer and a germ-line or spontaneous mutation in BRCA1 or BRCA2, or both. A subject with an increased risk of developing breast cancer relative to the population at large is a female who is greater than 30 years old, greater than 40 years old, greater than 50 years old, greater than 60 years old, greater than 70 years old, greater than 80 years old, or greater than 90 years old. A subject with an increased risk of developing breast cancer relative to the population at large is a subject with atypical hyperplasia of the breast, ductal carcinoma in situ (DCIS), intraductal carcinoma, lobular carcinoma in situ (LCIS), lobular neoplasia, or a stage 0 growth or lesion of the breast (e.g., stage 0 or grade 0 breast cancer, or carcinoma in situ).

A breast cancer that is to be treated can be histologically graded according to the Scarff-Bloom-Richardson system, wherein a breast tumor has been assigned a mitosis count score of 1, 2, or 3; a nuclear pleiomorphism score of 1, 2, or 3; a tubule formation score of 1, 2, or 3; and a total Scarff-Bloom-Richardson score of between 3 and 9. A breast cancer that is to be treated can be assigned a tumor grade according to the International Consensus Panel on the Treatment of Breast Cancer selected from the group consisting of grade 1, grade 1-2, grade 2, grade 2-3, or grade 3.

In one embodiment, provided herein is a method of treating breast cancer comprising administering to a subject in need thereof an effective amount of the hydrobromide of Compound I.

In another embodiment, provided herein is a method of treating breast cancer comprising administering to a subject in need thereof an effective amount of Polymorph A.

A cancer that is to be treated can be staged according to the American Joint Committee on Cancer (AJCC) TNM classification system, where the tumor (T) has been assigned a stage of TX, T1, T1mic, T1a, T1b, T1c, T2, T3, T4, T4a, T4b, T4c, or T4d; and where the regional lymph nodes (N) have been assigned a stage of NX, N0, N1, N2, N2a, N2b, N3, N3a, N3b, or N3c; and where distant metastasis (M) can be assigned a stage of MX, M0, or M1. A cancer that is to be treated can be staged according to an American Joint Committee on Cancer (AJCC) classification as Stage I, Stage IIA, Stage IIB, Stage IIIA, Stage IIIB, Stage IIIC, or Stage IV. A cancer that is to be treated can be assigned a grade according to an AJCC classification as Grade GX (e.g., grade cannot be assessed), Grade 1, Grade 2, Grade 3 or Grade 4. A cancer that is to be treated can be staged according to an AJCC pathologic classification (pN) of pNX, pN0, PN0 (I−), PN0 (I+), PN0 (mol−), PN0 (mol+), PN1, PN1(mi), PN1a, PN1b, PN1c, pN2, pN2a, pN2b, pN3, pN3a, pN3b, or pN3c.

A cancer that is to be treated can include a tumor that has been determined to be less than or equal to about 2 centimeters in diameter. A cancer that is to be treated can include a tumor that has been determined to be from about 2 to about 5 centimeters in diameter. A cancer that is to be treated can include a tumor that has been determined to be greater than or equal to about 3 centimeters in diameter. A cancer that is to be treated can include a tumor that has been determined to be greater than 5 centimeters in diameter. A cancer that is to be treated can be classified by microscopic appearance as well differentiated, moderately differentiated, poorly differentiated, or undifferentiated. A cancer that is to be treated can be classified by microscopic appearance with respect to mitosis count (e.g., amount of cell division) or nuclear pleiomorphism (e.g., change in cells). A cancer that is to be treated can be classified by microscopic appearance as being associated with areas of necrosis (e.g., areas of dying or degenerating cells). A cancer that is to be treated can be classified as having an abnormal karyotype, having an abnormal number of chromosomes, or having one or more chromosomes that are abnormal in appearance. A cancer that is to be treated can be classified as being aneuploid, triploid, tetraploid, or as having an altered ploidy. A cancer that is to be treated can be classified as having a chromosomal translocation, or a deletion or duplication of an entire chromosome, or a region of deletion, duplication or amplification of a portion of a chromosome.

A cancer that is to be treated can be evaluated by DNA cytometry, flow cytometry, or image cytometry. A cancer that is to be treated can be typed as having 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

As used herein, a "normal cell" is a cell that cannot be classified as part of a "cell proliferative disorder". A normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "candidate compound" refers to a compound of the present invention (i.e., the hydrobromide of Compound I, as well as Polymorph A) that has been or will be tested in one or more in vitro or in vivo biological assays, in order to determine if that compound is likely to elicit a desired biological or medical response in a cell, tissue, system, animal or human that is being sought by a researcher or clinician. A candidate compound is a compound of the present invention. The biological or medical response can be the treatment of cancer. The biological or medical response can be treatment or prevention of a cell proliferative disorder. The biological response or effect can also include a change in cell proliferation or growth that occurs in vitro or in an animal model, as well as other biological changes that are observable in vitro. In vitro or in vivo biological assays can include, but are not limited to, enzymatic activity assays, electrophoretic mobility shift assays, reporter gene assays, in vitro cell viability assays, and the assays described herein.

As used herein, "monotherapy" refers to the administration of a single active or therapeutic compound to a subject in need thereof. Preferably, monotherapy will involve administration of a therapeutically effective amount of an active compound. For example, cancer monotherapy with one of the compound of the present invention (i.e., the hydrobromide of Compound I, as well as Polymorph A) to a subject in need of treatment of cancer. Monotherapy may be contrasted with combination therapy, in which a combination of multiple active compounds is administered, preferably with each component of the combination present in a therapeutically effective amount. In one aspect, monotherapy with a compound of the present invention is more effective than combination therapy in inducing a desired biological effect.

As used herein, "treating" or "treat" describes the management and care of a patient for the purpose of combating a disease, condition, or disorder and includes the administration of a compound of the present invention (i.e., the hydrobromide of Compound I, as well as Polymorph A) to alleviate the symptoms or complications of a disease, condition or disorder, or to eliminate the disease, condition or disorder. The term "treat" can also include treatment of a cell in vitro or an animal model.

A compound of the present invention (i.e., the hydrobromide of Compound I, as well as Polymorph A) can also be used to prevent a disease, condition or disorder, or used to identify suitable candidates for such purposes. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions of the invention leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute, www.cancer.gov). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer. Severity also describes a histologic grade, also called differentiation, which refers to how much the tumor cells resemble normal cells of the same tissue type (see, National Cancer Institute, www.cancer.gov). Furthermore, severity describes a nuclear grade, which refers to the size and shape of the nucleus in tumor cells and the percentage of tumor cells that are dividing (see, National Cancer Institute, www.cancer.gov).

In another aspect of the invention, severity describes the degree to which a tumor has secreted growth factors, degraded the extracellular matrix, become vascularized, lost adhesion to juxtaposed tissues, or metastasized. Moreover, severity describes the number of locations to which a primary tumor has metastasized. Finally, severity includes the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/nuclear grade are considered alleviating a sign or symptom of the cancer.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body.

As a cancer grows, it begins to push on nearby organs, blood vessels, and nerves. This pressure creates some of the signs and symptoms of cancer. If the cancer is in a critical area, such as certain parts of the brain, even the smallest tumor can cause early symptoms.

But sometimes cancers start in places where it does not cause any symptoms until the cancer has grown quite large. Pancreas cancers, for example, do not usually grow large enough to be felt from the outside of the body. Some pancreatic cancers do not cause symptoms until they begin to grow around nearby nerves (this causes a backache). Others grow around the bile duct, which blocks the flow of bile and leads to a yellowing of the skin known as jaundice. By the time a pancreatic cancer causes these signs or symptoms, it has usually reached an advanced stage.

A cancer may also cause symptoms such as fever, fatigue, or weight loss. This may be because cancer cells use up much of the body's energy supply or release substances that change the body's metabolism. Or the cancer may cause the immune system to react in ways that produce these symptoms.

Sometimes, cancer cells release substances into the bloodstream that cause symptoms not usually thought to result from cancers. For example, some cancers of the pancreas can release substances which cause blood clots to develop in veins of the legs. Some lung cancers make hormone-like substances that affect blood calcium levels, affecting nerves and muscles and causing weakness and dizziness Cancer presents several general signs or symptoms that occur when a variety of subtypes of cancer cells are present. Most people with cancer will lose weight at some time with their disease. An unexplained (unintentional) weight loss of 10 pounds or more may be the first sign of cancer, particularly cancers of the pancreas, stomach, esophagus, or lung.

Fever is very common with cancer, but is more often seen in advanced disease. Almost all patients with cancer will have fever at some time, especially if the cancer or its treatment affects the immune system and makes it harder for the body to fight infection. Less often, fever may be an early sign of cancer, such as with leukemia or lymphoma.

Fatigue may be an important symptom as cancer progresses. It may happen early, though, in cancers such as with leukemia, or if the cancer is causing an ongoing loss of blood, as in some colon or stomach cancers.

Pain may be an early symptom with some cancers such as bone cancers or testicular cancer. But most often pain is a symptom of advanced disease.

Along with cancers of the skin (see next section), some internal cancers can cause skin signs that can be seen. These changes include the skin looking darker (hyperpigmentation), yellow (jaundice), or red (erythema); itching; or excessive hair growth.

Alternatively, or in addition, cancer subtypes present specific signs or symptoms. Changes in bowel habits or bladder function could indicate cancer. Long-term constipation, diarrhea, or a change in the size of the stool may be a sign of colon cancer. Pain with urination, blood in the urine, or a change in bladder function (such as more frequent or less frequent urination) could be related to bladder or prostate cancer.

Changes in skin condition or appearance of a new skin condition could indicate cancer. Skin cancers may bleed and look like sores that do not heal. A long-lasting sore in the mouth could be an oral cancer, especially in patients who smoke, chew tobacco, or frequently drink alcohol. Sores on the penis or vagina may either be signs of infection or an early cancer.

Unusual bleeding or discharge could indicate cancer. Unusual bleeding can happen in either early or advanced cancer. Blood in the sputum (phlegm) may be a sign of lung cancer. Blood in the stool (or a dark or black stool) could be a sign of colon or rectal cancer. Cancer of the cervix or the endometrium (lining of the uterus) can cause vaginal bleeding. Blood in the urine may be a sign of bladder or kidney cancer. A bloody discharge from the nipple may be a sign of breast cancer.

A thickening or lump in the breast or in other parts of the body could indicate the presence of a cancer. Many cancers can be felt through the skin, mostly in the breast, testicle, lymph nodes (glands), and the soft tissues of the body. A lump or thickening may be an early or late sign of cancer. Any lump or thickening could be indicative of cancer, especially if the formation is new or has grown in size.

Indigestion or trouble swallowing could indicate cancer. While these symptoms commonly have other causes, indigestion or swallowing problems may be a sign of cancer of the esophagus, stomach, or pharynx (throat).

Recent changes in a wart or mole could be indicative of cancer. Any wart, mole, or freckle that changes in color, size, or shape, or loses its definite borders indicates the potential development of cancer. For example, the skin lesion may be a melanoma.

A persistent cough or hoarseness could be indicative of cancer. A cough that does not go away may be a sign of lung cancer. Hoarseness can be a sign of cancer of the larynx (voice box) or thyroid.

While the signs and symptoms listed above are the more common ones seen with cancer, there are many others that are less common and are not listed here. However, all art-recognized signs and symptoms of cancer are contemplated and encompassed by the instant invention.

Treating cancer can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%.

The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound of the present invention. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present invention. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder can result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder can result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

As used herein, the term "selectively" means tending to occur at a higher frequency in one population than in another population. The compared populations can be cell populations. Preferably, a compound of the present invention (i.e., the hydrobromide of Compound I, as well as Polymorph A) acts selectively on a cancer or precancerous cell but not on a normal cell. Preferably, a compound of the present invention acts selectively to modulate one molecular target (e.g., a target protein methyltransferase) but does not significantly modulate another molecular target (e.g., a non-target protein methyltransferase). The invention also provides a method for selectively inhibiting the activity of an enzyme, such as a protein methyltransferase. Preferably, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

A compound of the present invention can modulate the activity of a molecular target (e.g., a target protein methyltransferase). Modulating refers to stimulating or inhibiting an activity of a molecular target. Preferably, a compound of the present invention modulates the activity of a molecular target if it stimulates or inhibits the activity of the molecular target by at least 2-fold relative to the activity of the molecular target under the same conditions but lacking only the presence of said compound. More preferably, a compound of the present invention modulates the activity of a molecular target if it stimulates or inhibits the activity of the molecular target by at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

A compound of the present invention (i.e., the hydrobromide of Compound I, as well as Polymorph A) does not significantly modulate the activity of a molecular target if the addition of the compound does not stimulate or inhibit the activity of the molecular target by greater than 10% relative to the activity of the molecular target under the same conditions but lacking only the presence of said compound.

As used herein, the term "isozyme selective" means preferential inhibition or stimulation of a first isoform of an enzyme in comparison to a second isoform of an enzyme (e.g., preferential inhibition or stimulation of a protein methyltransferase isozyme alpha in comparison to a protein methyltransferase isozyme beta). Preferably, a compound of the present invention demonstrates a minimum of a fourfold differential, preferably a tenfold differential, more preferably a fifty fold differential, in the dosage required to achieve a biological effect. Preferably, a compound of the present invention demonstrates this differential across the range of inhibition, and the differential is exemplified at the $IC_{50}$, i.e., a 50% inhibition, for a molecular target of interest.

Administering a compound of the present invention to a cell or a subject in need thereof can result in modulation (i.e., stimulation or inhibition) of an activity of a protein methyltransferase of interest.

Treating cancer or a cell proliferative disorder can result in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., *Proc Natl Acad Sci USA*. 100(5): 2674-8, 2003. In an aspect, cell death occurs by apoptosis.

Preferably, an effective amount of a compound of the present invention is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

Contacting a cell with a compound of the present invention can induce or activate cell death selectively in cancer cells. Administering to a subject in need thereof a compound of the present invention can induce or activate cell death selectively in cancer cells. Contacting a cell with a compound of the present invention can induce cell death selectively in one or more cells affected by a cell proliferative disorder. Preferably, administering to a subject in need thereof a compound of the present invention induces cell death selectively in one or more cells affected by a cell proliferative disorder.

The present invention relates to a method of treating or preventing cancer (e.g, the course of which can be influenced by modulating EZH2-mediated protein methylation) by administering a compound of the present invention (i.e., the hydrobromide of Compound I, as well as Polymorph A) to a subject in need thereof, where administration of the compound of the present invention results in one or more of the following: prevention of cancer cell proliferation by accumulation of cells in one or more phases of the cell cycle (e.g. G1, G1/S, G2/M), or induction of cell senescence, or promotion of tumor cell differentiation; promotion of cell death in cancer cells via cytotoxicity, necrosis or apoptosis, without a significant amount of cell death in normal cells, antitumor activity in animals with a therapeutic index of at least 2. As used herein, "therapeutic index" is the maximum tolerated dose divided by the efficacious dose. The present invention also relates to a method used to identify suitable candidates for treating or preventing cancer.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* (3$^{rd}$ edition), Cold Spring Harbor Press, Cold Spring Harbor, N.Y. (2000); Coligan et al., *Current Protocols in Immunology*, John Wiley & Sons, N. Y.; Enna et al., *Current Protocols in Pharmacology*, John Wiley & Sons, N. Y.; Fingl et al., *The Pharmacological Basis of Therapeutics* (1975), *Remington's Pharmaceutical Sciences*, Mack Publishing Co., Easton, Pa., 18$^{th}$ edition (1990). These texts can, of course, also be referred to in making or using an aspect of the invention.

Exemplification

Materials and Methods

Powder X-Ray Diffraction

PXRD for all samples was taken on a Rigaku MultiFlex (Target: Cu; Tube voltage: 40 kV; Tube current: 30 mA).

Differential Scanning Calorimetry

DSC for all samples was taken on a Mettler-Toledo DSC 1/700 (Run conditions: Initial temperature 35° C., Final temp 325° C., Heating rate 30° C./min).

X-Ray Crystallography

A colorless plate crystal with dimensions 0.28×0.22×0.06 mm was mounted on a Nylon loop using very small amount of paratone oil. Data were collected using a Bruker CCD (charge coupled device) based diffractometer equipped with an Oxford Cryostream low-temperature apparatus operating at 173 K. Data were measured using omega and phi scans of 0.5° per frame for 45 s. The total number of images was based on results from the program COSMO where redundancy was expected to be 4.0 and completeness to 100% out to 0.83 Å. Cell parameters were retrieved using APEX II software and refined using SAINT on all observed reflections. Data reduction was performed using the SAINT software which corrects for Lp. Scaling and absorption corrections were applied using SADABS multi-scan technique, supplied by George Sheldrick. The structures are solved by the direct method using the SHELXS-97 program and refined by least squares method on F$^2$, SHELXL-97, which are incorporated in SHELXTL-PC V 6.10.

The structure shown in FIG. 11 was solved in the space group P2$_1$/c (#14). All non-hydrogen atoms are refined anisotropically. Hydrogens were calculated by geometrical methods and refined as a riding model. The crystal used for the diffraction study showed no decomposition during data collection. All drawings are done at 50% ellipsoids.

Dynamic Vapor Sorption

DVS was measured on a VTI Model SGA-100 system. Measurement method: The relative humidity (RH) was changed in a controlled fashion, in 5% steps from 5.0% to 95.0% then back to 5.0% using the gravimetric vapor sorption system, and the weight percentage change (wt %) of the sample at each stage was measured.

HPLC

HPLC was conducted on an Agilent 1200 HPLC quaternary pump, low pressure mixing, with an in-line degasser. Analytical method conditions: 8 µL sample (20 mg of ER-581982-06 diluted with 50 mL of a methanol to provide approximately 0.4 mg/mL solution) was injected onto a Agilent Zorbax Eclipse XDB-C18 (4.6×150 mm, 3.5 um), Chromatography conditions: mobile phase A, water with 5 mM ammonium formate; mobile phase B, 5 mM ammonium formate in 50/45/5 acetonitrile/methanol/water; flow rate, 1.5 ml/min.; gradient: isocratic at 10% B from 0 to 3 min; linear increase to 70% B from 3 to 7 min; isocratic at 70% B from 7 to 12 min; linear increase to 100% B from 12 to 15 min isocratic at 100% B from 15 to 20 min; column temperature, 35° C.; detection, UV 230 nm. Approximate retention time of Compound I=10.7 min.

Synthesis of Polymorph A

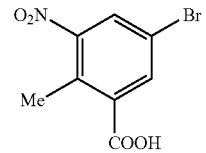 [SMILES: Cc1c(C(=O)O)cc(Br)cc1[N+](=O)[O-]]

5-bromo-2-methyl-3-nitrobenzoic acid stirred solution of 2-methyl-3-nitrobenzoic acid (100 g, 552 mmol) in conc. H$_2$SO$_4$ (400 mL), 1,3-dibromo-5,5-dimethyl-2,4-imidazolidinedione (88 g, 308 mmol) was added in a portion wise manner at room temperature and the reaction mixture was then stirred at room temperature for 5 h. The reaction mixture was poured onto ice cold water, the precipitated solid was filtered off, washed with water and dried under vacuum to afford the desired compound as a solid (140 g, 98%). The isolated compound was taken directly into the next step. $^1$H NMR (DMSO-d$_6$, 400 MHz) δ 8.31 (s, 1H), 8.17 (s, 1H), 2.43 (s, 3H).

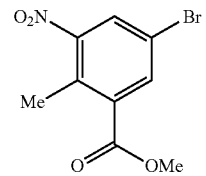 [SMILES: COC(=O)c1cc(Br)cc([N+](=O)[O-])c1C]

Methyl 5-bromo-2-methyl-3-nitrobenzoate To a stirred solution of 5-bromo-2-methyl-3-nitrobenzoic acid (285 g, 1105 mmol) in DMF (2.8 L) at room temperature was added sodium carbonate (468 g, 4415 mmol) followed by addition of methyl iodide (626.6 g, 4415 mmol). The resulting reaction mixture was heated at 60° C. for 8 h. After completion (monitored by TLC), the reaction mixture was filtered (to remove sodium carbonate) and washed with ethyl acetate (1 L×3). The combined filtrate was washed with water (3 L×5) and the aqueous phase was back extracted with ethyl acetate (1 L×3). The combined organic layers were dried over anhydrous sodium sulfate, filtered and concentrated under reduced pressure to afford the title compound as a solid (290 g, 97% yield). The isolated compound was taken directly into the next step. $^1$H NMR (CDCl$_3$, 400 MHz) δ 8.17 (s, 1H), 7.91 (s, 1H), 3.96 (s, 3H), 2.59 (s, 3H).

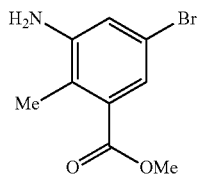

Methyl 3-amino-5-bromo-2-methylbenzoate (1) To a stirred solution of methyl 5-bromo-2-methyl-3-nitrobenzoate (290 g, 1058 mmol) in ethanol (1.5 L) was added aqueous ammonium chloride (283 g, 5290 mmol dissolved in 1.5 L water). The resulting mixture was stirred at 80° C. to which iron powder (472 g, 8451 mmol) was added in a portion wise manner. The resulting reaction mixture was heated at 80° C. for 12 h. Upon completion as determined by TLC, the reaction mixture was hot filtered over Celite® and the celite bed was washed with methanol (5 L) followed by washing with 30% MeOH in DCM (5 L). The combined filtrate was concentrated in-vacuo, the residue obtained was diluted with aqueous sodium bicarbonate solution (2 L) and extracted with ethyl acetate (5 L×3). The combined organic layers were dried over anhydrous sodium sulfate, filtered and concentrated under reduced pressure to afford the title compound as a solid (220 g, 85%). The compound was taken directly into the next step. $^1$H NMR (CDCl$_3$, 400 MHz) δ 7.37 (s, 1H), 6.92 (s, 1H), 3.94 (s, 3H), 3.80 (bs, 2H), 2.31 (s, 3H).

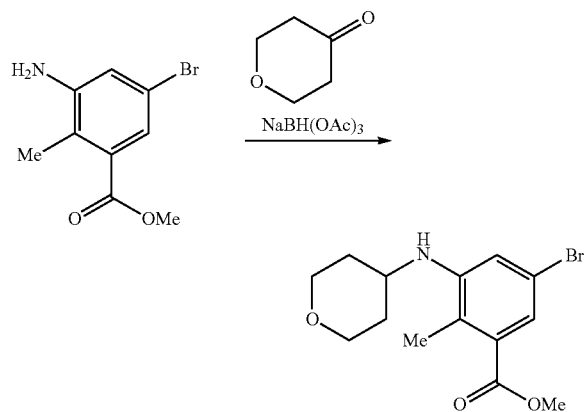

Methyl 5-bromo-2-methyl-3-((tetrahydro-2H-pyran-4-yl) amino) benzoate (2) A reactor was charged with methyl 3-amino-5-bromo-2-methylbenzoate (455.8 g, 1.87 mol), 1,2-Dichloroethane (4.56 L), and acetic acid (535 ml, 9.34 mol). To the mixture were added dihydro-2H-pyran-4(3H)-one (280 g, 2.80 mol) and sodium triacetoxyborohydride (594 g, 2.80 mol) maintaining the internal temperature below 40° C. The mixture was stirred at 25° C. for 2.5 h and then the reaction was quenched with a solution of sodium hydroxide (448 g, 11.20 mol) in water (5.61 L). After stirring for 20 minutes at ambient temperature, the organic layer was separated and the aqueous layer was extracted with ethyl acetate (3.65 L). The organic layers were combined, washed with brine (1.5 L), and concentrated under vacuum.

The residue was treated with ethyl acetate (1.8 L) and heated to 65-70° C. The mixture was stirred at 65-70° C. for 15 minutes to give a clear solution and then treated with n-heptane (7.3 L) maintaining the temperature between 60-70° C. Once the heptane was completely added to the solution, the mixture was held at 65-70° C. for 15 minutes and then allowed to cool to 18-22° C. over 3 h. The resulting suspension was stirred at 18-22° C. for 4 h, cooled to 0-5° C. over 1 h, and held at 0-5° C. for 2 h. The precipitate was filtered, washed twice with n-heptane (1.4 L), and dried under vacuum to give the title compound (540 g, 88%). The XRPD pattern of this compound is shown in FIG. 17.

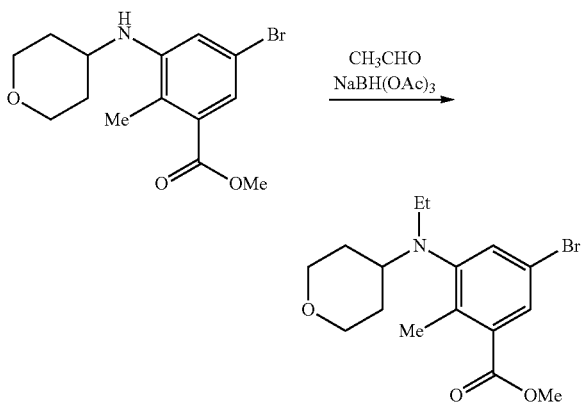

Methyl 5-bromo-3-(ethyl (tetrahydro-2H-pyran-4-yl) amino)-2-methylbenzoate (3) To a stirred solution of methyl 5-bromo-2-methyl-3-((tetrahydro-2H-pyran-4-yl) amino) benzoate (14 g, 42.7 mmol) in dichloroethane (150 mL) was added acetaldehyde (3.75 g, 85.2 mmol) and acetic acid (15.3 g, 256 mmol). The resulting reaction mixture was stirred at room temperature for 15 minutes. The mixture was cooled to 0° C. and sodium triacetoxyborohydride (27 g, 128 mmol) was added. The reaction mixture was stirred at room temperature for 3 hours. Upon completion of the reaction as determined by TLC, aqueous sodium bicarbonate solution was added to the reaction mixture until a pH 7-8 was obtained, the organic phase was separated and the aqueous phase was extracted with ethyl acetate. The combined organic layers were dried over anhydrous sodium sulfate, filtered and concentrated under reduced pressure. The crude compound was purified by column chromatography (100-200 mesh silica gel) eluting with ethyl acetate:hexane to afford the desired compound as a viscous liquid (14 g, 93%). $^1$H NMR (DMSO-d$_6$, 400 MHz) δ 7.62 (s, 1H), 7.52 (s, 1H), 3.80 (bs, 5H), 3.31 (t, 2H), 2.97-3.05 (m, 2H), 2.87-2.96 (m, 1H), 2.38 (s, 3H), 1.52-1.61 (m, 2H), 1.37-1.50 (m, 2H), 0.87 (t, 3H, J=6.8 Hz).

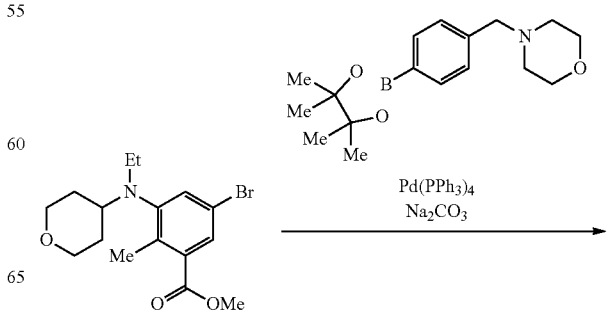

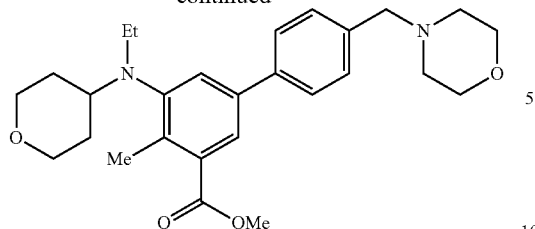
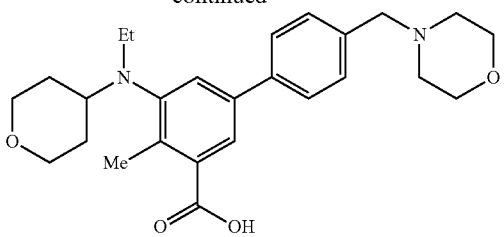

Methyl 5-(ethyl(tetrahydro-2H-pyran-4-yl)amino)-4-methyl-4'-(morpholinomethyl)-[1,1'-biphenyl]-3-carboxylate (4): A mixture of methyl 5-bromo-3-(ethyl(tetrahydro-2H-pyran-4-yl)amino)-2-methylbenzoate (580 g, 1.63 mol), 4-(4-(4,4,5,5-tetramethyl-1,3,2-dioxaborolan-2-yl)benzyl)morpholine (592 g, 1.95 mol), 1,4-dioxane (3.86 L), sodium carbonate (618 g, 5.83 mol), and water (771 ml) was degassed by bubbling nitrogen through the mixture at 20° C. for 20 minutes and treated with tetrakis(triphenylphosphine)palladium(0) (14.11 g, 12.21 mmol). The resulting mixture was degassed for an additional 20 minutes and then heated to 87-89° C. for 17 h. After cooling to 20° C., the mixture was diluted with ethyl acetate (5.80 L) and a solution of (R)-2-Amino-3-mercaptopropionic acid (232 g) in water (2.320 L). After stirring for 1 h at 20° C., the organic layer was separated and washed again with a solution of (R)-2-Amino-3-mercaptopropionic acid (232 g) in water (2.320 L). The aqueous layers were combined and extracted with ethyl acetate (5.80 L). The organic layers were combined, washed with a solution of sodium hydroxide (93 g) in water (2.32 L), and concentrated under vacuum at 35° C. to give the title compound as an orange oil (1.21 kg, 164% yield).

5-(Ethyl(tetrahydro-2H-pyran-4-yl)amino)-4-methyl-4'-(morpholinomethyl)-[1,1'-biphenyl]-3-carboxylic acid (5): Methyl 5-(ethyl(tetrahydro-2H-pyran-4-yl)amino)-4-methyl-4'-(morpholinomethyl)-[1,1'-biphenyl]-3-carboxylate (69.0 g, 152.5 mmol) (based on the theoretical yield from the previous step) was suspended in ethanol (380 mL) and treated with a solution of sodium hydroxide (24.84 g, 621.0 mmol) in water (207 mL). The mixture was stirred at 40° C. for 18 h. After cooling to 0-5° C., the mixture was neutralized to pH 6.5 with 1 N hydrochloric acid (580 mL) maintaining the temperature below 25° C. Then, the mixture was extracted twice with a mixture of dichloromethane (690 mL) and methanol (69.0 mL). The organic layers were combined and concentrated under vacuum to give a crude product as a yellow solid (127 g).

The crude product was dissolved in 2-methyltetrahydrofuran (656 mL) at 70° C. and then treated with IPA (828 mL). The mixture was allowed to cool to rt over 3-4 h and then stirred overnight at rt. The precipitate was filtered, washed twice with IPA (207 mL), and dried under vacuum to give the title compound as an off white solid (53.54 g, 80%). The XRPD pattern of this compound is shown in FIG. 9.

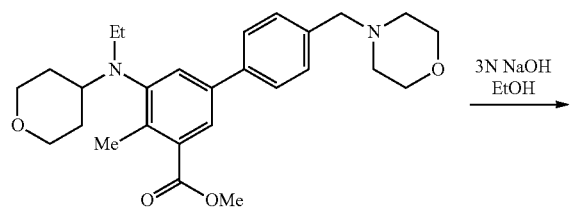

3N NaOH
EtOH

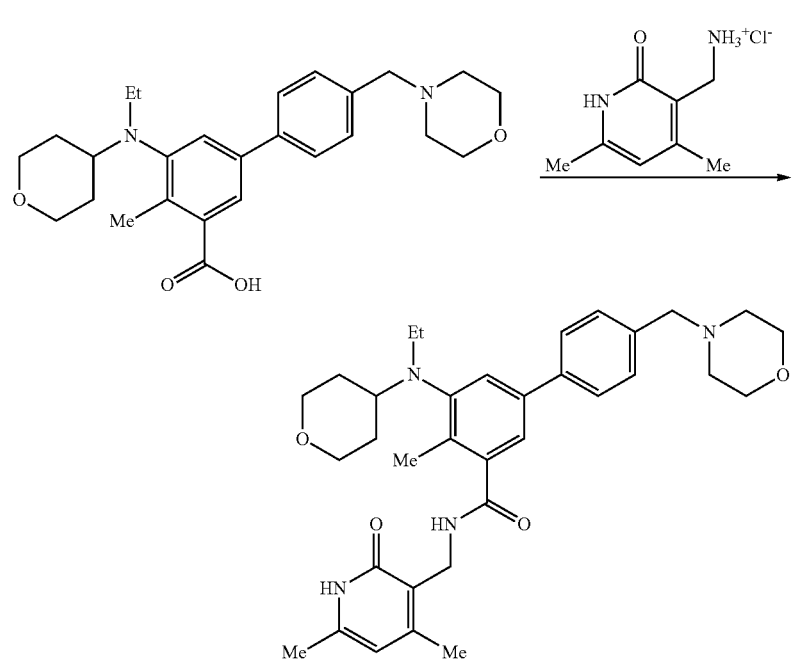

N-((4,6-dimethyl-2-oxo-1,2-dihydropyridin-3-yl)methyl)-5-(ethyl(tetrahydro-2H-pyran-4-yl)amino)-4-methyl-4'-(morpholinomethyl)-[1,1'-biphenyl]-3-carboxamide (Compound I): A mixture of 5-(ethyl(tetrahydro-2H-pyran-4-yl)amino)-4-methyl-4'-(morpholinomethyl)-[1,1'-biphenyl]-3-carboxylic acid (540 g, 1.23 mol) and 3-(aminomethyl)-4,6-dimethyl-dihydro-pyridin-2(1H)-one hydrochloride (279 g, 1.48 mol) was suspended in DMSO (2.70 L) and treated with triethylamine (223 ml, 1.60 mol). The mixture was stirred at 25° C. for 30 min and treated with EDC-HCl (354 g, 1.85 mol) and HOBT hydrate (283 g, 1.85 mol). The reaction mixture was stirred at rt for 16 h. After addition of triethylamine (292 ml, 2.09 mol), the mixture was cooled to 15° C., diluted with water (10.1 L) maintaining the temperature below 30° C., and stirred at 19-25° C. for 4 h. The resulting precipitate was filtered, washed twice with water (2.70 L), and dried under vacuum to give a crude product (695 g, wt-wt analysis=78%).

For the further purification of the product, recrystallization was conducted. A crude product (20.00 g, 34.92 mmol) was suspended in a mixture of ethanol (190 ml) and water (10.00 ml) and heated to 75° C. until a clear solution was obtained. The solution was allowed to cool to rt overnight. The precipitate was filtered, washed twice with a mixture of ethanol (30.0 ml) and water (30.0 ml), and dried under vacuum at 35° C. to give the title compound as an off white solid (14.0 g, 70% recovery from the crude and 90% yield based on wt-wt assay).

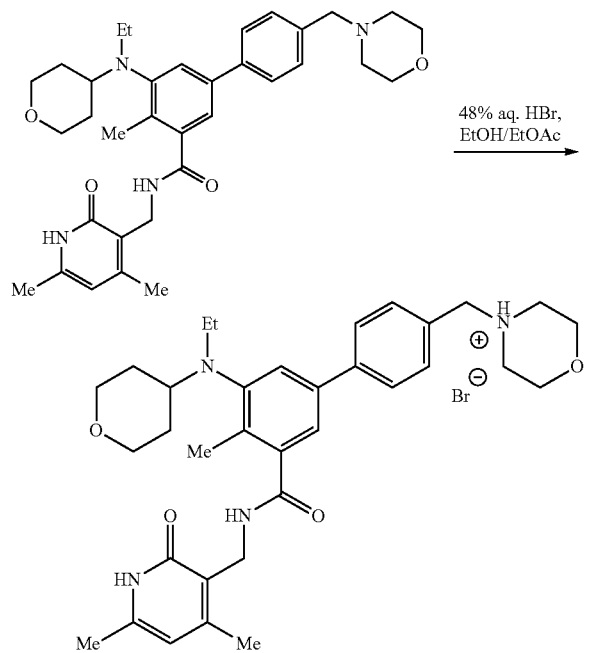

4-((3'-(((4,6-dimethyl-2-oxo-1,2-dihydropyridin-3-yl)methyl)carbamoyl)-5'-(ethyl (tetrahydro-2H-pyran-4-yl)amino)-4'-methyl-[1,1'-biphenyl]-4-yl)methyl)morpholin-4-ium bromide (Polymorph A): A crude N-((4,6-dimethyl-2-oxo-1,2-dihydropyridin-3-yl) methyl)-5-(ethyl(tetrahydro-2H-pyran-4-yl)amino)-4-methyl-4'-(morpholinomethyl)-[1,1'-biphenyl]-3-carboxamide (595 g, 464 g based on wt-wt assay, 810.3 mmol) was suspended in ethanol (3.33 L). After heating to 70° C., the mixture was treated with 48% aqueous HBr (97 ml, 850.8 mmol) and stirred at 70° C. for 30 min. The resulting orange-red solution was treated with ethyl acetate (3.33 L) maintaining the temperature above 60° C. The mixture was slowly cooled to rt over 18 h. The mixture was cooled to 0° C. over 1 h and stirred at that temperature for 5.5 h. The resulting precipitate was filtered, washed twice with ethyl acetate (1.39 L), and dried under vacuum to give the title compound as an off white solid (515 g, 97% yield).

Figure 1:
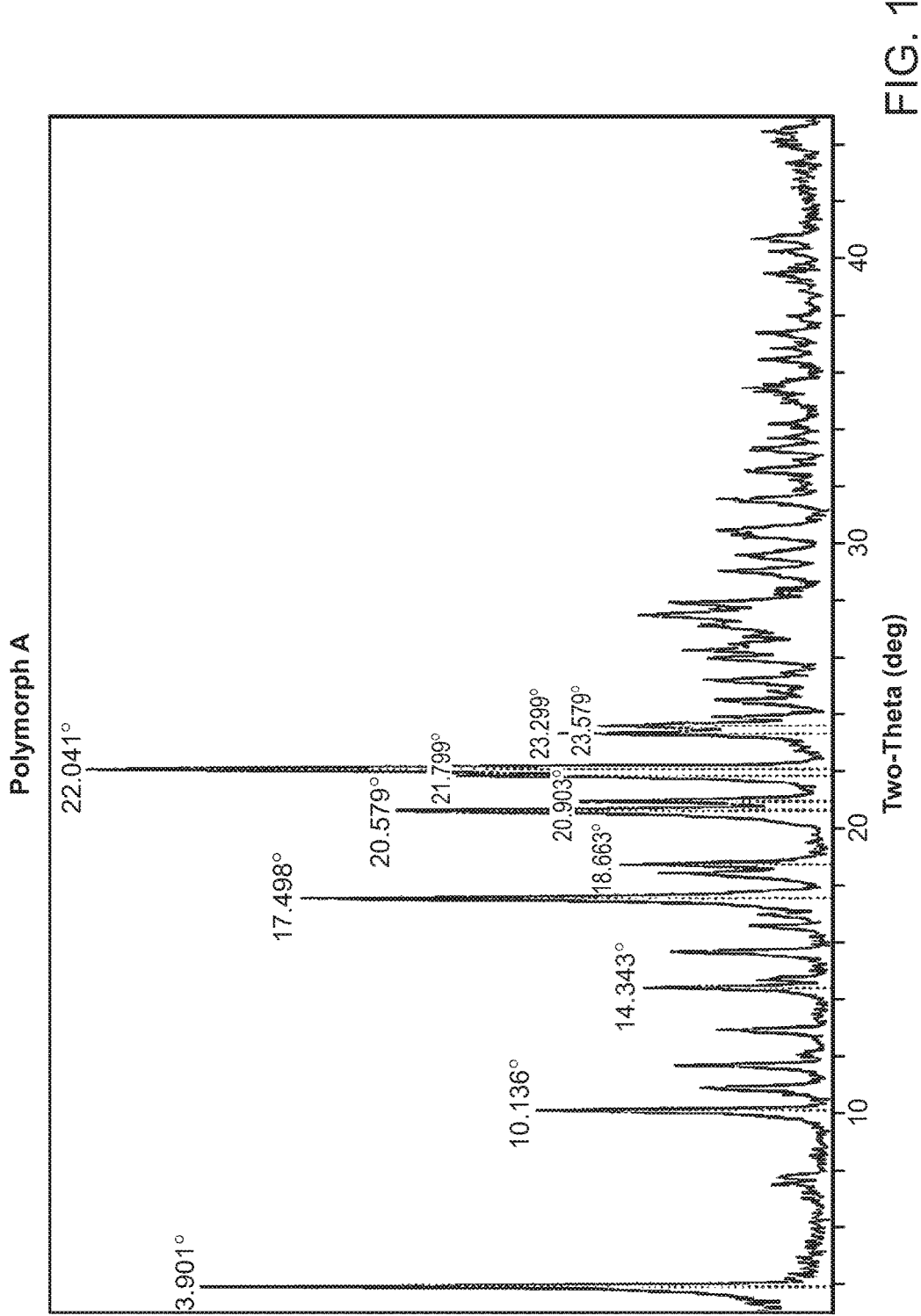
FIG. 1 depicts the X-ray powder diffraction pattern of Polymorph A (monohydrobromide).

Recrystallization of Polymorph A: 4-((3'-(((4,6-dimethyl-2-oxo-1,2-dihydropyridin-3-yl) methyl)carbamoyl)-5'-(ethyl(tetrahydro-2H-pyran-4-yl)amino)-4'-methyl-[1,1'-biphenyl]-4-yl) methyl)morpholin-4-ium bromide (0.50 g, 0.77 mmol; 95.6% pure by HPLC) was suspended in ethanol (3.0 mL) and heated to 80° C. until a clear solution was obtained. To the solution was added MTBE (5.0 mL) slowly. The resulting solution was allowed to cool to 18-22° C. over 3 h and stirred at 18-22° C. for 15 h. The precipitate was filtered, washed twice with MTBE (2 mL) and dried under vacuum to give 0.45 g of the title compound (89% recovery, 96.6% pure by HPLC). The X-ray powder diffraction pattern of Polymorph A (monohydrobromide) is shown in FIG. 1. Table 1, below, lists the most significant peaks.

TABLE 1

| Peaks (Degrees 2-theta) |
| --- |
| 3.9 |
| 10.1 |
| 14.3 |
| 17.5 |
| 18.7 |
| 20.6 |
| 20.9 |
| 21.8 |
| 22.0 |
| 23.3 |
| 23.6 |

Assessment of Hydrobromide of Compound I and Polymorph A

A number of different salt forms of Compound I were prepared and screened, including hydrochloride, hydrobromide, hemisulfate, sodium, phosphate, nitrate, maleate, malonate, and L-tartrate salts. Among them, the hydrobromide (HBr) salt had the most advantageous physicochemical properties in terms of ease of preparation and hygroscopicity.

Detailed studies of the free base of Compound I as well as the HCl salt of this compound were carried out. At least five different crystal forms were detected from the free form of Compound I during preliminary polymorph screening using XRD and DSC. Due to the high degree of variability observed during crystallization of the free form, crystal forms of other salts were pursued. Of the screened salts, the monohydrochloride, monohydrobromide, hemisulfate, phosphate, maleate, L-tartarate and sodium salt forms were crystalline. The phosphate and maleate salts were very hygroscopic and L-tartarate had poor crystallinity.

Figure 8:
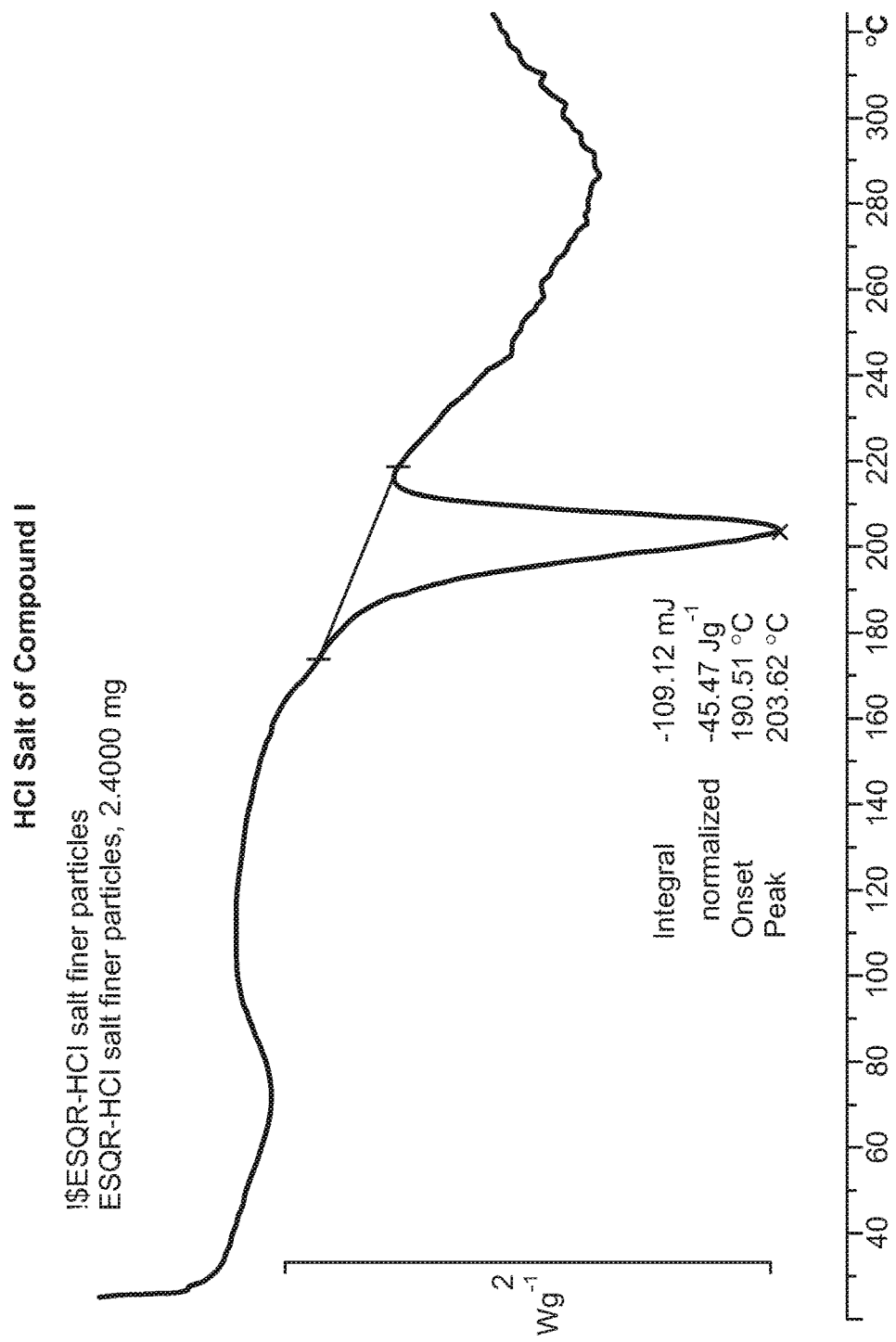
FIG. 8 shows differential scanning calorimetry data of the monohydrochloride salt of Compound I, which indicates that this compound is poorly crystalline.
Figure 18A:
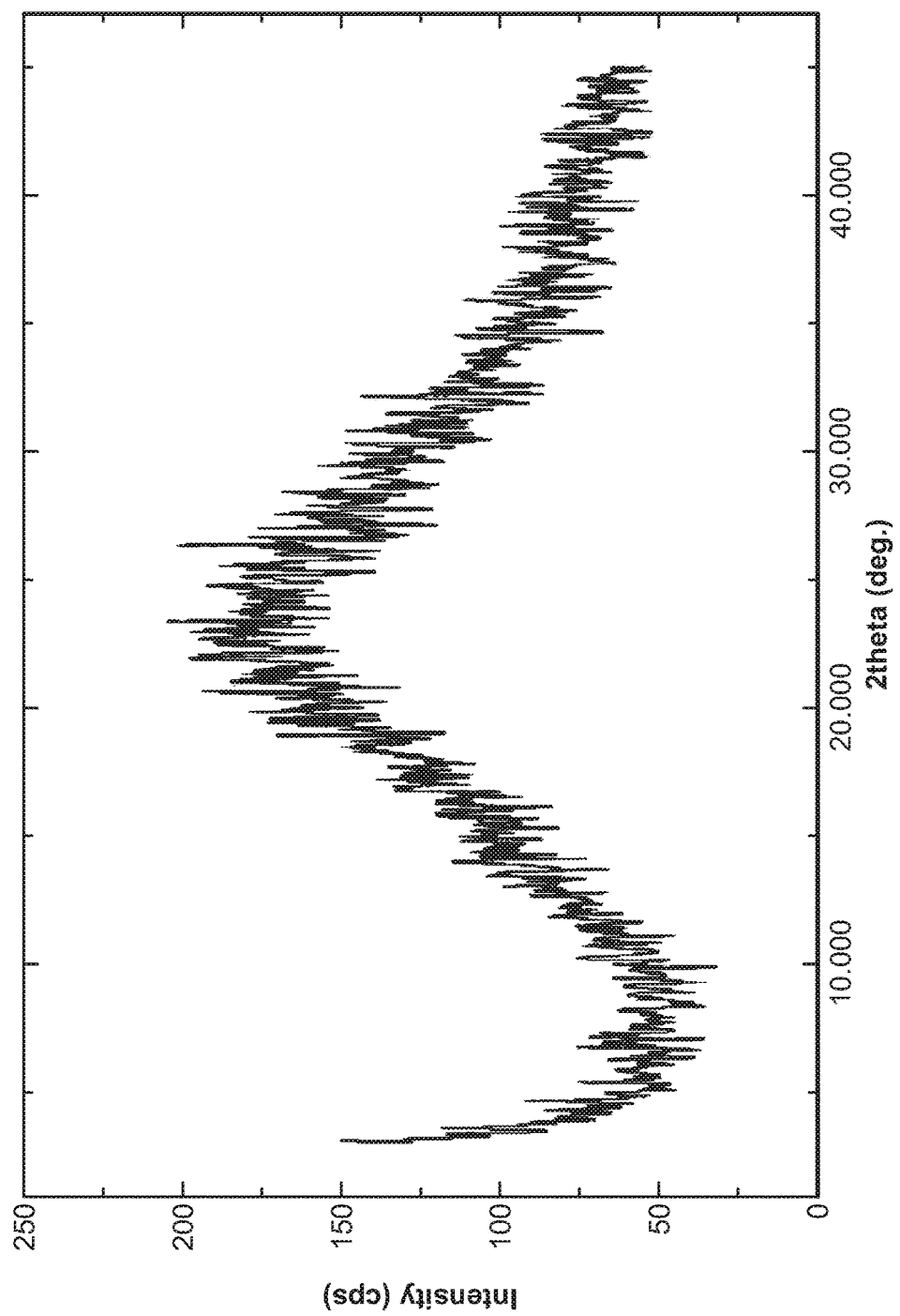
FIGS. 18A and B depict (A) the X-ray powder diffraction pattern of the trihydrochloride salt of Compound I and (B) the dynamic vapor sorption of the monohydrochloride salt of Compound I, which demonstrates the significant hygroscopicity of this compound.
Figure 18B:
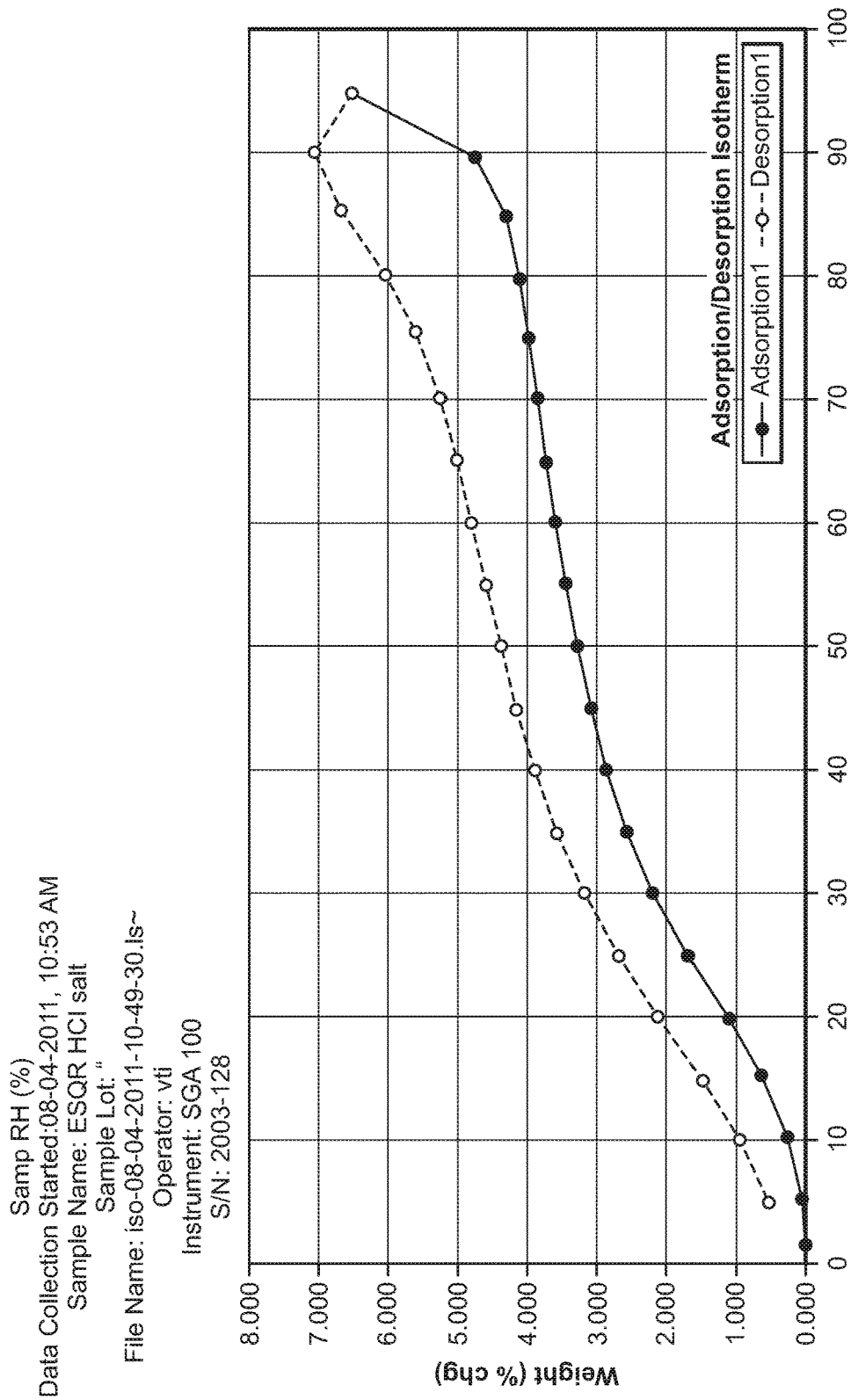

It was difficult to obtain high degree of crystallinity from HCl salt of Compound I. A mixture of crystalline and amorphous material was obtained irrespective of crystallization conditions. As shown in FIG. 8, DSC data of the monohydrochloride salt of Compound I indicates some degree of non-crystallinity with an endotherm at 190.5° C. Also, dynamic vapor sorption (DVS) data for the monohydrochloride salt of Compound I was obtained and found to show some hygroscopicity: between 4-6% weight gain was observed at 75% relative humidity (RH) at 25° C. (FIG. 18B). This may be attributed to a certain amount of non-crystalline nature of the monohydrochloride salt. See, e.g., FIG. 18A, which shows an amorphous trihydrochloride Compound I. Because the level of crystallinity was not controllable, the HCl salt was not considered for further development.

Figure 6:
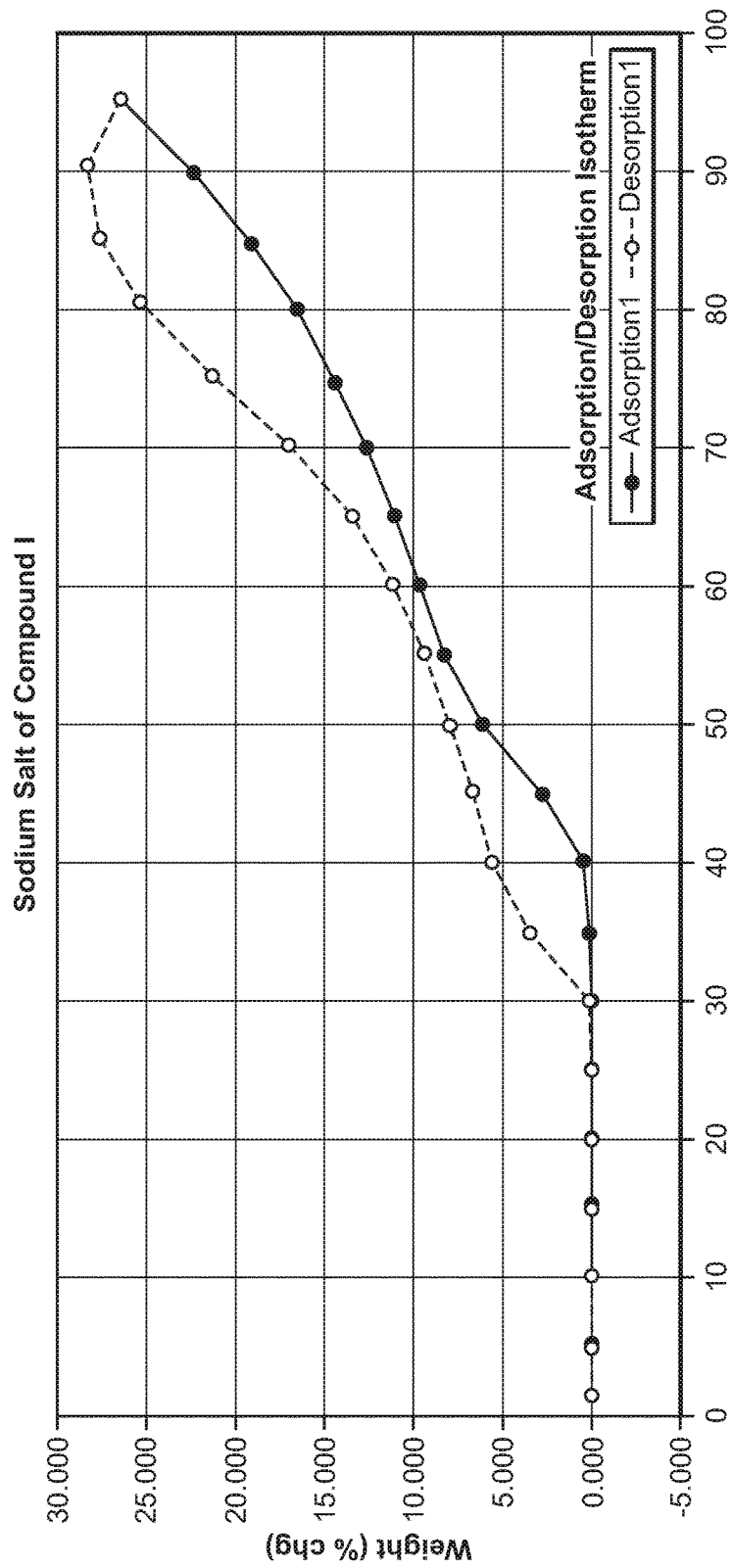
FIG. 6 depicts the dynamic vapor sorption of the sodium salt of Compound I, which demonstrates the significant hygroscopicity of this compound.
Figure 7:
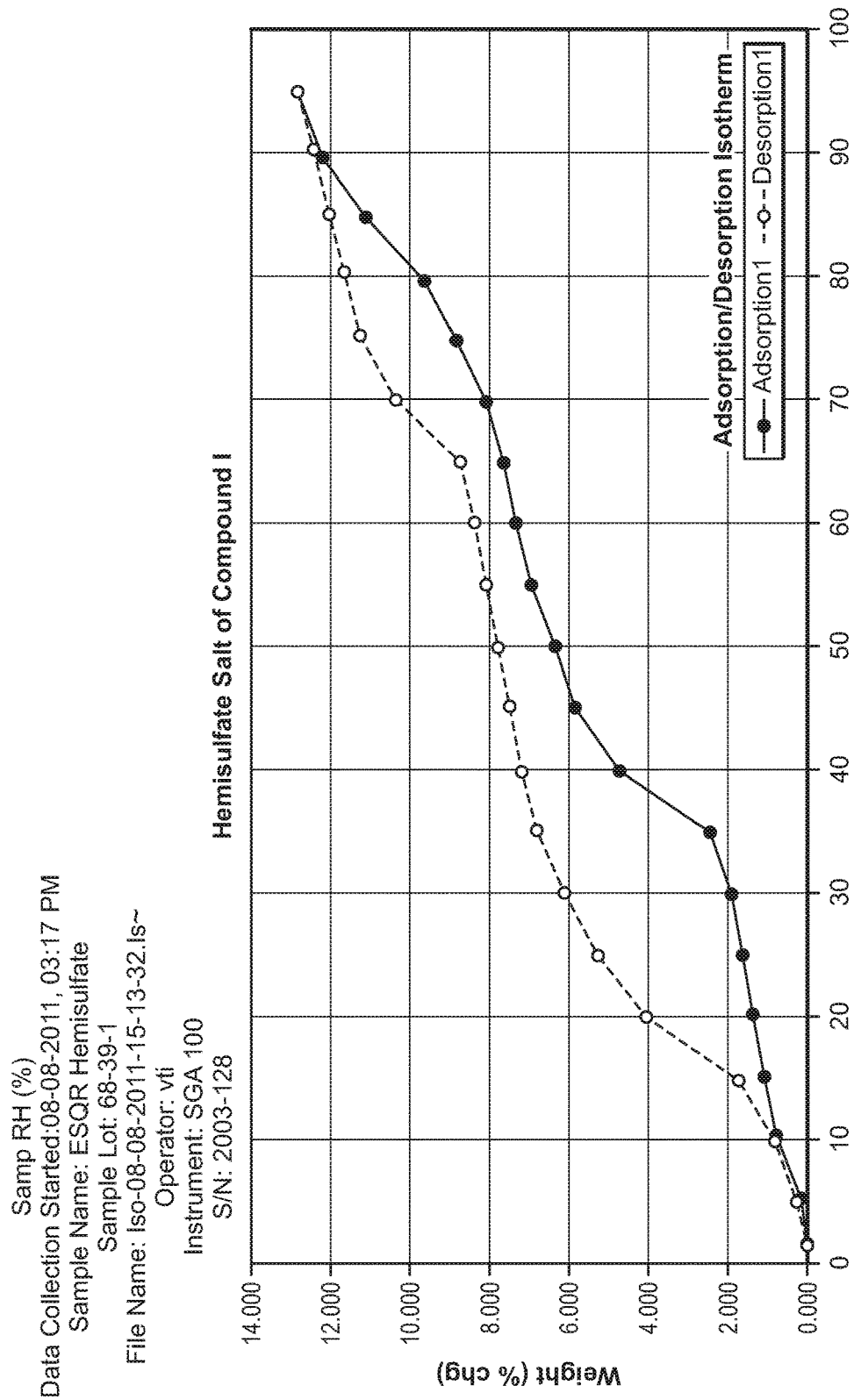
FIG. 7 depicts the dynamic vapor sorption of the hemisulfate salt of Compound I, which demonstrates that this compound has moderately high hygroscopicity.

As shown in FIG. 6, DVS analysis of the sodium salt of Compound I showed significant hygroscopicity: approximately 15% weight gain was observed at 75% relative humidity (RH) at 25° C. As shown in FIG. 7, the hemisulfate salt of Compound I showed moderately high hygroscopicity: between 9-11% weight gain was observed at 75% relative humidity (RH) at 25° C. This may be attributed to the highly non-crystalline nature of the compound, as DSC data of the hemisulfate salt indicates very high degree of non-crystallinity with no clean endotherm.

Figure 2:
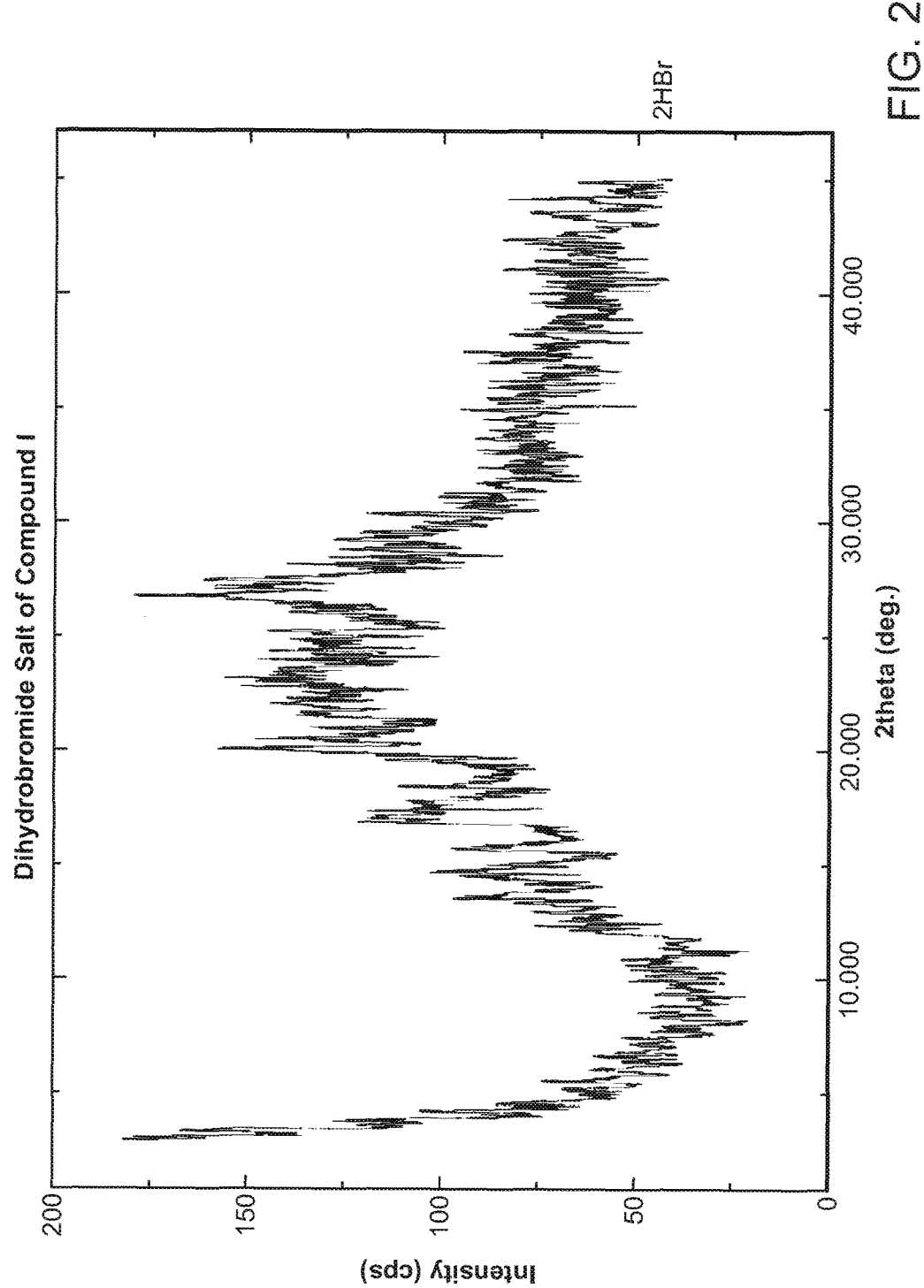
FIG. 2 depicts the X-ray powder diffraction pattern the dihydrobromide of Compound I.
Figure 3:
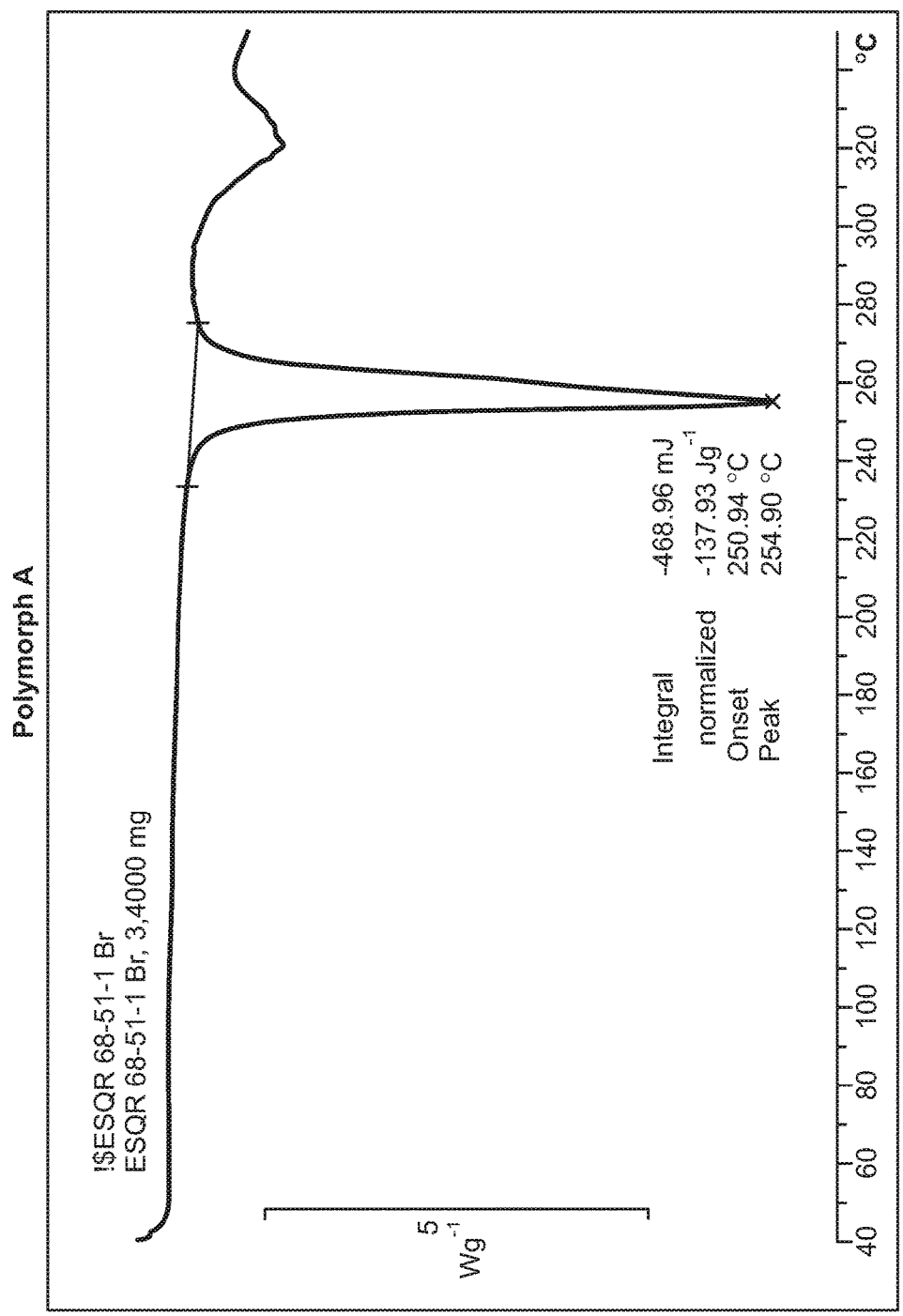
FIG. 3 depicts the differential scanning calorimetry thermogram of Polymorph A.
Figure 4:
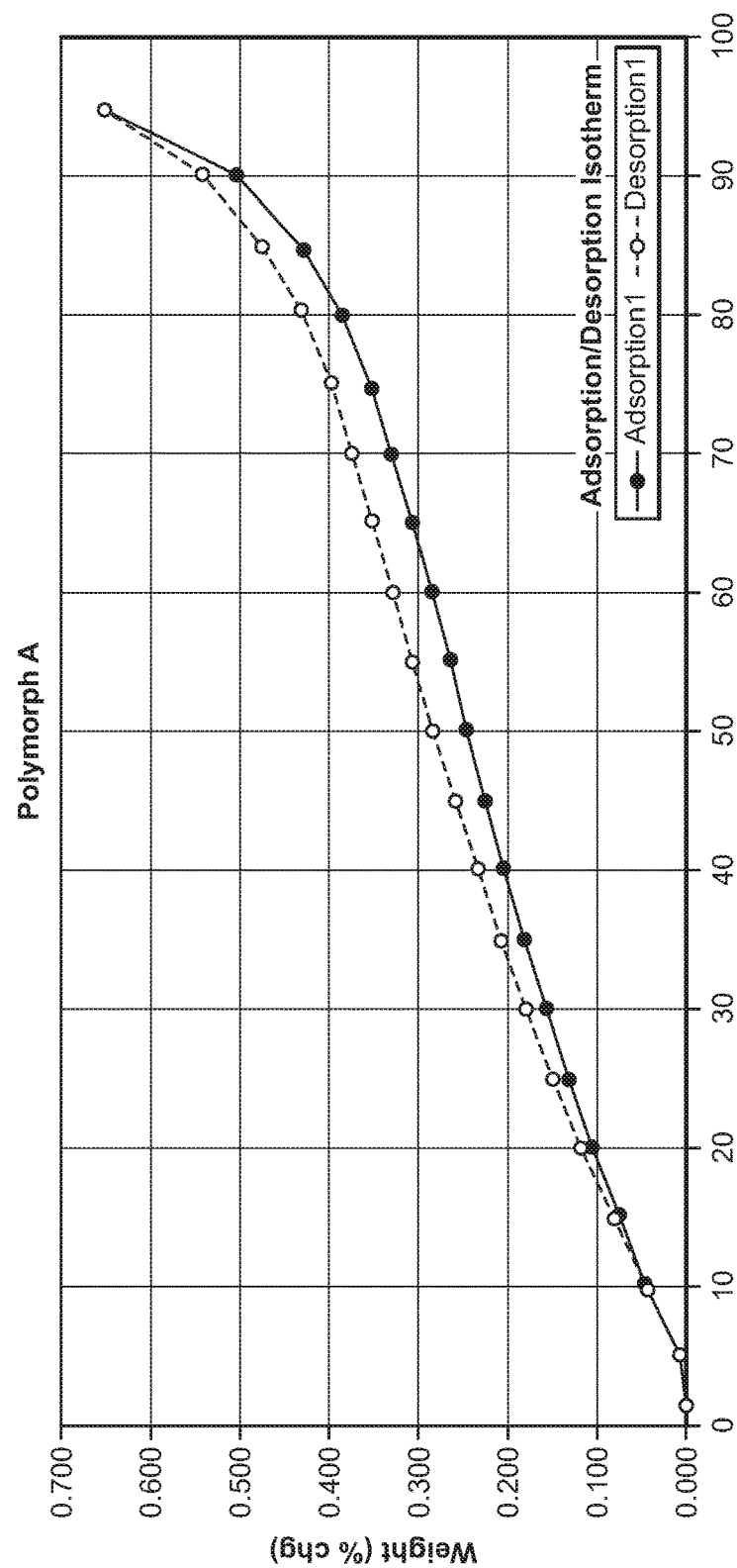
FIG. 4 depicts the dynamic vapor sorption of Polymorph A, which demonstrates the low hygroscopicity of this compound.
Figure 5:
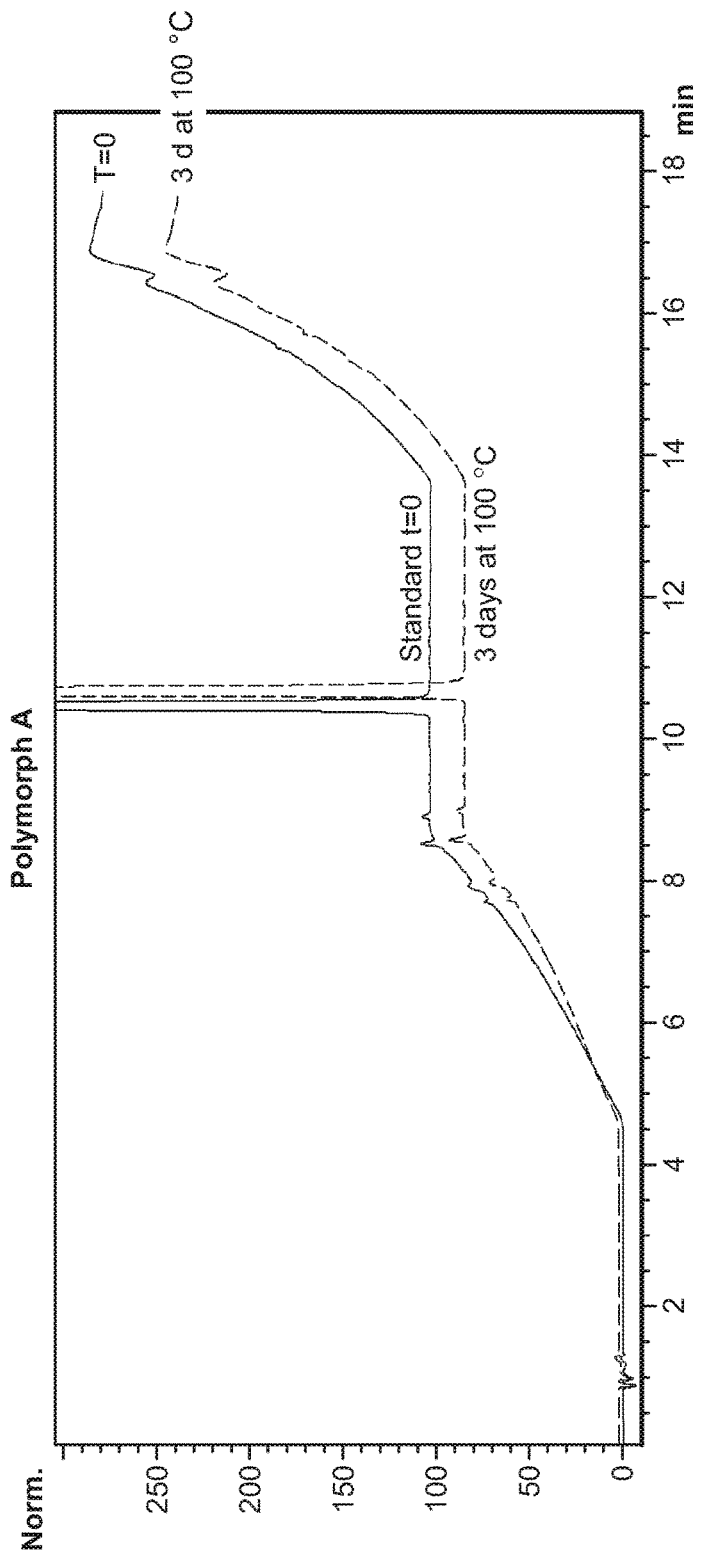
FIG. 5 depicts HPLC analysis of Polymorph A over three days at an elevated temperature. Polymorph A produced minimal impurities over this time.

Of these crystalline compounds, the monohydrobromide was the most crystalline and least hydroscopic (see FIGS. 1, 3, and 4). Furthermore, the monohydrobromide is highly stable, and resists generation of impurities (FIG. 5 depicts HPLC analysis of Polymorph A over three days at an elevated temperature. Polymorph A produced minimal impurities over three days 100° C.). Interestingly, the di-HBr salt of Compound I was found to be primarily amorphous (FIG. 2).

Figure 10:
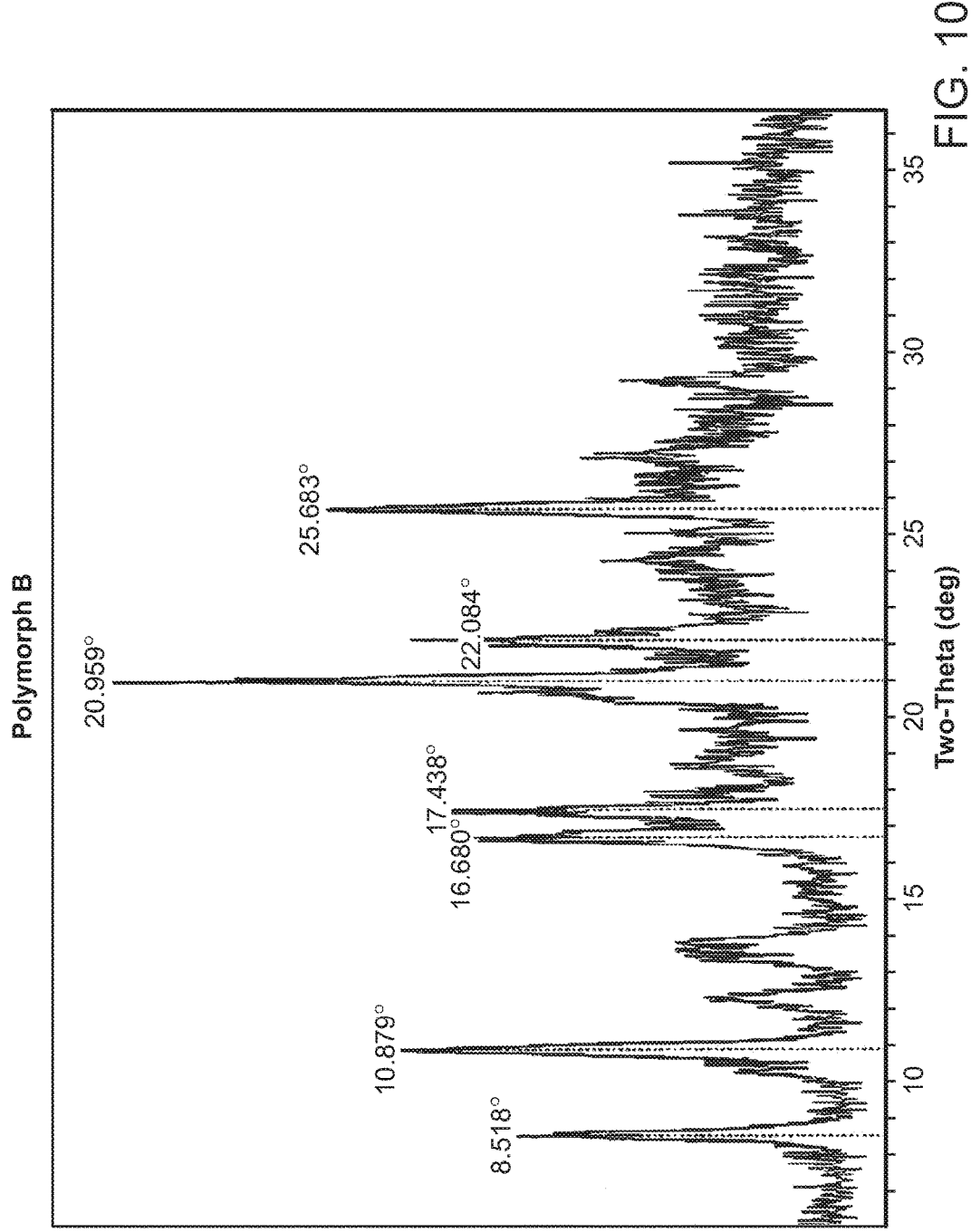
FIG. 10 depicts the X-ray powder diffraction pattern of Polymorph B.

Two different crystal forms of the monohydrobromide of Compound I (Polymorphs A and B) were obtained from different solvent systems and characterized using XRD, DSC and TGA-DSC analyses. XRD and DSC data for these two different crystal forms from representative batches of Compound I are shown in FIG. 1, FIG. 3, and FIG. 10. Polymorph B is characterized by a powder XRD pattern with peaks at 8.5, 10.9, 16.7, 17.4, 20.9, 22.1 and 25.7±0.2 degrees 2 theta (see FIG. 10). Between these two, Polymorph A was found to be more crystalline in nature. Dynamic vapor adsorption (DVS) studies showed that the polymorph A is non-hygroscopic (FIG. 4). In the thermal analyses, a single endothermic peak was observed with an onset temperature approximately at 251° C. In addition, it was evident from DSC analysis that the recrystallization of polymorph A significantly increases the crystallinity of the material (see FIG. 3).

In multiple laboratory scale runs, Polymorph A was obtained reproducibly, and slight changes in crystallization conditions did not result in different crystal forms.

Wild-Type and Mutant PRC2 Enzyme Assays

General Materials. S-adenosylmethionine (SAM), S-adenosylhomocysteine (SAH), bicine, KCl, Tween20, dimethylsulfoxide (DMSO) and bovine skin gelatin (BSG) were purchased from Sigma-Aldrich at the highest level of purity possible. Dithiothreitol (DTT) was purchased from EMD. $^3$H-SAM was purchased from American Radiolabeled Chemicals with a specific activity of 80 Ci/mmol. 384-well streptavidin Flashplates were purchased from PerkinElmer.

Substrates. Peptides representative of human histone H3 residues 21-44 containing either an unmodified lysine 27 (H3K27me0) or dimethylated lysine 27 (H3K27me2) were synthesized with a C-terminal G (K-biotin) linker-affinity tag motif and a C-terminal amide cap by 21$^{st}$ Century Biochemicals. The peptides were high-performance liquid chromatography (HPLC) purified to greater than 95% purity and confirmed by liquid chromatography mass spectrometry (LC-MS). The sequences are listed below.

H3K27me0:
(SEQ ID NO: 1)
ATKAARKSAPATGGVKKPHRYRPGGK(biotin)-amide

H3K27me2:
(SEQ ID NO: 2)
ATKAARK(me2)SAPATGGVKKPHRYRPGGK(biotin)-amide

Chicken erythrocyte oligonucleosomes were purified from chicken blood according to established procedures.

Recombinant PRC2 Complexes. Human PRC2 complexes were purified as 4-component enzyme complexes co-expressed in *Spodoptera frugiperda* (sf9) cells using a baculovirus expression system. The subunits expressed were wild-type EZH2 (NM_004456) or EZH2 Y641F, N, H, S or C mutants generated from the wild-type EZH2 construct, EED (NM_003797), Suz12 (NM_015355) and RbAp48 (NM_005610). The EED subunit contained an N-terminal FLAG tag that was used to purify the entire 4-component complex from sf9 cell lysates. The purity of the complexes met or exceeded 95% as determined by SDS-PAGE and Agilent Bioanalyzer analysis. Concentrations of enzyme stock concentrations (generally 0.3-1.0 mg/mL) was determined using a Bradford assay against a bovine serum albumin (BSA) standard.

General Procedure for PRC2 Enzyme Assays on Peptide Substrates. The assays were all performed in a buffer consisting of 20 mM bicine (pH=7.6), 0.5 mM DTT, 0.005% BSG and 0.002% Tween20, prepared on the day of use. Compounds in 100% DMSO (1 µL) were spotted into polypropylene 384-well V-bottom plates (Greiner) using a Platemate 2×3 outfitted with a 384-channel pipet head (Thermo). DMSO (1 µL) was added to columns 11, 12, 23, 24, rows A-H for the maximum signal control, and SAH, a known product and inhibitor of PRC2 (1 µL) was added to columns 11, 12, 23, 24, rows I-P for the minimum signal control. A cocktail (40 µL) containing the wild-type PRC2 enzyme and H3K27me0 peptide or any of the Y641 mutant enzymes and H3K27me2 peptide was added by Multidrop Combi (Thermo). The compounds were allowed to incubate with PRC2 for 30 min at 25° C., then a cocktail (10 µL) containing a mixture of non-radioactive and $^3$H-SAM was added to initiate the reaction (final volume=51 µL). In all cases, the final concentrations were as follows: wild-type or mutant PRC2 enzyme was 4 nM, SAH in the minimum signal control wells was 1 mM and the DMSO concentration was 1%. The final concentrations of the rest of the components are indicated in Table 2, below. The assays were stopped by the addition of non-radioactive SAM (10 µL) to a final concentration of 600 µM, which dilutes the $^3$H-SAM to a level where its incorporation into the peptide substrate is no longer detectable. 50 µL of the reaction in the 384-well polypropylene plate was then transferred to a 384-well Flashplate and the biotinylated peptides were allowed to bind to the streptavidin surface for at least 1 h before being washed three times with 0.1% Tween20 in a Biotek ELx405 plate washer. The plates were then read in a PerkinElmer TopCount platereader to measure the quantity of $^3$H-labeled peptide bound to the Flashplate surface, measured as disintegrations per minute (dpm) or alternatively, referred to as counts per minute (cpm).

TABLE 2

Final concentrations of components for each assay variation based upon EZH2 identity (wild-type or Y641 mutant EZH2)

| PRC2 Enzyme (denoted by EZH2 identity) | Peptide (nM) | Non-radioactive SAM (nM) | $^3$H-SAM (nM) |
|---|---|---|---|
| Wild-type | 185 | 1800 | 150 |
| Y641F | 200 | 850 | 150 |
| Y641N | 200 | 850 | 150 |
| Y641H | 200 | 1750 | 250 |
| Y641S | 200 | 1300 | 200 |
| Y641C | 200 | 3750 | 250 |

General Procedure for Wild-Type PRC2 Enzyme Assay on Oligonucleosome Substrate. The assays was performed in a buffer consisting of 20 mM bicine (pH=7.6), 0.5 mM DTT, 0.005% BSG, 100 mM KCl and 0.002% Tween20, prepared on the day of use. Compounds in 100% DMSO (1 µL) were spotted into polypropylene 384-well V-bottom plates (Greiner) using a Platemate 2×3 outfitted with a 384-channel pipet head (Thermo). DMSO (1 µL) was added to columns 11, 12, 23, 24, rows A-H for the maximum signal control, and SAH, a known product and inhibitor of PRC2 (1 µL) was added to columns 11, 12, 23, 24, rows I-P for the minimum signal control. A cocktail (40 µL) containing the wild-type PRC2 enzyme and chicken erythrocyte oligonucleosome was added by Multidrop Combi (Thermo). The compounds were allowed to incubate with PRC2 for 30 min at 25° C., then a cocktail (10 µL) containing a mixture of non-radioactive and $^3$H-SAM was added to initiate the reaction (final volume=51 µL). The final concentrations were as follows: wild-type PRC2 enzyme was 4 nM, non-radioactive SAM was 430 nM, $^3$H-SAM was 120 nM, chicken erythrocyte oligonucleosome was 120 nM, SAH in the minimum signal control wells was 1 mM and the DMSO concentration was 1%. The assay was stopped by the addition of non-radioactive SAM (10 µL) to a final concentration of 600 µM, which dilutes the $^3$H-SAM to a level where its incorporation into the chicken erythrocyte oligonucleosome substrate is no longer detectable. 50 µL of the reaction in the 384-well polypropylene plate was then transferred to a 384-well Flashplate and the chicken erythrocyte nucleosomes were immobilized to the surface of the plate, which was then washed three times with 0.1% Tween20 in a Biotek ELx405 plate washer. The plates were then read in a PerkinElmer TopCount platereader to measure the quantity of $^3$H-labeled chicken erythrocyte oligonucleosome bound to the Flashplate surface, measured as disintegrations per minute (dpm) or alternatively, referred to as counts per minute (cpm).

$$\%inh = 100 - \left( \frac{dpm_{cmpd} - dpm_{min}}{dpm_{max} - dpm_{min}} \right) \times 100$$

Where dpm=disintegrations per minute, cmpd=signal in assay well, and min and max are the respective minimum and maximum signal controls.

Four-Parameter IC$_{50}$ Fit $$Y = Bottom + \frac{(Top - Bottom)}{1 + \left(\frac{X}{IC_{50}}\right)^{Hill\ Coefficient}}$$

Where top and bottom are the normally allowed to float, but may be fixed at 100 or 0 respectively in a 3-parameter fit. The Hill Coefficient normally allowed to float but may also be fixed at 1 in a 3-parameter fit. Y is the % inhibition and X is the compound concentration.

IC$_{50}$ values for the PRC2 enzyme assays on peptide substrates (e.g., EZH2 wild type and Y641F) are presented in Table 3 below.

WSU-DLCL2 Methylation Assay

WSU-DLCL2 suspension cells were purchased from DSMZ (German Collection of Microorganisms and Cell Cultures, Braunschweig, Germany). RPMI/Glutamax Medium, Penicillin-Streptomycin, Heat Inactivated Fetal Bovine Serum, and D-PBS were purchased from Life Technologies, Grand Island, N.Y., USA. Extraction Buffer and Neutralization Buffer (5×) were purchased from Active Motif, Carlsbad, Calif., USA. Rabbit anti-Histone H3 antibody was purchased from Abcam, Cambridge, Mass., USA. Rabbit anti-H3K27me3 and HRP-conjugated anti-rabbit-IgG were purchased from Cell Signaling Technology, Danvers, Mass., USA. TMB "Super Sensitive" substrate was sourced from BioFX Laboratories, Owings Mills, Md., USA. IgG-free Bovine Serum Albumin was purchased from Jackson ImmunoResearch, West Grove, Pa., USA. PBS with Tween (10×PBST) was purchased from KPL, Gaithersburg, Md., USA. Sulfuric Acid was purchased from Ricca Chemical, Arlington, Tex., USA. Immulon ELISA plates were purchased from Thermo, Rochester, N.Y., USA. V-bottom cell culture plates were purchased from Corning Inc., Corning, N.Y., USA. V-bottom polypropylene plates were purchased from Greiner Bio-One, Monroe, N.C., USA.

WSU-DLCL2 suspension cells were maintained in growth medium (RPMI 1640 supplemented with 10% v/v heat inactivated fetal bovine serum and 100 units/mL penicillin-streptomycin) and cultured at 37° C. under 5% CO$_2$. Under assay conditions, cells were incubated in Assay Medium (RPMI 1640 supplemented with 20% v/v heat inactivated fetal bovine serum and 100 units/mL penicillin-streptomycin) at 37° C. under 5% CO$_2$ on a plate shaker.

WSU-DLCL2 cells were seeded in assay medium at a concentration of 50,000 cells per mL to a 96-well V-bottom cell culture plate with 200 µL per well. Compound (1 µL) from 96 well source plates was added directly to V-bottom cell plate. Plates were incubated on a titer-plate shaker at 37° C., 5% CO2 for 96 hours. After four days of incubation, plates were spun at 241×g for five minutes and medium was aspirated gently from each well of cell plate without disturbing cell pellet. Pellet was resuspended in 200 µL DPBS and plates were spun again at 241×g for five minutes. The supernatant was aspirated and cold (4° C.) Extraction buffer (100 µL) was added per well. Plates were incubated at 4° C. on orbital shaker for two hours. Plates were spun at 3427× g×10 minutes. Supernatant (80 µL per well) was transferred to its respective well in 96 well V-bottom polypropylene plate. Neutralization Buffer 5× (20 µL per well) was added to V-bottom polypropylene plate containing supernatant. V-bottom polypropylene plates containing crude histone preparation (CHP) were incubated on orbital shaker×five minutes. Crude Histone Preparations were added (2 µL per well) to each respective well into duplicate 96 well ELISA plates containing 100 µL Coating Buffer (1×PBS+BSA 0.05% w/v). Plates were sealed and incubated overnight at 4° C. The following day, plates were washed three times with 300 µL per well 1×PBST. Wells were blocked for two hours with 300 µL per well ELISA Diluent ((PBS (1×) BSA (2% w/v) and Tween20 (0.05% v/v)). Plates were washed three times with 1×PBST. For the Histone H3 detection plate, 100 μL per well were added of anti-Histone-H3 antibody (Abcam, ab1791) diluted 1:10,000 in ELISA Diluent. For H3K27 trimethylation detection plate, 100 μL per well were added of anti-H3K27me3 diluted 1:2000 in ELISA diluent. Plates were incubated for 90 minutes at room temperature. Plates were washed three times with 300 μL 1× PBST per well. For Histone H3 detection, 100 μL of HRP-conjugated anti-rabbit IgG antibody diluted to 1:6000 in ELISA diluent was added per well. For H3K27me3 detection, 100 μL of HRP conjugated anti-rabbit IgG antibody diluted to 1:4000 in ELISA diluent was added per well. Plates were incubated at room temperature for 90 minutes. Plates were washed four times with 1×PBST 300 μL per well. TMB substrate 100 μL was added per well. Histone H3 plates were incubated for five minutes at room temperature. H3K27me3 plates were incubated for 10 minutes at room temperature. The reaction was stopped with sulfuric acid 1N (100 μL per well). Absorbance for each plate was read at 450 nm.

First, the ratio for each well was determined by:

$$\left(\frac{H3K27me3\ OD450}{Histone\ H3\ OD450}\right).$$

Each plate included eight control wells of DMSO only treatment (Minimum Inhibition) as well as eight control wells for maximum inhibition (Background wells).

The average of the ratio values for each control type was calculated and used to determine the percent inhibition for each test well in the plate. Test compound was serially diluted three-fold in DMSO for a total of ten test concentrations, beginning at 25 μM. Percent inhibition was determined and $IC_{50}$ curves were generated using duplicate wells per concentration of compound. $IC_{50}$ values for this assay are presented in Table 3 below.

$$\text{Percent Inhibition} = 100 - \left(\left(\frac{\text{(Individual Test Sample Ratio)} - \text{(Background Avg Ratio)}}{\text{(Minimum Inhibition Ratio)} - \text{(Background Average Ratio)}}\right) * 100\right)$$

Cell Proliferation Analysis

WSU-DLCL2 suspension cells were purchased from DSMZ (German Collection of Microorganisms and Cell Cultures, Braunschweig, Germany). RPMI/Glutamax Medium, Penicillin-Streptomycin, Heat Inactivated Fetal Bovine Serum were purchased from Life Technologies, Grand Island, N.Y., USA. V-bottom polypropylene 384-well plates were purchased from Greiner Bio-One, Monroe, N.C., USA. Cell culture 384-well white opaque plates were purchased from Perkin Elmer, Waltham, Mass., USA. Cell-Titer Glo® was purchased from Promega Corporation, Madison, Wis., USA. SpectraMax M5 plate reader was purchased from Molecular Devices LLC, Sunnyvale, Calif., USA.

WSU-DLCL2 suspension cells were maintained in growth medium (RPMI 1640 supplemented with 10% v/v heat inactivated fetal bovine serum and cultured at 37° C. under 5% CO2. Under assay conditions, cells were incubated in Assay Medium (RPMI 1640 supplemented with 20% v/v heat inactivated fetal bovine serum and 100 units/mL penicillin-streptomycin) at 37° C. under 5% CO2.

For the assessment of the effect of compounds on the proliferation of the WSU-DLCL2 cell line, exponentially growing cells were plated in 384-well white opaque plates at a density of 1250 cell/ml in a final volume of 50 μl of assay medium. A compound source plate was prepared by performing triplicate nine-point 3-fold serial dilutions in DMSO, beginning at 10 mM (final top concentration of compound in the assay was 20 μM and the DMSO was 0.2%). A 100 nL aliquot from the compound stock plate was added to its respective well in the cell plate. The 100% inhibition control consisted of cells treated with 200 nM final concentration of staurosporine and the 0% inhibition control consisted of DMSO treated cells. After addition of compounds, assay plates were incubated for 6 days at 37° C., 5% $CO_2$, relative humidity >90% for 6 days. Cell viability was measured by quantization of ATP present in the cell cultures, adding 35 μl of Cell Titer Glo® reagent to the cell plates. Luminescence was read in the SpectraMax M5. The concentration inhibiting cell viability by 50% was determined using a 4-parametric fit of the normalized dose response curves. $IC_{50}$ values for this assay are presented in Table 3 below.

TABLE 3

| | EZH2 IC50 peptide v2 | Y641F IC50 | WSU prolif IC50 | WSU ELISA IC50 |
|---|---|---|---|---|
| Compound I (free base) | 0.01299 | 0.01107 | 0.369 | 0.29 |

In Vivo Study—SUDHL10 Human Lymphoma Cell Line Mice

Female Fox Chase SCID® Mice (CB17/Icr-Prkdcscid/IcrIcoCrl, Beijing Vitalriver Laboratory Animal Co., LTD) were 6-8 weeks old and had a body-weight (BW) range of 16.0-21.1 g on D1 of the study. The animals were fed ad libitum with water (sterile) and irradiation sterilized dry granule food. The mice were housed on corn cob bedding in static microisolators on a 12-hour light cycle at 20-22° C. (68-72° F.) and 40-60% humidity. All procedures comply with the recommendations of the *Guide for Care* and *Use of Laboratory Animals* with respect to restraint, husbandry, surgical procedures, feed and fluid regulation, and veterinary care.

Tumor Cell Culture

Human lymphoma cell line SUDHL10 was obtained from DSMZ and maintained at the CRO as suspension cultures in RPMI-1640 medium containing 100 units/mL penicillin G sodium salt, 100 g/mL streptomycin and 10% fetal bovine serum. The cells were cultured in tissue culture flasks in a humidified incubator at 37° C., in an atmosphere of 5% CO2 and 95% air. Only cultures below passage 12 were used for implantation In Vivo Tumor Implantation SUDHL10 human lymphoma cell line was harvested during mid-log phase growth, and resuspended in PBS with 50% Matrigel™ (BD Biosciences). Each mouse received $1 \times 10^7$ cells (0.2 mL cell suspension) subcutaneously in the right flank. Tumors were calipered in two dimensions to monitor growth as the mean volume approached the desired 80-120 $mm^3$ range. Tumor size, in $mm^3$, was calculated from:

$$\text{Tumor Volume} = \frac{w^2 \times l}{2}$$

where w=width and l=length, in mm, of the tumor. Tumor weight can be estimated with the assumption that 1 mg is equivalent to 1 mm³ of tumor volume. After 10 days mice with 72-256 mm³ tumors were sorted into four groups (n=16 per group) with mean tumor volumes of 173-179 mm³.

Test Articles

The hydrobromide of Compound I was stored at room temperature and protected from light. On each treatment day, a fresh compound formulations were prepared by suspending the powder in 0.5% sodium carboxymethylcellulose (NaCMC) and 0.1% Tween® 80 in deionized water. The vehicle, 0.5% NaCMC and 0.1% Tween® 80 in deionized water, was used to treat the control group at the same schedule. Formulations were stored away from light at 4° C. prior to administration.

Treatment Plan

Mice were treated with doses of the hydrobromide of Compound I ranging from 125-500 mg/kg and at a BID (twice a day every 12 h) schedules for 28 days by oral gavage. Each dose was delivered in a volume of 0.2 mL/20 g mouse (10 mL/kg), and adjusted for the last recorded weight of individual animals. On day 25 the 8 mice with the smallest tumors per group were chosen for a tumor growth delay endpoint (observation up to 60 days). The remaining animals were euthanized on day 28 3 h after the last dose for tumor collection.

Median Tumor Volume (MTV) and Tumor Growth Inhibition (TGI) Analysis

Treatment efficacy was determined on the last treatment day. MTV(n), the median tumor volume for the number of animals, n, evaluable on the last day, was determined for each group. Percent tumor growth inhibition (% TGI) can be defined several ways. First, the difference between the MTV(n) of the designated control group and the MTV(n) of the drug-treated group is expressed as a percentage of the MTV(n) of the control group:

$$\%TGI = \left(\frac{MTV(n)_{control} - MTV(n)_{treated}}{MTV(n)_{control}}\right) \times 100$$

Another way of calculating % TGI is taking the change of the tumor size from day 1 to day n into account with n being the last treatment day.

$$\%TGI = \left(\frac{\Delta MTV(n)_{control} - \Delta MTV(n)_{treated}}{\Delta MTV(n)_{control}}\right) \times 100$$

$$\Delta MTV_{control} = MTV(n)_{control} - MTV(1)_{control}$$

$$\Delta MTV_{treated} = MTV(n)_{treated} - MTV(1)_{treated}$$

Tumor Growth Delay Analysis

Eight mice per group were kept alive after the last treatment day for tumor growth delay analysis. Tumors were calipered twice-weekly and each test animal was euthanized when its neoplasm reached the endpoint volume of 2000 mm³ or on the pre-specified last day of the study, whichever came first. Kaplan Meier survival analysis was performed.

Toxicity

Animals were weighed daily on Days 1-5, and then twice weekly until the completion of the study. The mice were examined frequently for overt signs of any adverse, treatment related side effects, which were documented. Acceptable toxicity for the maximum tolerated dose (MTD) was defined as a group mean BW loss of less than 20% during the test, and not more than 10% mortality due to TR deaths. A death was to be classified as TR if it was attributable to treatment side effects as evidenced by clinical signs and/or necropsy, or due to unknown causes during the dosing period. A death was to be classified as NTR if there was evidence that the death was unrelated to treatment side effects. NTR deaths during the dosing interval would typically be categorized as NTRa (due to an accident or human error) or NTRm (due to necropsy-confirmed tumor dissemination by invasion and/or metastasis). Orally treated animals that die from unknown causes during the dosing period may be classified as NTRu when group performance does not support a TR classification and necropsy, to rule out a dosing error, is not feasible.

Sampling

On day 28 eight mice with the largest tumors were sampled in a pre-specified fashion to assess target inhibition in tumors. Tumors were harvested from specified mice under RNAse free conditions and bisected. Total tumor weight was measured. Frozen tumor tissue from each animal was snap frozen in liquid $N_2$ and pulverized with a mortar and pestle.

Statistical and Graphical Analyses

All statistical and graphical analyses were performed with Prism 3.03 (GraphPad) for Windows. To test statistical significance between the control and treated groups over the whole treatment time course a repeated measures ANOVA test followed by Dunnets multiple comparison post test was employed. Prism reports results as non-significant (ns) at $P>0.05$, significant (symbolized by "*") at $0.01<P<0.05$, very significant ("") at $0.001<P<0.01$ and extremely significant ("*") at $P<0.001$. For the tumor growth delay arm of the study the percentage of animals in each group remaining in the study versus time was presented in a Kaplan-Meier survival plot.

Histone Extraction

For isolation of histones, 60-90 mg tumor tissue was homogenized in 1.5 ml nuclear extraction buffer (10 mM Tris-HCl, 10 mM MgCl2, 25 mM KCl, 1% Triton X-100, 8.6% Sucrose, plus a Roche protease inhibitor tablet 1836145) and incubated on ice for 5 minutes. Nuclei were collected by centrifugation at 600 g for 5 minutes at 4° C. and washed once in PBS. Supernatant was removed and histones extracted for one hour, with vortexing every 15 minutes, with 0.4 N cold sulfuric acid. Extracts were clarified by centrifugation at 10000 g for 10 minutes at 4° C. and transferred to a fresh microcentrifuge tube containing 10× volume of ice cold acetone. Histones were precipitated at −20° C. for 2 hours-overnight, pelleted by centrifugation at 10000 g for 10 minutes and resuspended in water.

ELISA

Histones were prepared in equivalent concentrations in coating buffer (PBS+0.05% BSA) yielding 0.5 ng/ul of sample, and 100 ul of sample or standard was added in duplicate to 2 96-well ELISA plates (Thermo Labsystems, Immulon 4HBX #3885). The plates were sealed and incubated overnight at 4° C. The following day, plates were washed 3× with 300 ul/well PBST (PBS+0.05% Tween 20; 10×PBST, KPL #51-14-02) on a Bio Tek plate washer. Plates were blocked with 300 ul/well of diluent (PBS+2% BSA+0.05% Tween 20), incubated at RT for 2 hours, and washed 3× with PBST. All antibodies were diluted in diluent. 100 ul/well of anti-H3K27me3 (CST #9733, 50% glycerol stock 1:1,000) or anti-total H3 (Abcam ab1791, 50% glycerol 1:10,000) was added to each plate. Plates were incubated for 90 min at RT and washed 3× with PBST. 100 ul/well of anti-Rb-IgG-HRP (Cell Signaling Technology, 7074) was added 1:2,000 to the H3K27Me3 plate and 1:6,000 to the H3 plate and incubated for 90 min at RT. Plates were washed 4× with PBST. For detection, 100 ul/well of TMB substrate (BioFx Laboratories, #TMBS) was added and plates incubated in the dark at RT for 5 min. Reaction was stopped with 100 ul/well 1N $H_2SO_4$. Absorbance at 450 nm was read on SpectaMax M5 Microplate reader.

Results:

Mice bearing SUDHL10 tumor xenografts were treated with the hydrobromide of Compound I at the maximal tolerated dose of 500 mg/kg BID and fractions of the MTD (½ and ¼ MTD). All doses were well tolerated for 28 days without any significant body weight loss. There was one non-treatment related death in the 500 mg/kg group on day 15 due to a dosing error. All doses resulted in tumor growth inhibition when compared to vehicle on day 28 (Table 4), and the 250 mg/kg and 500 mg/kg BID groups induced regressions (TGI>100%).

TABLE 4

Summary of tumor growth inhibition values induced by hydrobromide of Compound I in SUDHL10 xenografts

| Group | % TGI from day 1 | % TGI from day 8 |
| --- | --- | --- |
| 125 mg/kg BID | 54 | 57 |
| 250 mg/kg BID | 101 | 113 |
| 500 mg/kg BID | 104 | 115 |

Figure 12A:
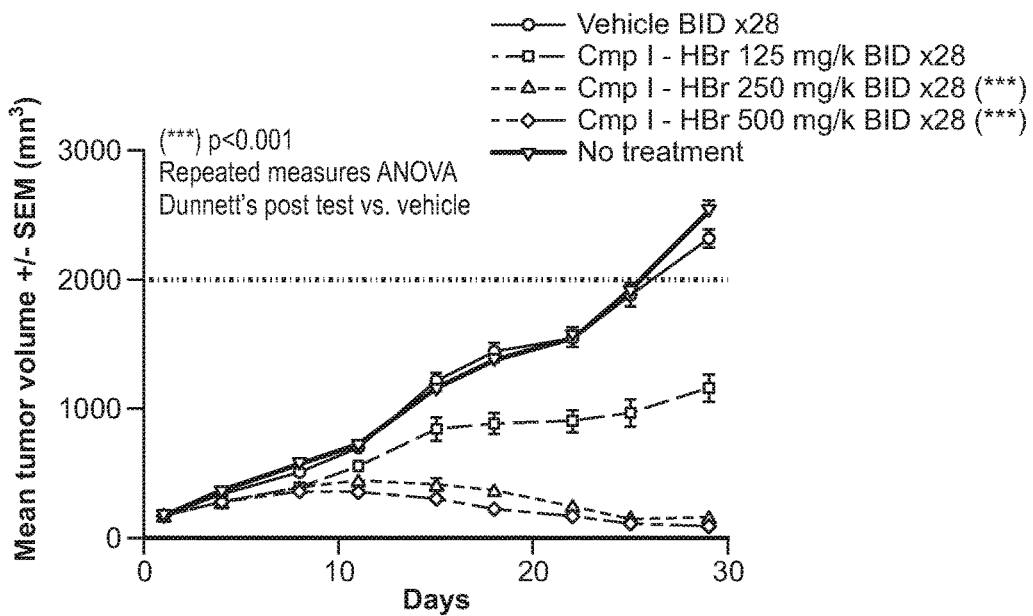
FIGS. 12-14 show the results from in vivo studies of the hydrobromide of Compound I in a human lymphoma cell line.
Figure 12B:
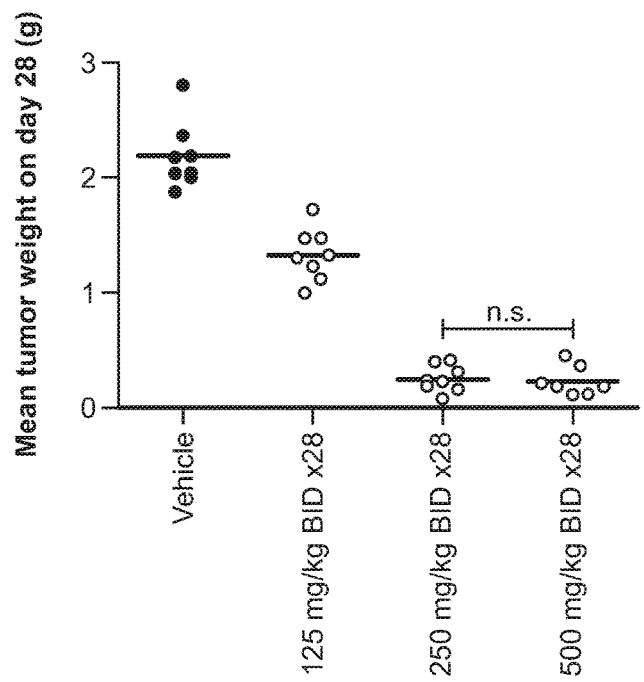

FIG. 12A shows the growth of the SUDHL10 xenograft tumors over time for the different treatment groups. The 125 mg/kg BID group was not significantly different from the vehicle group by repeated measures ANOVA and Dunnett's post test, but the mean terminal tumor size on day 28 was significantly smaller than the one in the vehicle group (2 way ANOVA with Bonferroni post test, p<0.0001). Dosing of 250 mg/kg BID and 500 mg/kg BID of the hydrobromide of Compound I for 28 days induced comparable regression responses as the terminal tumor weights on day 28 were similar for those 2 groups (FIG. 12B).

Figure 13:
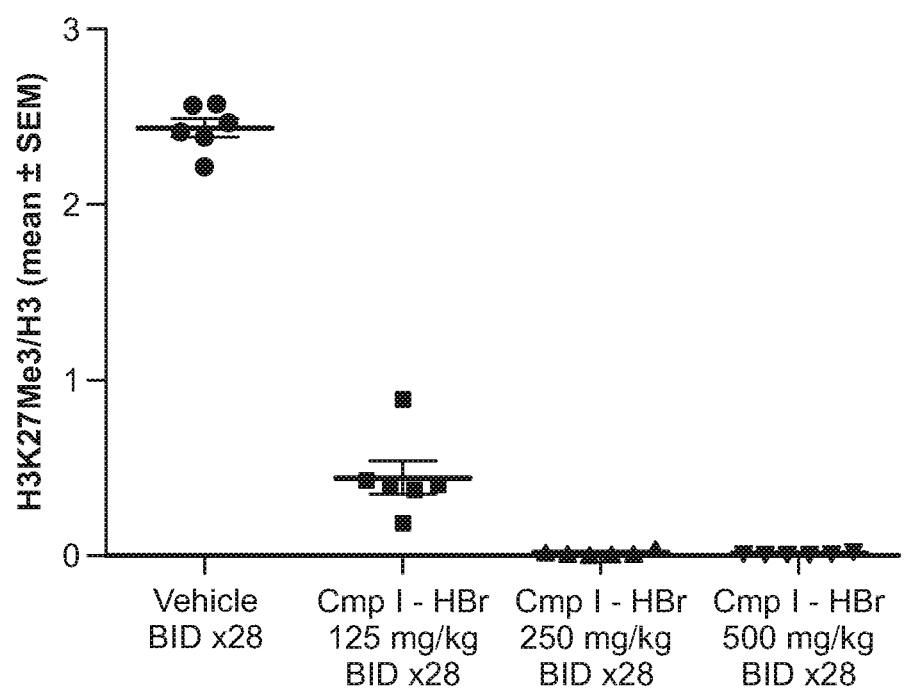

Histones isolated from tumors harvested on day 28 (3 h after the last dose) were subjected to ELISA analysis for global H3K27me3 levels. FIG. 13 shows a clear dose dependent down-regulation of the H3K27me3 methyl mark with treatment by the hydrobromide of Compound I. This figure shows global H3K27me3 methylation in SUDHL10 tumors from mice treated with the hydrobromide of Compound I for 28 days.

Figure 14A:
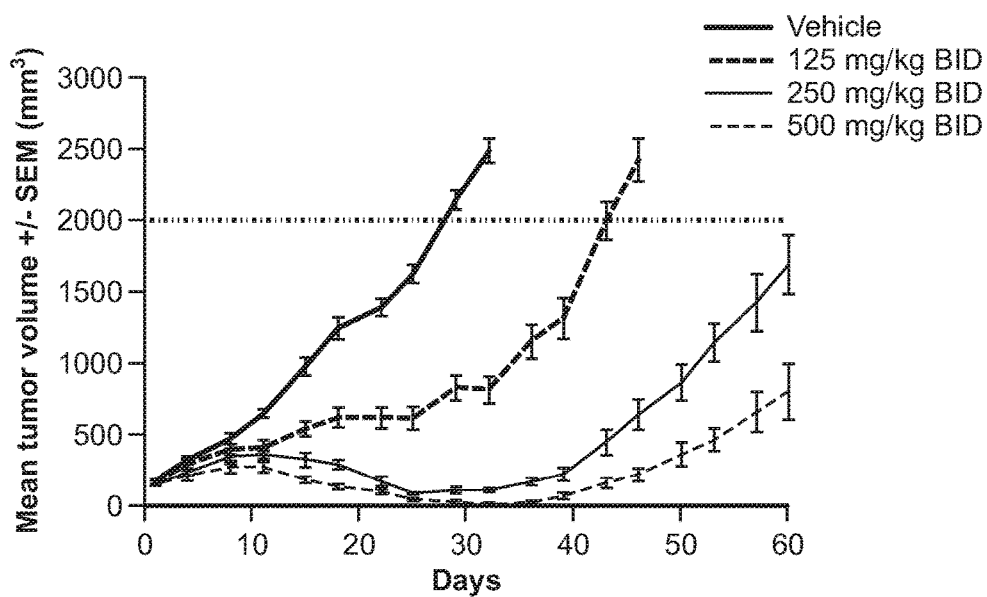
Figure 14B:
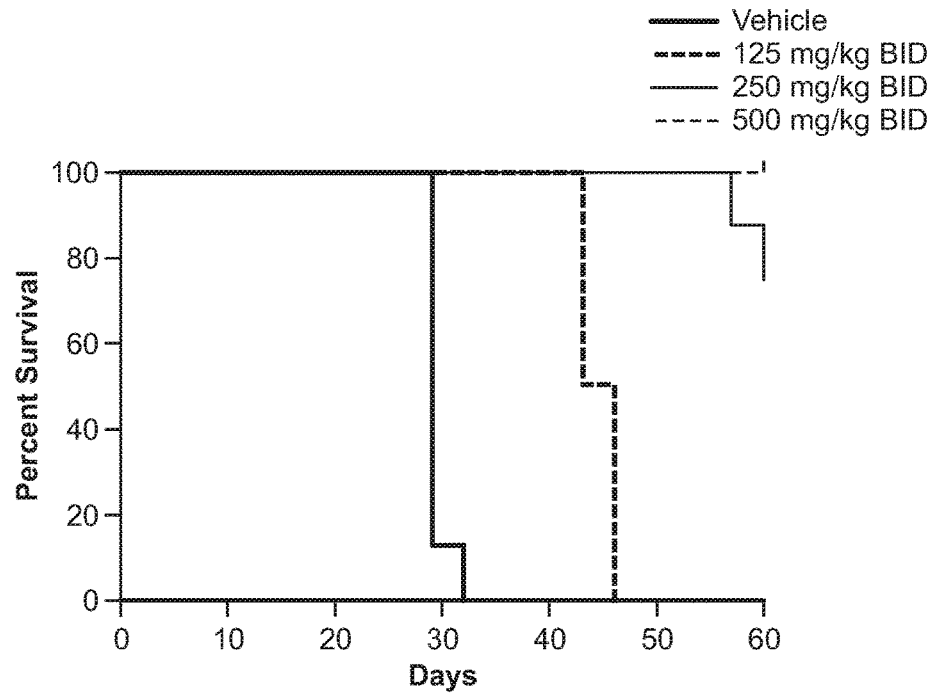

On day 25 eight mice per group with smallest tumors were chosen for a tumor growth delay study to assess the regrowth of tumors after dosing stop on day 28. Mice were euthanized when their tumors reached a size of 2000 $mm^3$ or on day 60 (whichever comes first). These data were used to perform a Kaplan Meier survival analysis. FIG. 14A shows that tumor re-growth was clearly dose-dependent, and all mice treated with the highest dose of 500 mg/kg BID for 28 days survived until day 60. Only 2 mice had to be euthanized in the 250 mg/kg group before day 60. Mice in the 125 mg/kg group had a clear survival benefit over vehicle treated mice with an increase in median survival of 15.5 days (FIG. 14B).

Anti-Cancer Effect of the Hydrobromide of Compound I on the Pfeiffer Human Diffused Large B-Cell Lymphoma Mouse Xenograft Model The monohydrobromide of Compound I was tested for its anti-cancer activity in Pfeiffer mouse xenograft model, which is a human diffused large B-Cell lymphoma xenograft model. Female of 5-week old NSG mice (Jackson Labs, Bar Harbor, Ma.) were implanted subcutaneously with 20 to 25 mg tumor fragments. Treatment was started approximately 31 days after the tumor implantation, when the average tumors reached approximately 365 $mm^3$. The treatment scheme is described in Table 5.

TABLE 5

Dosing Scheme

| Group | No. of Animals | Treatment | Route and Schedule |
| --- | --- | --- | --- |
| A | 9 | Vehicle (0.5% Methyl Cellulose, 0.1% Tween-80) | PO; qd × 28 |
| B | 9 | 34.2 mg/kg Compound I (HBr salt) | PO; qd × 28 |
| C | 9 | 114 mg/kg Compound I (HBr salt) | PO; qd × 28 |
| D | 9 | 342 mg/kg Compound I (HBr salt) | PO; qd × 28 |
| E | 9 | 1140 mg/kg Compound I (HBr salt) | PO; qd × 12[§] |

[§]Due to compound tolerability issue, only 12 daily doses were given to this group.

Tumor volume was followed throughout the experiment. Tumor volume was measured two times weekly after the start of treatment. Tumor burden (mg=$mm^3$) was calculated from caliper measurements by the formula for the volume of a prolate ellipsoid (L×$W^2$)/2 where L and W are the respective orthogonal length and width measurements (mm).

Day 1 was the day of the first treatment, and Day 28 was the day of the last treatment. This study was terminated 36 days after the last dose, so Day 64 was the day of study termination. The primary endpoints used to evaluate efficacy in this study were complete tumor regressions (CR), tumor sizes among groups, and percentage of tumor inhibition at the end of the study. A complete response was defined as a decrease in tumor size to an undetectable size (<20 $mm^3$) at the end of the study. Values for percentage of tumor inhibition were calculated from the formula [1−(ΔT/ΔC)]×100, where ×T and ×C are changes in mean tumor volume (Δ growth) for each treated (T) and vehicle control group (C). $T_0$ and $C_0$ (one day before the first dose) were used for the starting tumor volume. Additionally, tumor volumes which were taken one day after the last dose ($T_{29}$ and $C_{29}$) were used for the calculation of ΔT and ΔC. When the value was more than 100%, it was concluded as 100%. The formula used for the calculation of percentage of tumor inhibition is shown below.

$$\text{Percentage of tumor inhibition} = \left\{1 - \frac{T_{29} - T_0}{C_{29} - C_0}\right\} \times 100\%$$

Figure 15:
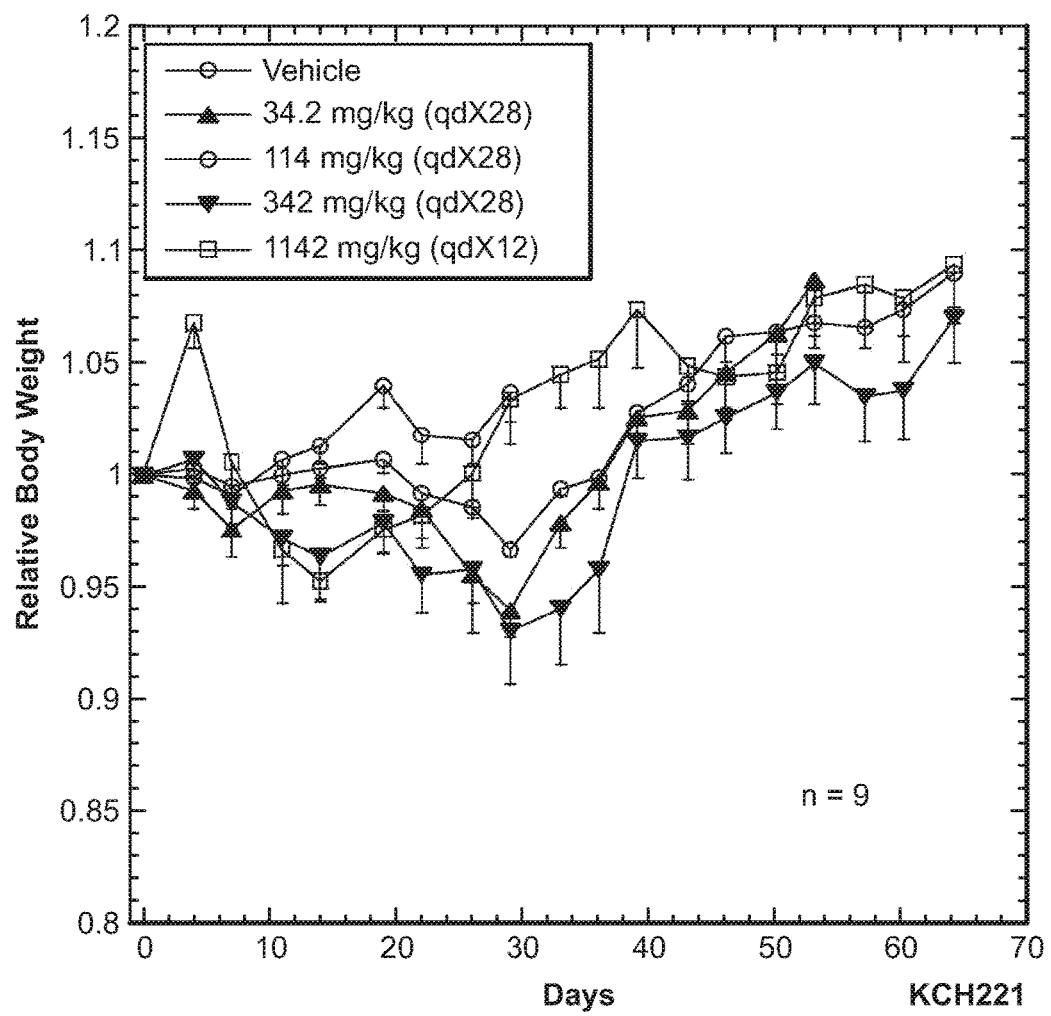
FIGS. 15-16 show the anti-cancer effect of the hydrobromide of Compound I on a lymphoma mouse xenograft model.

During the treatment period, it was found that animals cannot tolerate the daily treatment of 1142 mg/kg the hydrobromide of Compound I and three animals in this group (group E) required euthanasia after first week of treatment due to loss of more than 20% baseline bodyweight. Hence, drug administration for this group was stopped after 12 doses. Animals in other three dosing groups, except one animal in group D (342 mg/kg hydrobromide of Compound I), all tolerated the 28-day treatment well with minimal bodyweight loss. Relative mouse body weight was graphed in FIG. 15. Animal bodyweight obtained on Day 0 was used as the baseline bodyweight in the graph.

Figure 16:
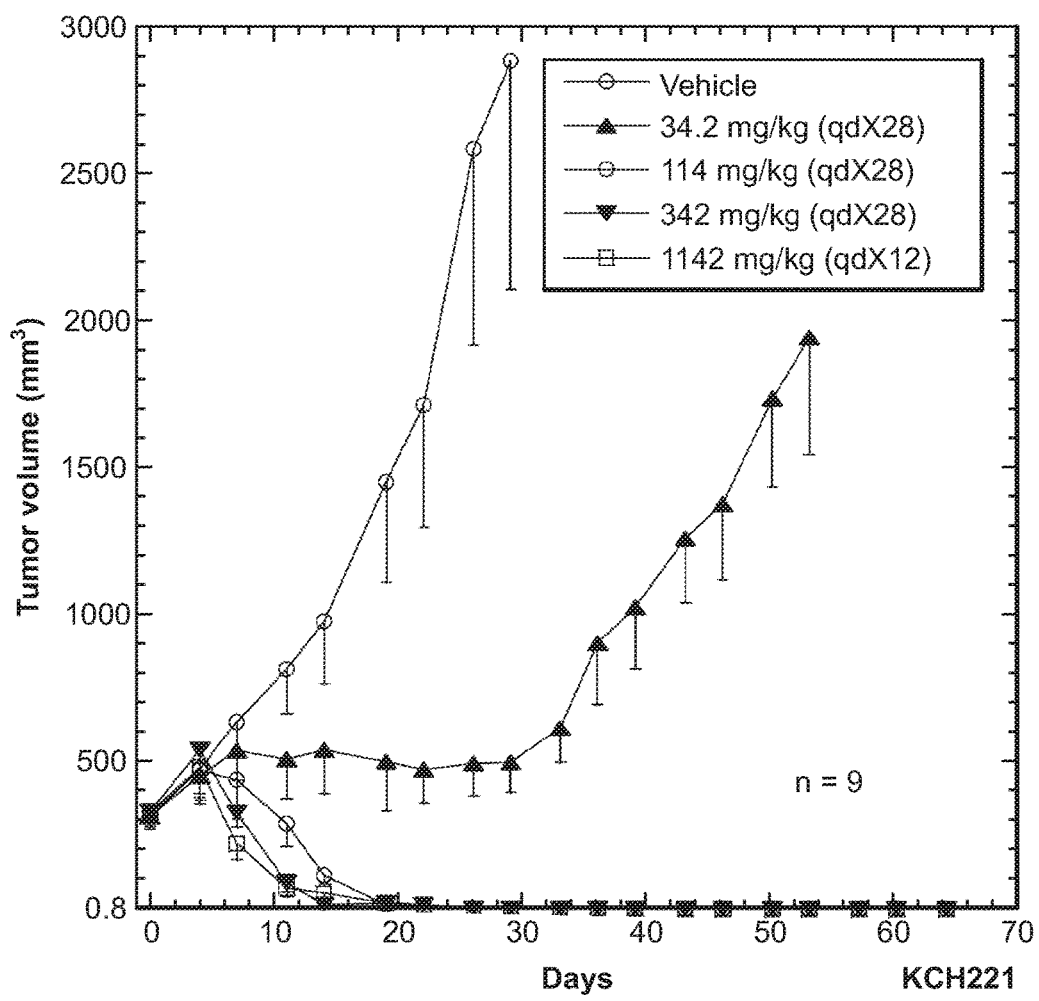

The hydrobromide of Compound I showed potent and long-lasting anti-cancer activity in Pfeiffer model with 100% of CR rate in three out of four dosing group (Table 6). Moreover, tumor re-growth was not observed even 36 days after cessation of the treatment. This suggests that all the tumor cells were killed during the treatment. Although tumor re-growth was observed in the group with the lowest dose (group B, 34.2 mg/kg), clear tumor stasis activity was observed during the treatment period (FIG. 16). Tumor only started to grow upon cessation of the treatment (FIG. 16). This result also suggests that the tumor stasis activity observed in group B is indeed test article-induced activity.

TABLE 6

Results summary table

| Group | Treatment | CR | TV (Mean ± StDev) | Percentage of tumor inhibition | P value[ϵ] |
|---|---|---|---|---|---|
| A | Vehicle | 0 | 2882 ± 2190 | n/a | n/a |
| B | 34.2 mg/kg Cmp I (HBr) | 0 | 497 ± 287 | 93% | P < 0.05 |
| C | 114 mg/kg Cmp I (HBr) | 9 | 0 | 100% | P < 0.05 |
| D | 342 mg/kg Cmp I (HBr) | 8[£] | 0 | 100% | P < 0.05 |
| E | 1140 mg/kg Cmp I (HBr) | 6[¥] | 0 | 100% | P < 0.05 |

[ϵ]One way analysis of variance (ANOVA) followed by Dunnett's multiple comparison test (Prism software version 5.02, Lake Forest, CA).
[£]1 animal was euthanized on day 36 for low bodyweight.
[¥]3 animals were euthanized on day 7, 9, and 11, individually for low bodyweight.

The invention claimed is:

1. A method of inhibiting the histone methyltransferase activity of EZH2 in a subject in need thereof comprising administering to the subject an effective amount of a solid crystalline form of N-((4,6-dimethyl-2-oxo-1,2-dihydropyridin-3-yl)methyl)-5-(ethyl (tetrahydro-2H-pyran-4-yl)amino)-4-methyl-4'-(morpholinomethyl)-[1,1'-biphenyl]-3-carboxamide hydrobromide, wherein the solid crystalline form exhibits an X-ray powder diffraction pattern having one or more characteristic peaks expressed in degrees 2-theta at about 3.9+/−0.3 degrees, about 17.5+/−0.3 degrees, and about 22.0+/−0.3 degrees 2-theta.

2. A method of inhibiting the histone methyltransferase activity of EZH2 in vitro comprising administering a solid crystalline form of N-((4,6-dimethyl-2-oxo-1,2-dihydropyridin-3-yl)methyl)-5-(ethyl (tetrahydro-2H-pyran-4-yl)amino)-4-methyl-4'-(morpholinomethyl)-[1,1'-biphenyl]-3-carboxamide hydrobromide, wherein the solid crystalline form exhibits an X-ray powder diffraction pattern having one or more characteristic peaks expressed in degrees 2-theta at about 3.9+/−0.3 degrees, about 17.5+/−0.3 degrees, and about 22.0+/−0.3 degrees 2-theta.

3. The method of claim 1, wherein said solid crystalline form exhibits an X-ray powder diffraction pattern having

```
SEQUENCE LISTING

<160> NUMBER OF SEQ ID NOS: 2

<210> SEQ ID NO 1
<211> LENGTH: 26
<212> TYPE: PRT
<213> ORGANISM: Artificial Sequence
<220> FEATURE:
<223> OTHER INFORMATION: Chemically synthesized polypeptide
<220> FEATURE:
<221> NAME/KEY: MISC_FEATURE
<222> LOCATION: (26)..(26)
<223> OTHER INFORMATION: wherein a biotin and an amide are conjugated

<400> SEQUENCE: 1

Ala Thr Lys Ala Ala Arg Lys Ser Ala Pro Ala Thr Gly Gly Val Lys
1               5                   10                  15

Lys Pro His Arg Tyr Arg Pro Gly Gly Lys
            20                  25

<210> SEQ ID NO 2
<211> LENGTH: 26
<212> TYPE: PRT
<213> ORGANISM: Artificial Sequence
<220> FEATURE:
<223> OTHER INFORMATION: Chemically synthesized polypeptide
<220> FEATURE:
<221> NAME/KEY: MISC_FEATURE
<222> LOCATION: (7)..(7)
<223> OTHER INFORMATION: wherein the lysine is dimethylated
<220> FEATURE:
<221> NAME/KEY: MISC_FEATURE
<222> LOCATION: (26)..(26)
<223> OTHER INFORMATION: wherein a biotin and an amide are conjugated

<400> SEQUENCE: 2

Ala Thr Lys Ala Ala Arg Lys Ser Ala Pro Ala Thr Gly Gly Val Lys
1               5                   10                  15

Lys Pro His Arg Tyr Arg Pro Gly Gly Lys
            20                  25
``` one or more characteristic peaks expressed in degrees 2-theta selected from peaks at about 3.9+/−0.3 degrees, about 14.3+/−0.3 degrees, about 18.7+/−0.3 degrees, about 23.3+/−0.3 degrees, and about 23.6+/−0.3 degrees 2-theta.

4. The method of claim 1, wherein said solid crystalline form exhibits an X-ray powder diffraction pattern having at least 5 characteristic peaks expressed in degrees 2-theta at about 3.9+/−0.3 degrees, 10.1+/−0.3 degrees, 14.3+/−0.3 degrees, 17.5+/−0.3 degrees, 18.7+/−0.3 degrees, 20.6+/−0.3 degrees, 20.9+/−0.3 degrees, 21.8+/−0.3 degrees, 22.0+/−0.3 degrees, 23.3+/−0.3 degrees and 23.6+/−0.3 degrees 2-theta.

5. The method of claim 1, wherein said solid crystalline form exhibits an X-ray powder diffraction pattern having at least 6 characteristic peaks expressed in degrees 2-theta selected from peaks at about 3.9+/−0.3 degrees, 10.1+/−0.3 degrees, 14.3+/−0.3 degrees, 17.5+/−0.3 degrees, 18.7+/−0.3 degrees, 20.6+/−0.3 degrees, 20.9+/−0.3 degrees, 21.8+/−0.3 degrees, 22.0+/−0.3 degrees, 23.3+/−0.3 degrees and 23.6+/−0.3 degrees 2-theta.

6. The method of claim 1, wherein said solid crystalline form exhibits an X-ray powder diffraction pattern substantially in accordance with FIG. 1.

7. The method of claim 1, wherein said solid crystalline form exhibits a differential scanning calorimetry thermogram having a characteristic peak expressed in units of ° C. at a temperature of 255+/−5° C.

8. The method of claim 1, wherein said solid crystalline form exhibits a differential scanning calorimetry thermogram substantially in accordance with FIG. 3.

9. The method of claim 1, wherein said solid crystalline form is substantially free of impurities.

10. The method of claim 1, wherein said solid crystalline form is substantially free of amorphous N-((4,6-dimethyl-2-oxo-1,2-dihydropyridin-3-yl)methyl)-5-(ethyl(tetrahydro-2H-pyran-4-yl)amino)-4-methyl-4'-(morpholinomethyl)-[1,1'-biphenyl]-3-carboxamide hydrobromide.

11. The method of claim 2, wherein said solid crystalline form exhibits an X-ray powder diffraction pattern having one or more characteristic peaks expressed in degrees 2-theta selected from peaks at about 3.9+/−0.3 degrees, about 14.3+/−0.3 degrees, about 18.7+/−0.3 degrees, about 23.3+/−0.3 degrees, and about 23.6+/−0.3 degrees 2-theta.

12. The method of claim 2, wherein said solid crystalline form exhibits an X-ray powder diffraction pattern having at least 5 characteristic peaks expressed in degrees 2-theta at about 3.9+/−0.3 degrees, 10.1+/−0.3 degrees, 14.3+/−0.3 degrees, 17.5+/−0.3 degrees, 18.7+/−0.3 degrees, 20.6+/−0.3 degrees, 20.9+/−0.3 degrees, 21.8+/−0.3 degrees, 22.0+/−0.3 degrees, 23.3+/−0.3 degrees and 23.6+/−0.3 degrees 2-theta.

13. The method of claim 2, wherein said solid crystalline form exhibits an X-ray powder diffraction pattern having at least 6 characteristic peaks expressed in degrees 2-theta selected from peaks at about 3.9+/−0.3 degrees, 10.1+/−0.3 degrees, 14.3+/−0.3 degrees, 17.5+/−0.3 degrees, 18.7+/−0.3 degrees, 20.6+/−0.3 degrees, 20.9+/−0.3 degrees, 21.8+/−0.3 degrees, 22.0+/−0.3 degrees, 23.3+/−0.3 degrees and 23.6+/−0.3 degrees 2-theta.

14. The method of claim 2, wherein said solid crystalline form exhibits an X-ray powder diffraction pattern substantially in accordance with FIG. 1.

15. The method of claim 2, wherein said solid crystalline form exhibits a differential scanning calorimetry thermogram having a characteristic peak expressed in units of ° C. at a temperature of 255+/−5° C.

16. The method of claim 2, wherein said solid crystalline form exhibits a differential scanning calorimetry thermogram substantially in accordance with FIG. 3.

17. The method of claim 2, wherein said solid crystalline form is substantially free of impurities.

18. The method of claim 2, wherein said solid crystalline form is substantially free of amorphous N-((4,6-dimethyl-2-oxo-1,2-dihydropyridin-3-yl)methyl)-5-(ethyl(tetrahydro-2H-pyran-4-yl)amino)-4-methyl-4'-(morpholinomethyl)-[1,1'-biphenyl]-3-carboxamide hydrobromide.

\* \* \* \* \*